United States Patent [19]
Blackwood et al.

[11] Patent Number: 5,302,519
[45] Date of Patent: Apr. 12, 1994

[54] METHOD OF PRODUCING A MAD POLYPEPTIDE

[75] Inventors: Elizabeth M. Blackwood, Kirkland; Robert N. Eisenman; Donald E. Ayer, Jr., both of Mercer Island, all of Wash.

[73] Assignee: Fred Hutchinson Cancer Research Center, Seattle, Wash.

[21] Appl. No.: 903,710

[22] Filed: Jun. 23, 1992

Related U.S. Application Data

[63] Continuation-in-part of Ser. No. 756,195, Sep. 9, 1991, abandoned.

[51] Int. Cl.$^5$ .................. C12Q 1/68; C12P 21/06; G01N 33/53; C07H 15/12
[52] U.S. Cl. .................. 435/69.1; 435/6; 435/69.3; 435/70.21; 435/240.2; 435/320.1; 530/350; 530/351; 536/23.1; 536/23.5
[58] Field of Search .................. 435/2, 4, 6, 7, 69.1, 435/240.2, 320.1, 70.21, 69.3; 530/350, 351; 536/23.1, 23.5

[56] References Cited

PUBLICATIONS

Stone, J. et al., *Mol. Cell. Biol.* 7, 1697 (1987).
Enrietto, P. J., *Virology* 168, 256 (1989).
Nakajima, H., M. Ikeda, N. Tsuchida, S. Nishimura, Y. Taya, *Oncogene* 4, 999 (1989).
Crouch, D. H., C. Lang, D. A. F. Gillespie. Definition of the activities and properties of c-myc required to inhibit cell differentiation. *Oncogene* 5, 863 (9190).
Freytag, S. O., C. V. Dang, W. M. F. Lee, *Cell Growth Differ.*, 1, 339 (1990).
Smith, M. J., D. C. Charron-Prochownik, E. V. Prochownik, *Mol. Cell. Biol.* 10, 5333 (1990).
Penn, L. J. Z. et al., *Mol. Cell. Biol.* 10, 4961 (1990).
Jones, N. Transcriptional regulation by dimerization: two sides to an incestuous relationship. *Cell* 61, 9–11 (1990).
Olson, E. N., *Genes Dev.* 4, 1454 (1990).
Murre, C., P. S. McCaw, D. Baltimore. A new DNA binding and dimerization motif in immunoglobulin enhancer binding, *daughterless, MyoD*, and *myc* proteins. *Cell* 56, 777–783 91989).
Tapscott, S. J., Davis, R. L., Thayer, M. J., Cheng, P. F. Weintraub, H. and Lassar, A. B. A nuclear phosphoprotein requiring a Myc homology region to convert fibroblasts to myoblasts. *Science* 242, 405–411 (1988).
Voronova, A. and D. Baltimore, *Proc. Natl. Acad. Sci. U.S.A.* 87, 4722 (1990).
Murre, C., McCaw, P. S. Vaessin, H., Caudy, M., Jan, L. Y., Jan, Y. N. Cabrera, C. V., Buskin, J. N., Hauschka, S. D., Lassar, A. B., Weintraub, H. and D. Baltimore. Interactions between heterologous helix–loop–helix proteins generates complexes that bind specifically to a common DNA sequence. *Cell* 58, 537–544 (1989).
Davis, R. L., P.-F. Cheng, A. B. Lassar, H. Weintraub, *Cell.* 60, 733 (1990).
Landschulz, W. H., P. F. Johnson, S. L. McKnight. The leucine zipper: a hypothetical structure common to a new class of DNA binding proteins. *Science* 240, 1759–1764 (1988).
O'Shea, E. K., R. H. Rutkowski, P. S. Kim. Evidence that the leucine zipper is a coiled coil. *Science* 243, 538–542 (1989).

(List continued on next page.)

Primary Examiner—Robert J. Hill, Jr.
Assistant Examiner—Gian P. Wang
Attorney, Agent, or Firm—Christensen, O'Connor, Johnson & Kindness

[57] ABSTRACT

Nucleic acid molecules capable of hybridizing under stringent conditions to the nucleotide sequence residing between positions 1 and 453 of the max cDNAs shown in FIG. 2, or to the nucleotide sequence residing between positions 148 and 810 of the mad cDNAs shown in FIG. 14. The Max polypeptide when associated with the Myc or Mad polypeptide is capable of binding to nucleotide sequences containing CACGTG.

10 Claims, 46 Drawing Sheets

OTHER PUBLICATIONS

Vinson, C. R., P. B. Sigler, S. L. McKnight, *Science* 246, 911 (1989).

Kouzarides, T. and E. Ziff. The role of the leucine zipper in the fos-jun interaction. *Nature* 336, 646–651 (1988).

Blackwell, T. K., L. Kretzner, E. M. Blackwood, R. N. Eisenman, H. Weintraub. Sequence-Specific DNA–Binding by the c-Myc protein. *Science* 250, 1149 (1990.

Luscher, B. and R. N. Eisenman, "New Light on Myc and Myb. Part I. Myc." *Genes Dev.* 4(12a):2025–2035 (1990).

Cory, S. "Activation of cellular oncogenes in hematopoietic cells by chromosome translocation." *Advances in Cancer Research.* 1986.

Eisenman, R. N. "Nuclear Oncogenes" In: Oncogenes and the Molecular Origins of Cancer. (R. Weinberg, Ed.) Cold Spr. Harbor Press, Cold Springs, N.Y. pp. 175–221 (1989).

Magrath, I. "The pathogenesis of Burkitt's lymphoma." *Adv. Cancer Res.* 55:134–251 (1990).

Marshall, C. J. "Tumor suppressor genes." *Cell.* 64(2):313–326, 1991.

Dang, C. V. M. McGuire, M. Buckmire, W. M. F. Lee, *Nature* 337, 664–666 (1989).

Prendergast, G. and E. Ziff. Methylation-sensitive sequence-specific DNA binding by the c-yc basic region. *Science* 251, 186–189 (1991).

Dang, C. V., Barrett, J., Villa-Garcia, M., Resar, L. M. S., Kato, G. J. and Fearon, E. R. Intracellular leucine zipper interactions suggest c-Myc hetero-oligonmerization. *Mol. Cell. Biol.* 11, 954–962 (1991).

Blackwell, T. K. and H. Weintraub, *Science* 250, 1104 (1990).

Nakabeppu, Y., K. Ryder, D. Nathans, *Cell* 55, 907 (1988).

Halazonetis, T. D., J. Georgopoulos, M. E. Greenberg, P. Leder, *Cell* 55, 917 (1988).

Rauscher, F. J. III et al., *Science* 240, 1010 (1988).

Sassone-Corsi, P., W. W. Lamph, M. Kamps, I. M. Verma, *Cell* 54, 553 (1988).

Chiu, R. et al., *Cell* 54, 541 (1988).

Abrams, H., L. Rohrschneider, R. N. Eisenman, *Cell* 29, 427 (1982).

Donner, P., I. Gresier-Wilke, K. Moelling *Nature* 296, 262 (1982).

Hann, S. R. and R. N. Eisenman, *Mol. Cell. Biol.* 4, 2486 (1984).

Watt, R. A., A. R. Shatzman, M. Rosenberg, *Mol. Cell Biol.* 5, 448 (1985).

Ramsay, G. L. Stanton, M. Schwab, J. M. Bishop, *Mol. Cell. Biol.* 6, 4450 (1986).

De Greve, J. et al., *Mol. Cell. Biol.,* 8, 4381 (1988).

Dang, C. V., H. V. Dam, M. Buckmire, W. M. F. Lee, *Mol. Cell. Biol.* 9, 2477 (1989).

Saksela, K., T. P. Makela, G. Evan, K. Alitalo, *EMBO J.* 8, 149 (1989).

Kelly, K., B. H. Cochran, C. D. Stiles and P. Leder, "Cell-specific regulation of the c-myc gene by lymphocyte mitogens and platelet-derived growth factor." *Cell.* 35:603–610 (1983).

Heikkila, R., G. Schwab, E. Wickstrom, S. L. Loke, D. H. Pluznik, R. Watt and L. M. Neckers. "A c-myc antisense oligodeoxynucleotide inhibits entry into S phase but not progress from G0 to G1." *Nature.*

Macgregor, P. F., C. Abate, T. Curran, *Oncogene* 5, 451 (1990).

Hann, S. R., M. W. King, D. L. Bentley, C. W. Anderson, R. N. Eisenman, *Cell* 52, 185 (1988).

Wright, W. E., D. A. Sassoon, V. K. Lin, *Cell* 56, 607 (1989).

Chen, Q. et al., *EMBO* 9, 415 (1990).

Gregor, P. D., M. Sawadogo, R. G. Roeder, *Genes & Development* 4: 1740 (1990).

Hu, Y.-F., B. Luscher, A. Admon, N. Mermod, R. Tijan. Transcription factor AP-4 contains multiple dimerization domains that regulate dimer specificity. *Genes Dev.* 4, 1741 (1990).

Luscher, B., E. A. Kuenzel, E. G. Krebs, R. N. Eisenman, *EMBO J.* 8, 1111 (1989).

O'Shea, E. K., R. Rutkowski, W. F. Stafford III, P. S. Kim, *Science* 245, 646 (1989).

Lech, K., K. Anderson, R. Brent, *Cell* 52, 179 (1988).

Kato, G. J., J. Barrett, M. Villa-Garcia, C. V. Dang. An amino-terminal c-Myc domain required for neoplastic transformation activates transcription. *Mol. Cell. Biol.* 10, 5914–5920 (1990).

Kingston, R. E., A. S. Baldwin, P. A. Sharp, *Nature* 312, 280 (1984).

Kaddurah-Daouk, R., J. M. Greene, A. S. Baldwin, R. E. Kingston, *Genes Dev.* 1, 347 (1987).

(List continued on next page.)

OTHER PUBLICATIONS

Onclercq, R., P. Gilardi, A. Lavenu, C. Cremisi, *J. Virol.* 62, 4533 (1988).

Ptashne, M. *Nature* 335, 683 (1988).

Sigler, P. B. *Nature* 333, 210 (1988).

Mitchell, P. J. and R. Tijan, *Science* 245, 371 (1989).

Jones, N. *Cell* 61, 9 (1990).

Benezra, R., R. L. Davis, D. Lockshon, D. L. Turner, H. Weintraub, *Cell* 61, 49 (1990).

Davis, R. L., Cheng, P. -F., Lassar, A. B., & Weintraub, H., *Cell* 60, 733 (1990).

Blackwood, E. M., R. N. Eisenman. Max: a helix-loop-helix zipper protein that forms a sequence-specific DNA binding complex with Myc. *Science* 251, 1211-1217 (1991).

Prendergast, G. C., D. Lawe, E. B. Ziff, *Cell* 65, 395 (1991).

Blackwell, T. K., L. Kretzner, E. M. Blackwood, R. N. Eisenman, H. Weintraub, *Science* 250, 1149 (1990).

Luscher, B., R. N. Eisenman, *Mol. Cell. Biol.* 8, 2504 (1988).

Hann, S. R., C. B. Thompson, R. N. Eisenman, *Nature* 314, 366 (1985).

Rabbitts, P. H., Watson, J. V., Lamond, A., Forster, A., Stinson, M. A., Evan, G., Fischer, W., Atherton, E., Sheppard, R. and Rabbitts, T. H. Metabolism of c-Myc products: c-Myc mRNA and protein expression in the cell cycle. *EMBO J.* 4, 2009-2015 (1985).

Thompson, C. B., P. B. Challoner, P. E. Neiman, M. Groudine, *Nature* 314, 363 (1985).

Smith, M. J., D. C. Charron-Prochownik, E. V. Prochownik, *Mol. Cell. Biol.* 10, 5333 (1990).

Hann, S. R., H. D. Abrams, L. R. Rohrschneider, R. N. Eisenman, *Cell* 34, 789 (1983).

Ramsay, G., L. Stanton, M. Schwab, J. M. Bishop, *Mol. Cell. Biol.* 6, 4450 (1986).

Spencer, C. A., M. Groudine, *Adv. Cancer Res.* 56, 1 (1990).

Palmieri, S., P. Kahn, and T. Graf. Quail embryo fibroblasts transformed by four v-myc containing virus isolates show enhanced proliferation but are non-tumorigenic. *EMBO J.* 2:2385 (1983).

Karn, J., J. V. Watson, A. D. Lowe, S. M. Green, and W. Vedeckis. Regulation of cell cycle duration by c-myc levels. *Oncogene* 4:773 (1989).

Armelin, H. A., M. C. S. Armelin, K. Kelly, T. Stewart, P. Leder, B. H. Cochran, and C. D. Stiles. Functional role for c-myc in mitogenic response to platelet-derived growth factor. *Nature* 310:655 (1984).

Sorrentino, V., V. Drosdoff, M. D. McKinney, L. Zeitz, and E. Fleissner. Potentiation of growth factor activity by exogenous c-myc expression. *Proc. Natl. Acad. Sci.* 83:8167 (1986).

Stern, D., A. Roberts, N. S. Roche, M. B. Sporn, and R. A. Weinberg. Differential responsiveness of myc and ras-transfected cells to growth factors: Selective stimulation of myc-transfected cells by epidermal growth factors. *Mol. Cell. Biol.* 6:870 (1986).

Coppola, J. A. and M. D. Cole. Constitutive c-myc oncogene expression blocks mouse erythroleukemia cell differentiation but not commitment. *Nature* 320:760 (1989).

Langdon, W. Y., A. W. Harris, S. Cory, and J. M. Adams. The c-myc oncogene perturbs B lymphocyte development in Eu-myc transgenic mice. *Cell* 47:11 (1986).

Freytag, S. Enforces expression of the c-myc oncogene inhibits cell differentiation by precluding entry into a distinct predifferentiation state in Go/G1. *Mol. Cell. Biol.* 8:1614 (1988).

Kume, T. U., S. Takada, and M. Obinata. Probability that the commitment of murine erythroleukemia cell differentiation is determined by the c-myc level. *J. Mol. Biol.* 202:779 (1988).

Land, H., L. F. Parada, and R. A. Weinberg. Tumorigenic conversion of primary embryo fibroblasts requires at least two cooperating oncogenes. *Nature* 304:596 (1983).

Sinn, E., W. Muller, P. Pattengale, I. Tepler, R. Wallace, and P. Leder. Coexpression of MMTV/v-Ha-ras and MMTV/c-myc genes in transgenic mice: Synergistic action of oncogenes in vivo. *Cell* 49:465 (1987).

van Lohuizen, M., S. Verbeek, P. Krimpenfort, J. Domen, C. Saris, T. Radaszkiewicz, and A. Berns. Predisposition to lymphomagenesis in pim-1 transgenic mice: Cooperation with c-myc and N-myc in murine leukemia virus-induced tumors. *Cell* 56:673 (1989).

Weinberg, R. A. 1989. Oncogenes and multistep carcinogenisis (sic). In *Oncogenes and the molecular origins of cancer* (ed. R. A. Weinberg), p. 307. Cold Spring Harbor Laboratory Press, Cold Spring Harbor, New York.

(List continued on next page.)

OTHER PUBLICATIONS

DePamphilis, M. L. Transcriptional elements as components of eukaryotic origins of DNA replication. *Cell* 52:635 (1988).

Berberich, S. J. and Cole, M. D. Casein kinase II inhibits the DNA-binding activity of Max homodimers but not Myc/Max heterodimers. Genes Dev. 6, 166-176 (1992).

Berberich, S., Hyde-DeRuyscher, N., Espenshade, P., and Cole, M. D. Max encodes a sequence specific DNA binding protein and is not regulated by serum growth factors. Oncogene 4, 775-779 (1992).

Blackwood, E. M., Luscher, B. and Eisenman, R. N. Myc and Max associate in vico. Genes Dev. 6, 71-80 (1992a).

Kato, G. J., Lee, W. M. F., Chen, L., and Dang, C. V. Max: Functional domains and interaction with c-Myc. Genes Dev. 6: 81-92 (1992).

Makela, T. P., Koskinen, P. J., Vastrik, I., and Alitalo, K. Alternative forms of Max as enhancers or suppressors of Myc-Ras cotransformation. Science 256, 373-377 (1992).

Cole, M. D. Myc meets its max. Cell 65, 715-716 (1991).

Min, S., Taparowsky, E. J. v-Myc, but not Max, possesses domains that function in both transcription activation and cellular transformation. Oncogene 7, 1531-1540 (1992).

Fig. 2A.

```
CAGTGGCCGC TCCCTGGGCC GTAGGAAATG AGCGATAACG ATGACATCGA GGTGGAGAGC   60
GACGAAGAGC AACGGAGGTT TCAATCTGCG GCTGACAAAC GGGCTCATCA TAATGCACTG  120
GAACGAAAAC GTAGGACCA  CATCAAAGAC AGCTTTCACA GTTTGCGGGA CTCAGTCCCA  180
TCACTCCAAG GAGAGAAGGC ATCCCGGGCC CAAATCCTAG ACAAAGCCAC AGAGTATATC  240
CAGTATATGC GAAGGAAAAA CCACACACAC CAGCAAGATA TTGACGACCT CAAGCGGCAG  300
AATGCTCTTC TGGAGCAGCA AGTCCGTGCA CTCTACACAGC CGAGGTCAAG TGCCCAACTG  360
CAGACCAACT ACCCCTCCTC AGACAACAGC CTCTACACCA ACGCCAAGGG CAGCACCATC  420
TCTGCCTTCG ATGGGGCTC  AGACTCCAGC TCAGAGTCTG AGCCTGAAGA GCCCCAAAGC  480
AGGAAGAAGC TCCGGATGGA GCCACTCGGG GCCAGCTAA  GCCACTCCGG GCAATAAAA   537
```

Fig. 2B.

```
CAGTGGCCGC TCCCTGGGCC GTAGGAAATG AGCGATAACG ATGACATCGA GGTGGAGAGC   60
GACGCTGACA AACGGGCTCA TCATAATGCA CTGGAACGAA AACGTAGGGA CCACATCAAA  120
GACAGCTTTC ACAGTTTGCG GGACTCAGTC CCATCACTCC AAGGAGAGAA GGCATCCCGG  180
GCCCAAATCC TAGACAAAGC CACAGAGTAT ATCCAGTATA TGCGAAGGAA AAACCACACA  240
CACCAGCAAG ATATTGACGA CCTCAAGCGG CAGAATGCTC TTCTGGAGCA GCAAGTCCGT  300
GCACTGGAGA AGGCGAGGTC AAGTGCCCAA ACTACCCCTC CTCAGACAAC CTCAGACAAC  360
AGCCTCTACA CCAACGCCAA AGTGCCCAA  ATCTCTGCCT TCGATGGGGG AGCTCCAGCT  420
AGCTCAGAGT CTGAGCCTGA AGAGCCCCAA AGCAGGAAGA AGCTCCGGAT GGAGGCCAGC  480
TAAGCCACTC GGGGCCAGCC AGCAATAAAA                                   510
```

FIG. 2C.

| Met | Ser | Asp | Asn | Asp | Asp | Ile | Glu | Val | Glu |
|-----|-----|-----|-----|-----|-----|-----|-----|-----|-----|
| Ser | Asp | Glu | Gln | Pro | Gln | Pro | Phe | Gln | Ser |
| Ala | Ala | Asp | Lys | Arg | Ala | His | Asn | Ala |  |
| Leu | Glu | Arg | Lys | Arg | Arg | His | Ile | Lys |  |
| Asp | Ser | Phe | His | Ser | Leu | Arg | Asp | Ser | Val |
| Pro | Ser | Leu | Gln | Gly | Lys | Glu | Lys | Ala | Ser | Arg |
| Ala | Gln | Ile | Leu | Asp | Lys | Ala | Thr | Glu | Tyr |
| Ile | Gln | Tyr | Met | Arg | Arg | Lys | Asn | His | Thr |
| His | Gln | Asp | Ile | Asp | Asp | Leu | Lys | Arg |  |
| Gln | Asn | Ala | Leu | Leu | Glu | Gln | Gln | Val | Arg |
| Ala | Leu | Glu | Lys | Ala | Arg | Ser | Ser | Ala | Gln |
| Leu | Gln | Thr | Asn | Tyr | Pro | Ser | Ser | Asp | Asn |
| Ser | Leu | Tyr | Thr | Ala | Lys | Gly | Ser | Thr |  |
| Ile | Ser | Ala | Phe | Asp | Gly | Gly | Ser | Asp | Ser |
| Ser | Ser | Glu | Ser | Glu | Pro | Glu | Pro | Gln |  |
| Ser | Arg | Lys | Leu | Arg | Met | Glu | Ala | Ser |  |

```
Met Ser Asp Asn Asp Ile Glu Val Glu
Ser Asp Ala Asp Lys Arg Ala His Asn
Ala Leu Glu Arg Lys Arg Arg Asp His Ile
Lys Asp Ser Phe His Ser Leu Arg Asp Ser
Val Pro Ser Leu Gln Gly Gly Glu Lys Ala Ser
Arg Ala Gln Ile Leu Asp Lys Ala Thr Glu
Tyr Ile Gln Leu Tyr Met Arg Arg Lys Asn His
Thr His Gln Asp Ile Asp Asn Lys Leu Lys
Arg Gln Asn Ala Leu Leu Glu Asp Gln Gln Leu Val
Arg Ala Leu Glu Lys Ala Arg Ser Ser Ala
Gln Leu Gln Thr Asn Tyr Pro Ser Ser Asp
Asn Ser Leu Tyr Thr Asn Ala Lys Gly Ser
Thr Ile Ser Ala Phe Asp Gly Gly Ser Asp
Ser Ser Ser Glu Glu Ser Glu Pro Glu Pro
Ser Ser Arg Lys Ser Lys Ser Lys Gly Pro Glu Pro
Gln Ser Arg Lys Ser Lys Ser Lys Leu Arg Met Glu
Ala Ser
```

Fig. 2D.

```
Max     DKRAHHNALERKRRDHIKDSFHSLRDSVP-------SLQG------QKAS
c-Myc   VKRRTHNVLERQRRNELKRSFFALRDQIP------ELEN------NEKAP
N-Myc   ERRRNHNILERQRRNDLRSSFLTLRDHVP------ELVK------NEKAA
L-Myc   TKRKNHNFLERKRRNDLRSRFLALRDQVP------TLAS------CSKAP
Myo-D1  DRRKAATMRERRRLSKVNEAFETLKRCTSSNP-----------NQRLP
E12     ERRVANNARERLRVRDINEAFKELGRMCQLHNSEKP-----------QT
As-C    QRR---NARERNRVKQVNNSFARLRQHIPQSIITDLTKGGGRGPHKKIS
Lc      TGTKNHVMSERKRREKLNEMFLVLKSLLPSIHR-----------VN
CBF-1   QRKDSHKEVERRRRENINTAINVLSDLIT-------VR------E-SS
AP-4    IRREIANSNERRRMQSINAGFQSLKTLIP-------HTDG------EKLS
USF     KRRAQHNEVERRRRDKINNNIVQLSKIIP-----DCSMESTKSGQS----
Cons.    RR      RER R    ΦN    Ω   LK     Φ                  K
         KK       ΦK     K        R     T                  R
                   R                    C
         ///////////////[=========]
         Basic Region    Helix I      Loop
```

Fig. 3A.

```
Max    RAQILDKATEYIQYMRRKNHTHQQDIDDLKRQNALLEQQVRAL
c-Myc  KVVILKKATAYILSVQAEEQKLISEEDLLRKRREQLKHKLEQL
N-Myc  KVVILKKATEYVHSLQAEEHQLLLEKEKLQARQQLLKKIEHA
L-Myc  KVVILSKALEYLQALVGAEKRMATEKRQLRCRQQQLQKRIAYL
Myo-D1 KVEILRNAIRYIEGLQALLR
E12    KLLILHQAVSVILNLEQQVR
As-C   KVDTLRIAVEYIRSLQDLVD
Lc     KASILAETIAYLKELQRRVQ
CBF-1  KAAILARAAEYIQKLKETDE
AP-4   KAAILQQTAEYIFSLEQEKTRLLQQNTQLKRFIQEL
USF    KGGILSKACDYIQELRQSNHQLQLDNDVLRQQVEDLKNKNLLL
                                    RLSEELQGLD

Cons.  K  ΦL AΦ YΦ   Φ
          T  TT
       ================ == ==   +++++++++++++++++++++
            Helix II             Zipper
```

Fig. 3B.

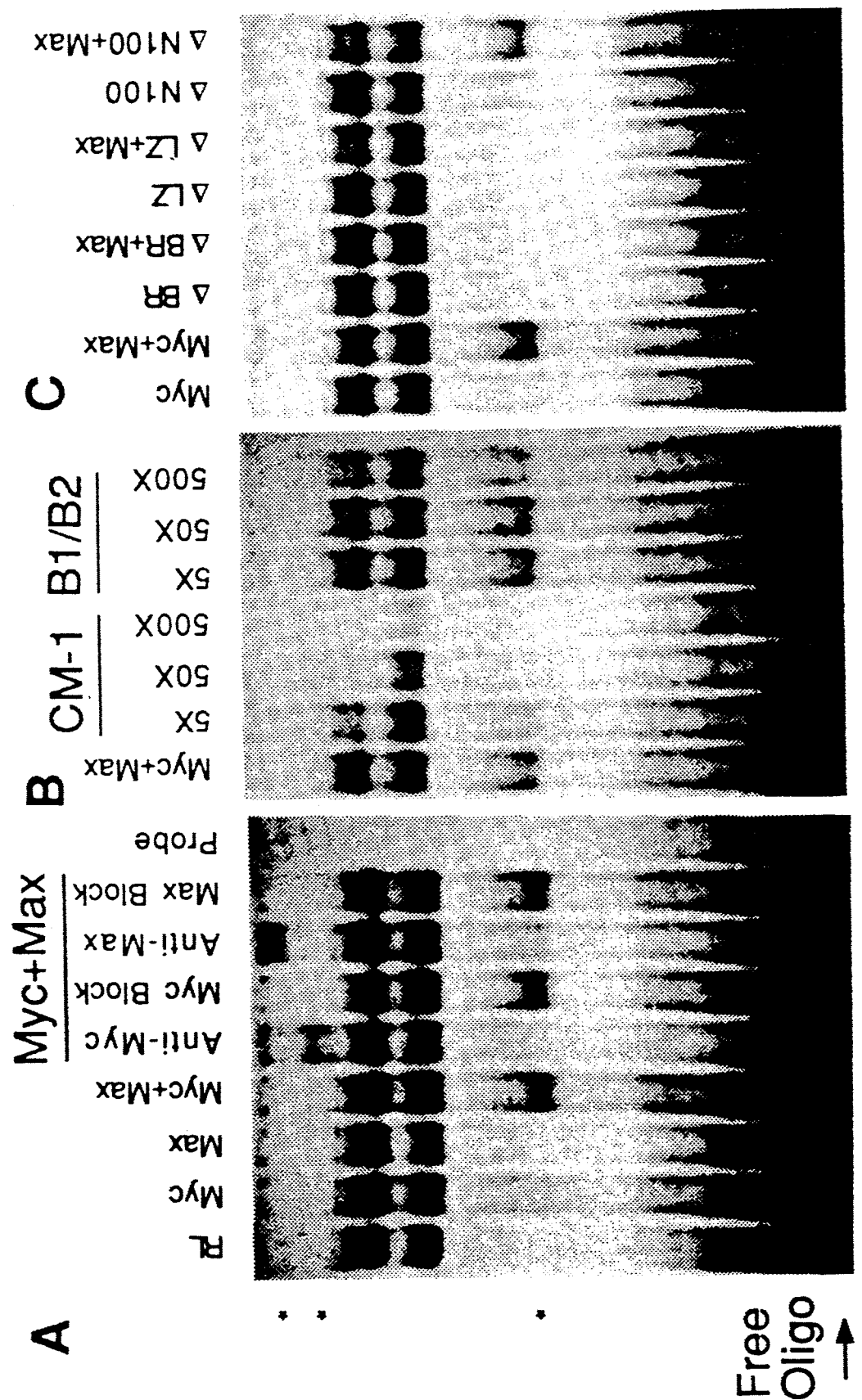

Manca

Fig. 8D.

IVT+Manca

Chromatography ←

Electrophoresis pH 1.9

α-MAX
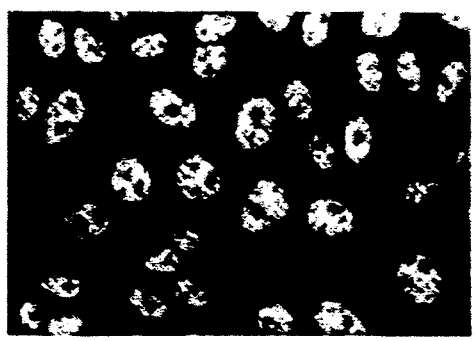 
Fig. 9A.  Fig. 9B.
Max block
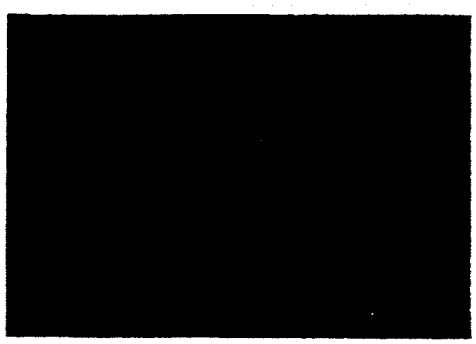 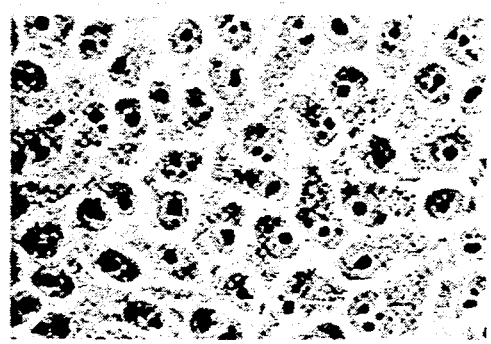
Fig. 9C.  Fig. 9D.
α-Myc
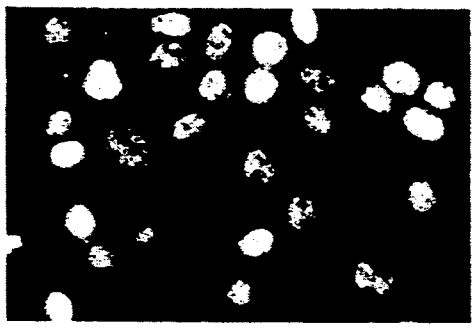 
Fig. 9E.  Fig. 9F.
Prei α-Myc
 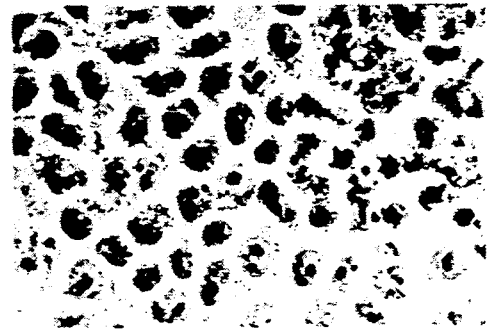
Fig. 9G.  Fig. 9H.

Max mRNA

Max protein

```
1
   CGC CAG AGA GGC TCC CTC AGC CCT GCT CCG CGG GGT CCA CAG CGG GCT
61
   CCA TAG CGG GCT CCA CAG CGG TCC GGC GGC AGC GAG CCC GTG GGC AGT GGG GGT TGG
       AMB
121
   TCC CGT GGC TCC GGC CCC CGG TGC AGA ATG GCG GCG GTT CGG ATG AAC ATC CAG ATG
                                         met ala ala val arg met asn ile gln met
                                          1
181/12
   CTG CTG GAG GCG GCC GAC TAT CTG GAG CGG CGG GAG AGA GAA GCT GAA CAT GGT TAT GCC
   leu leu glu ala ala asp tyr leu glu arg arg glu arg glu ala glu his gly tyr ala
241/32
   TCC ATG TTA CCA TAC AAT AAC AAG GAC AGA GAT GCC TTA AAA CGG AGG AAC AAA TCC AAA
   ser met leu pro tyr asn asn lys asp arg asp ala leu lys arg arg asn lys ser lys
301/52
   AAG AAT AAC AGC AGT AGC AGA TCA ACT CAC AAT GAA ATG GAG AAG AAT AGA CGG GCT CAT ala his
   lys asn asn ser ser ser arg ser thr his asn glu met glu lys asn arg arg ala his
361/72
   CTT CGC TTG TGC CTG GAG AAG TTG AAG GGG CTG GTG CCA CTG GGA CCC GAA TCA AGT CGA arg
   leu arg leu cys leu glu lys leu lys gly leu val pro leu gly pro glu ser ser arg
421/92
   CAC ACT ACG TTG AGT TTA TTA ACA AAA GCC AAA TTG CAC ATA AAG AAA CTT GAA GAT TGT
   his thr thr leu ser leu leu thr lys ala lys leu his ile lys lys leu glu asp cys
481/112
   GAC AGA AAA GCC GTT CAC CAA ATC GAC CAG CTT CAG CGA GAG CAG CAC CTG AAG AGG
   asp arg lys ala val his gln ile asp gln leu gln arg glu gln his leu lys arg
```

Fig.14A.

```
541/132
CAG CTG GAG AAG CTG GGC ATT GAG AGG ATC CGG ATG GAC AGC ATC GGC TCC ACC GTC TCC
gln leu glu lys leu gly ile glu arg ile arg met asp ser ile gly ser thr val ser
601/152
TCG GAG CGC TCC GAC AGG GAA GAA ATC GAC GTT GAC GTG GAG AGC ACG GAC TAT
ser glu arg ser asp arg glu glu ile asp val asp val glu ser thr asp tyr
661/172
CTC ACA GGT GAT CTG GAC TGG AGC AGC GAC TCT GAC GAG CGG GGC AGC
leu thr gly asp leu asp trp ser ser asp ser asp glu arg gly ser
721/192
ATG CAG AGC CTC GGC AGT GAT GAG GGC TAT TCC AGC ACC AGC ATC AAG AGA ATA AAG CTG
met gln ser leu gly ser asp glu gly tyr ser ser thr ser ile lys arg ile lys leu
781/212                                       221
CAG GAC AGT CAC AAG GCG TGT CTT GGT CTC TAA GAG AGT GGG CAC TGC GGC TGT CTC CTT
gln asp ser his lys ala cys leu gly leu OCH
841
GAA GGT TCT CCC TGT TGG TTC TGA TTA GGT AAC GTA TTG GAC CTG CCC ACA ACT CCC TTG
                                    OPA
901
CAC GTA AAC TTC AGT GTC CCA CCT TGA CCA AAA TCA GCT TTG TAA CTG TTT TCA AGG AGG
                                OPA                             OCH
961
TGC TTA GGA TTG TGG GTT TCT GAT TGC ATC ACT AGC TTC TCC.........
```

*Fig. 14B.*

```
Mad-1   SSRSTHNEMEKNRRAHLRLCLEKLKGLVP----LGPESS----
Max     DKRAHHNALERKRRDHIKDSFHSLRDSVP----SLQG-----Q
c-Myc   VKRRTHNVLERQRRNELKRSFFALRDQIP----ELEN---NE
EMC     IQRHPTVDDPMSLLYNMDCYSKLKELVP----FMP---KNR
Hairy   DRRSNKPIMEKRRRARINNCLNELKTLIL-DATKKDPA-RHS
TFE     QKKDNHNLIERRRFNINDRIKELGTLIP----KSSDP--QM
USF     KRRAQHNEVERRRDKINNNIVQLSKIIP-DCSMESTKSGQS
Cons.    RR      RER R    ΦN  ψ  LR     Φ
         KK      Φ R       R       K  T
                           K           C
```

Φ=L,I,V,M
ψ=F,L,I,Y

Basic Region | Helix I | Loop

Fig. 15A.

```
Mad-1   RHTTLSLLTKAKLHIKKLEDCDRKAVHQIDQLQREQRHLKRQLEKLGIERIRMDSIGSTV
Max     KASRAQILDKATEYIQYMRRKNHTHQQDIDDLKRQNALLEQQVRAL
c-Myc   KAPKVVILKKATAYILSVQAEEQKLISEEDLLRKRREQLKHKLEQL
EMC     KLTKLEIIQHVIDYICDLQTE
Hairy   KLEKADILEKTVKHLQELQRQ
TFE3    RWNKGTILKASVDYIRKLQKE----QQRSKDLESRQRSLEQANRSLQLRIQEL
USF     ---KGGILSKACDYIEQLRQSNHRLSEELQGLDQLQLDNDVLRQQVEDLKKKNLLL Cons.   R   K   ΦL  AΦ  YΦ  Φ
        K       T       TT
Φ=L,I,V,M
        ================+++++++++++++++++++++++++++++++
        Helix II                Zipper
```

Fig.15B.

METHOD OF PRODUCING A MAD POLYPEPTIDE

This invention was made with government support under grants T32CA09437, RO1 CA20525, PO1 CA28151 and CA57138 awarded by the National Institutes of Health. The government has certain rights in the invention.

This application is a continuation-in-part of application Ser. No. 07/756,195, filed Sep. 9, 1991, now abandoned.

FIELD OF THE INVENTION

This invention relates generally to genetic engineering involving recombinant DNA technology, and particularly to the identification of a bHLP-Zip polypeptide, termed Max, that specifically associates with c-Myc polypeptides such that the Myc-Max complex binds to DNA in a sequence specific manner, and a polypeptide termed Mad, that specifically associated with Max and is a competitive inhibitor of Myc binding to Max.

BACKGROUND OF THE INVENTION

The products of the MYC family of protooncogenes, including c-Myc, N-Myc, and L-Myc proteins, function in cell proliferation, differentiation, and neoplastic disease (1; see the appended Citations). However, there is as yet no consensus as to the molecular mechanism by which Myc mediates its biological effects. The Myc proteins are nuclear phosphoproteins with short half-lives and nonspecific DNA-binding activities (2). Functionally important regions exist as both the amino and carboxyl termini of the c-Myc protein (3-5). Indeed, the carboxyl-terminal 85 amino acids of the Myc family proteins share significant sequence similarity with two classes of transcription factors, the basic region helix-loop-helix (bHLH) and basic region leucine zipper (bZip) proteins, both of which have basic regions adjacent to their dimerization domains. The bHLH family includes over 60 proteins in vertebrates, yeast, plants, and insects; many, if not all, exhibit nuclear localization, are sequence-specific DNA-binding proteins, and function as transcriptional regulators(6). The region of sequence similarity shared to Myc and other proteins in this class is a critical determinant of function and contains a stretch of basic amino acids followed by two putative amphipathic a helices that flank an W-type loop (7,8). Studies of several other bHLH proteins have demonstrated that the HLH region mediates formation of homo- or heterodimers, which in turn permits the basic regions to form a DNA contact surface (9-11). Myc family proteins differ from the bHLH family in that adjacent and carboxyl-terminal to their bHLH motif is another a helix that contains a heptad repeat of leucine residues. This structure is characteristic of the dimerization domains of the bZip family of transcriptional regulators (12). The array of nonpolar amino acids forms a hydrophobic face long the amphipathic helic, facilitating specific association of bZip proteins through a parallel coiled-coil interaction (13). Dimerization is critical for DNA binding (14, 15).

For c-Myc there is substantial evidence that the bHLH region and the adjacent leucine zipper motif are functionally important. Deletions within these regions result in loss of alteration of transforming activity (3, 16) as well as reduction of the capacity of autoregulate endogenous myc expression and to inhibit cell differentiation (4, 5). In addition, a bacterially expressed fusion protein that contains the bHLH-Zip domains of c-Myc has sequence-specific DNA-binding activity (17).

It is also of interest to consider the myc oncogene in the context of tumor suppressor genes since, at least on theoretical grounds, it is precisely the proliferation-inducing effects of myc that one would expect to be opposed by genes of the tumor suppressor class. The notion that myc oncogene function is linked to cell proliferation is now supported by multiple lines of evidence. Much of this evidence has been summarized in recent reviews (18,19) and will be briefly reiterated here. First, c-myc expression is strongly correlated with cell growth. During exponential growth of many different cell types, c-myc-encoded mRNA and protein synthesis is maintained at a constant level throughout the cell cycle (20,21). By contrast, c-myc expression is essentially undetectable in quiescent ($G_0$) cells and in most, but not all, terminally differentiated cell types. The down-regulation of c-myc expression during differentiation is likely to be a critical event since forced expression of exogenous c-myc blocks the induced differentiation of erythroleukemia cells and adipocytes (22, 23) while anti-sense inhibition of c-myc expression in HL60 cells leads directly to differentiation (24).

On the other hand, the entry into the cell cycle of quiescent cells is invariably accompanied by a large transient burst of c-myc expression within hours of mitogenic stimulation of both hematopoietic and non-hematopoietic cell types (25). Indeed, c-myc is prototypical of the class of immediate early response genes encoding labile mRNAs which can be induced (or superinduced) in the presence of protein synthesis inhibitors. That myc expression is important for entry into the cell cycle is suggested by experiments utilizing c-myc anti-sense oligonucletides, which appear to block the entry of mitogenically stimulated human T cells into S phase but not into the $G_1$ phase of the cell cycle (26). Recent experiments using an artificially "activatable" c-myc-encoded protein (c-Myc) have demonstrated that quiescent fibroblasts can be made to enter the cell cycle following activation of c-Myc. Amazingly, this occurs in the absence of the induction of the other major early response genes, including jun and fos (27). Thus, c-myc expression may be sufficient for entry of $G_0$ cells into the cell cycle.

Further support for the idea that Myc function is strongly linked to cell proliferation and differentiation comes from the vast amount of data demonstrating an association between the deregulation of myc family gene expression and neoplasia (for reviews, see 28-30). Oncogenic activation of myc by retroviral capture, promoter/enhancer insertion, gene amplification, and chromosomal translocations all appear to lead to abnormal and uncontrolled proliferation of numerous cell types. While these events frequency result in myc overexpression, they also result in a loss of the normal regulatory elements that control normal myc expression. A great deal of work has demonstrated that myc expression is normally regulated at multiple levels (for recent review, see 31), and it is the loss of such regulation which is believed to result in uncontrolled cell proliferation and a reduced capacity for terminal differentiation.

Although it is indisputable that Myc is involved in cell proliferation, it is less clear whether the functions of tumor suppressor genes, which are often through to act as negative growth regulators (see 32 for review), actually impinge directly on Myc function. One potential example of interaction between myc function and tumor suppressor gene activity has come from studies demonstrating that treatment of an epithelial cell line with TGF-$\beta$ results in transcriptional repression of c-myc which is reversible by agents (adenovirus E1A, SV40 R antigen) that sequester the Rb gene product (33,34). While these data do not necessarily indicate a direct interaction between Myc and Rb they at least hint at the possibility that the functional pathways of these two gene products may be intertwined. In addition, it is possible that Myc might interact directly with an as yet uncharacterized tumor suppressor protein. It is clear that more details concerning the molecular mechanism of Myc function are required in order to explore more fully the possibility of direct interaction between Myc and tumor suppressor gene products. One approach is to define the interactions of Myc protein with other cellular proteins, as well as with nucleic acids. Such studies may help to elucidate Myc's molecular function and reveal the circuitry through which proliferation suppression factors may interact with Myc.

The biological importance of and structural similarities in the carboxyl terminus of c-Myc suggest that Myc functions as a component of an oligomeric complex. While Myc self-association has been demonstrated with relatively high concentrations of bacterially expressed Myc protein (35), coprecipitation, chemical crosslinking, and dimerization motif chimeras fail to demonstrate homodimerization of Myc under physiological conditions (1, 36, 37). Because functionally relevant interactions occur among members of the bHLH and bZip classes (9, 15, 38, 39), and c-Myc has not yet been found to associate with members of either group (10, 15, 16), we hypothesized that Myc function may depend on heterotypic interaction with an unknown protein. We now describe the cloning of such a Myc binding factor, termed Max, and its regulatory factor, termed Mad.

SUMMARY OF THE INVENTION

The invention provides isolated nucleic acid molecules capable of hybridizing under stringent conditions to the nucleotide sequence residing between positions 1 and 453 of the max cDNA shown in FIGS. 2A–B, and the nucleotide sequence residing between positions 1 and 1002 of the mad cDNA shown in FIG. 14. In the preferred embodiment, such isolated nucleic acid molecules encode Max polypeptides that specifically associate with Myc polypeptides, and Mad polypeptides that associate with Max, respectively. Such a Max polypeptide, either alone (homodimerized) or when associated with the Myc polypeptide, is capable of binding to a nucleotide sequence containing CACGTG as an activation complex. Max associated with Mad is also capable of binding CACGTG, but as a repressor complex. In a related embodiment, such isolated nucleic acid molecules encode polypeptides that are recognized by antibodies that bind to the Max polypeptide shown in FIGS. 2C–D, and the Mad polypeptide shown in FIGS. 14A–B.

The subject nucleic acid molecule can be operably linked to suitable control sequences in recombinant expression vectors. The recombinant expression vectors are used to transfect or transduce cells, such that the engineered cells produce a Max polypeptide that specifically associates with a Myc polypeptide, or a Mad polypeptide that associates with Max. Polypeptides so produced are generally characterized as encoded by a gene sequence capable of hybridizing under stringent conditions to the nucleotide sequence residing between positions 1 and 43 of the max cDNA shown in FIGS. 2A–B, or residing between positions 148 and 810 of the mad cDNA shown in FIGS. 14A–B.

The invention also provides isolated polypeptide Max:Myc complexes, in which a Max polypeptide is associated with a Myc polypeptides, and Mad:Max complexes, in which Max is associated with Mad. The Myc polypeptide may be encoded by the c-myc, L-myc, N-myc, or v-myc protooncogenes. Such isolated polypeptide Max:Myc or Mad:Max complexes are capable of binding to the nucleotide sequence CACGTG.

The invention also provides isolated DNA molecules capable of hybridizing under stringent conditions to: the nucleotide sequence residing between positions 88 and 123 of the helix 1 region of the max cDNA shown in FIGS. 2A–B; the nucleotide sequence residing between positions 142 and 186 of the helix 2 region of the max cDNA shown in FIGS. 2A–B; the basic region sequence residing between positions 43 and 81 of the max cDNA shown in FIGS. 2A–B; and, the leucine zipper region residing between position 210 and 270 shown in FIGS. 2A–B. Also provided are isolated DNA molecules encoding polypeptides that can specifically associated with Myc polypeptides but that do not bind to the nucleotide sequence CACGTG; such mutant DNA molecules are capable of hybridizing to the nucleotide sequence residing between positions 82 and 453 shown in FIGS. 2A–B, but not to the basic region residing between positions 43 and 81 shown in FIGS. 2A–B.

The invention also provides isolated DNA molecules capable of hybridizing under stringent conditions to: the nucleotide sequence residing between positions 355 and 399 of the helix I region of the mad cDNA shown in FIGS. 14A–B; the nucleotide sequence residing between positions 418 and 471 of the helix II region of the mad cDNA shown in FIGS. 14A–B, the basic region sequence residing between positions 319 and 354 of the mad cDNA shown in FIGS. 14A–B; and, the heptad hydrophobic zipper region sequences residing between positions 472 and 597 of the mad cDNA shown in FIGS. 14A–B. Also provided are isolated DNA molecules encoding mutant Mad polypeptides, that can specifically associate with Max polypeptides at a higher affinity that a non-mutant Mad, and mutant Mad polypeptides can competitively inhibit Myc binding to Max more at a lower concentration than non-mutant Mad polypeptides. Other isolated DNA molecules are provided that encode mutant Mad polypeptides that have binding affinity for Max, but when in complex with Max may fail to bind to the nucleotide sequence CACGTG, i.e., mutant in the DNA binding site domain contributed to the complex by Mad. In one example, the mutant Mad polypeptides are encoded by DNA molecules that are hybridizing to the nucleotide sequence residing between positions 148 and 810 shown in FIGS. 14A–B but not to the basic region residing between positions 319 and 354 shown in FIGS. 14A–B.

BRIEF DESCRIPTION OF THE DRAWINGS

FIGS. 2A-D present the nucleotide and amino acid sequences of Max and the organization of Max cDNA, as described in Example 2;

FIGS. 3A-B diagrammatically delineate and compare the amino acid sequences of the HLH region and basic zipper (bZip) regions of the Myc and Max poly peptides, as discussed in Example 2;

FIG. 4B illustrates structural requirements in Myc for formation of the Myc:Max complex utilizing altered forms of Myc, as described in Example 3; and FIG. 4C presents the results of control experiments showing the specificity of the Myc:Max interaction, as described in Example 3;

FIG. 7A shows the binding of the isolated purified Myc:Max complex to the core consensus nucleotide sequence CACGTG, as described in Example 4;

FIG. 7B illustrates the specificity of the binding of isolated purified Myc:Max complex to the core consensus nucleotide sequence, as described in Example 4;

FIG. 7C delineates the protein structural requirements for binding of the Myc:Max complex to the core consensus nucleotide sequence, as described in Example 4;

FIGS. 8B-E show the two-dimensional peptide maps of radiolabeled Max p21 and Max p22 polypeptides, as described in Example 5;

FIGS. 9A-H show detection and localization of Max in mammalian cells by immunofluororescence assays, as described in Example 5;

FIG. 13A shows an autoradiograms of an a gel in which decreased electrophoretic mobility of Max:Max:oligonucleotide complexes was observed in the presence of antibodies to max($\alpha$max). Max binding to DNA was assayed in the absence ("-") or the presence of a Max-specific anti-peptide antiserum. "$\alpha$Max+block" indicates the inclusion of both $\alpha$Max and the immunizing peptide in the Max/oligonucleotide binding reaction.

FIG. 13B shows an autoradiogram of a gel in which the electrophoretic mobility of Max:Max homodimeric complexes with CM-1 oligonucleotide (or an unrelated MREA oligonucleotide) was assayed. Levels of Max:Max complexes were assayed in the presence of unlabeled CM-1 or MREA. The levels of Max:Max were unchanged as the amount of MREA was increased from 25 ng to 100 ng in the assay, but when CM-1 was increased from 25 ng to 100 ng the levels of Max:Max complexes decreased. (The amount of competing oligonucleotide is given in ng in the box at the top of each lane of the gel. "-" denotes no unlabeled oligonucleotide in the binding reaction.) The position of the free probe and the Max homodimer mobility shift is as marked. The Max:Max* asterisk denotes the electrophoretic mobility of the antibody:Max:Max complex.

FIG. 13C shows an autoradiogram of $^{32}$P-labeled Max binding to a filter containing phage lysates from different gt11 lambda clones. Clone Max 14 was identified in the FIREST SERIES OF EXAMPLES as being a binding partner for Myc. $\lambda$1 encoded a lacZ fusion protein with no specific Max binding activity and served as a negative control in this experiment. $\lambda$10, 11, and 26 encoded lacZ fused to potential Max binding partners.

FIGS. 14A-B shows the nucleotide (Seq. ID No.: 5) sequence of human Mad-1 cDNA and the amino acid sequence (Seq. ID No.: 6) encoded thereby. (The nucleotide and the amino acid sequence of the coding ration of the 3.2 kb human Mad-1 cDNA from the WI26 gt10 library is shown.) Nucleotide positions are indicated. Amino acid positions are denoted by bold faced numbers and in frame stop codons are shown. The basic region homology is boxed and the positions of the positively charged residues in this region are marked by "+". The shaded boxes locate helix I and helix II. The amino acids that form the hydrophobic heptad repeat (i.e., positions 108 to 150) are given in bold underlined text. The region rich in acidic amino acids is located between amino acids 152 and 189.

FIGS. 15A-B show a comparison of the amino acid sequence of Mad-1 with other b-HLH proteins.

FIGS. 15A-B show the predicted amino acid sequence of Mad-1 as it compares with other members of the b-HLH family of transcription factors and to the b-HLH consensus sequence ("Cons."). The amino acids are denoted by the single letter code. The Drosophila proteins EMC (extramacrocheatae) and hairy were found to be most similar to Mad-1 in searches of the data base while TFE3 and USF both recognize the same DNA binding site (CACGTG) as Myc and Max. The matches to the b-HLH consensus are shaded and the residues that form a heptad repeat of hydrophobic amino acids are shaded and boxed. The shaded and cross-hatched bar at the bottom of FIG. 15A depicts a generalized organizational structure for a b-HLH-zipper protein.

In FIG. 16B the arrows mark the position of either the ABR Max or Max9 or ALZ Max polypeptide. The position of molecular weight markers (in kD) are given at the right of each panel.

FIG. 20A shows an autoradiogram of Max:Max, Myc:Max and Mad:Max binding to DNA. The results show similar binding affinities of Myc:Max and Mad:-Max for the CM-1 DNA probe. (The DNA binding characteristics of the purified histidine tagged Mad was assayed FIG. 20A).

FIG. 20B shows an autoradiogram of Myc:Max binding to DNA as a function of increasing concentrations of Mad in the binding reaction. (At a constant amount of GST-C92Myc:Max (6 ng:2 ng) increasing amounts of Mad were added to the incubation mixture, (right arrow), in 2 fold increments starting at 1.8 ng and ending at 30 ng.)

FIG. 20C shows an autoradiogram of Mad:Max binding to DNA as a function of increasing concentrations of Myc in the binding reaction. (At a constant amount of Mad:Max (7.5 ng:2 ng) increasing amounts of GST-C92Myc were added to the incubation mixture, (right arrow) in 2 fold increments starting from 1.6 ng and ending at 50 ng.)

DETAILED DESCRIPTION OF THE PREFERRED EMBODIMENT

Figure 1A:
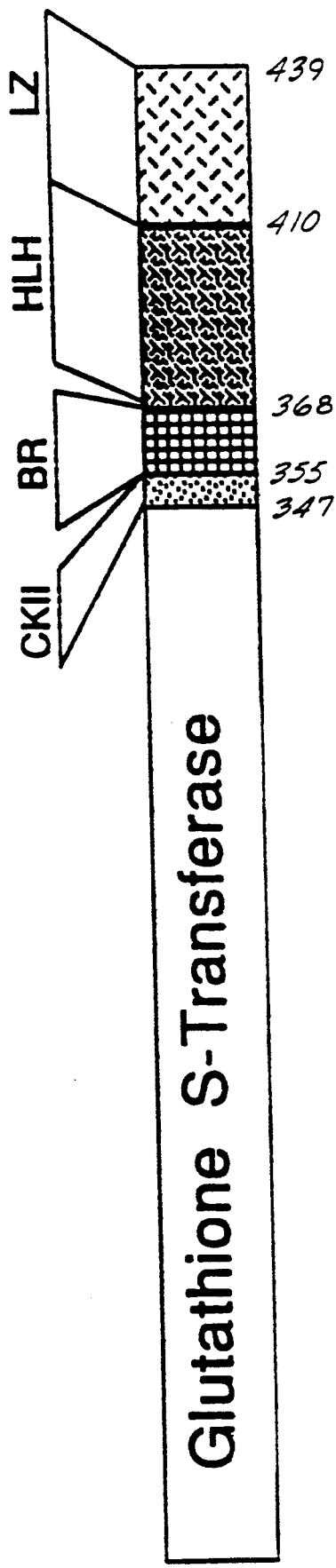
FIG. 1A diagrammatically represents the Myc fusion protein used to screen for Max, as described in Example 1.

The Myc protooncogene family has been implicated in cell proliferation, differentiation, and neoplasia, but its mechanism of function at the molecular level has been unknown. The carboxyl terminus of Myc family proteins contains a basic region helix-loop-helix leucine zipper motif (bHLH-Zip), which has DNA-binding activity and has been predicted to mediate protein-protein interactions. As described in the First Series of Examples below, the bHLH-Zip region of c-Myc was used to screen a complementary DNA (cDNA) expression library, and a bHLH-Zip protein, termed Max, was identified. Max specifically associated with c-Myc, N-Myc, and L-Myc proteins, but not with a number of other bHLH, bZip, or bHLH-Zip proteins. The interaction between Max and c-Myc was dependent on the integrity of the c-Myc HLH-Zip domain, but not on the basic region or other sequences outside the domain. Furthermore, the Myc-Max complex bound to DNA in a sequence-specific manner under conditions where neither Max nor Myc exhibited appreciable binding. The DNA-binding activity of the complex was dependent on both the dimerization domain and the basic region of c-Myc. These results suggest that Myc family proteins undergo a restricted set of interactions in the cell and may belong to the more general class of eukaryotic DNA-binding transcription factors.

Mad associates specifically with Max, but not with Myc or other b-HLH transcription regulatory factors. Mad may be a competitor protein associating with Max and forming a negative regulatory complex termed Mad:Max. The levels of Mad, Max, and/or Myc may determine activation or repression of genes regulated by transcription regulatory factors binding at the CACGTG motif in DNA.

As described in the Second Series of Examples below, Myc and Max are associated in vivo, and essentially all of the newly synthesized Myc can be detected in a complex with Max. The stability of Myc protein is unchanged by its association with Max. In vivo, Max is shown to be a highly stable nuclear phosphoprotein whose levels of expression are equivalent in quiescent, mitogen-stimulated, and cycling cells. The rate of Myc biosynthesis is therefore likely to be a limiting step in the formation of Myc:Max complexes.

As described in the Third Series of Examples below, addition of Mad to preformed Max:Myc complexes causes dissociation of the complex with formation of Mad:Max complexes, similarly, addition of Myc to Mad:Max complexes causes dissociation and formation of Max:Myc.

The invention provides, in a representative embodiment, an isolated nucleic acid molecule (DNA or RNA) that is capable of hybridizing under stringent conditions to the nucleotide sequence residing between positions 1 and 453 of the max cDNA shown in FIGS. 2A-B. By "capable of hybridizing under stringent conditions" is meant annealing to a cDNA shown in FIGS. 2A-B (i.e., with or without the 27-mer insertion shown between base positions 36 and 37), or its complementary strand, under standard conditions, e.g., high temperature and/or low salt content, which tend to disfavor hybridization. A suitable protocol (involving 0.1×SSC, 68° C. for 2 hours) is described in Maniatis, T., et al., Molecular Cloning: A Laboratory Manual, Cold Spring Harbor Laboratory, 1982, at pages 387-389. The nucleic acid so annealed may be one of the two max cDNAs shown in FIGS. 2A-B, portions thereof, or of any other alternatively spliced forms or max-related cDNAs and genes.

The subject nucleic acid molecule preferably encodes a Max polypeptide that can associate with a Myc polypeptide. The Max polypeptide when associated with the Myc polypeptide is capable of binding to the nucleotide sequence CACGTG.

The subject Max polypeptides are produced by operably linking the isolated nucleic acid molecule to suitable control sequences in recombinant expression vectors. Cells transfected or transduced with such recombinant expression vectors are capable of expressing the encoded polypeptides. Such polypeptides are generally encoded by a gene sequence capable of hybridizing under stringent conditions to the nucleotide sequence(s) residing between positions 1 and 453 of the max cDNA shown in FIGS. 2A-B. Such polypeptides preferably also associate with Myc polypeptides.

In a related embodiment, the invention provides an isolated polypeptide Max:Myc complex in which a Max polypeptide is associated with a Myc polypeptide. The Myc polypeptide may be encoded by the c-myc, L-myc, N-myc, or v-myc protooncogenes. The isolated polypeptide Max:Myc complex is generally capable of binding to the nucleotide sequence CACGTG.

In related embodiments, the invention provides isolated DNA molecules capable of hybridizing under stringent conditions to the nucleotide sequence residing between positions 88 and 123 of the helix 1 region of the max cDNA shown in FIGS. 2A-B; the nucleotide sequence residing between positions 142 and 186 of the helix 2 region of the max cDNA shown in FIGS. 2A-B; the basic region sequence residing between positions 43 and 81 of the max cDNA shown in FIGS. 2A-B; and, the leucine zipper region residing between position 210 and 270 shown in FIGS. 2A-B. Mutant DNA molecules are also provided. In a representative example, the mutant DNA molecule encodes a polypeptide that can specifically associate with a Myc polypeptide but that does not bind to the nucleotide sequence CACGTG; this particular mutant DNA molecule is capable of hybridizing to the nucleotide sequence residing between positions 82 and 453 shown in FIGS. 2A-B but not to the basic region residing between positions 43 and 81 shown in FIGS. 2A-B.

In addition to its evident value as a research reagent, the following potential uses relating to Max are contemplated:

1. Changes in the levels of Max and especially of the Myc:Max complex as a diagnostic or prognostic tool for diverse types of cancer. This might involve standard protocols using a reagent, such as a monclonal antibody, which recognizes the Myc:Max complex but not Myc or Max alone (or homodimerized). The max gene resides on chromosome 14 q22-24 (unpublished), and changes in this region might be implicated in neoplasia.

2. Interference with formation or maintenance of the Myc:Max complex as a means of retarding neoplasia. This might occur through specific antibodies (following cellular uptake) or with chemical reagents (such as specific peptides or drugs) which interfere with interaction between the helix-loop-helix-zipper domains of the two proteins. Design of such reagents may entail knowledge of the three-dimensional structure of both Myc and Max and the complex(es). Studies using NMR and X-ray crystallography are contemplated.

3. A "dominant negative Max" which is capable of forming a complex with Myc but is nonfunctional might be used to influence neoplasia. One such Max has a deletion or substitution of the Max basic region involved in DNA binding.

4. If Max itself is a negative regulator of cell growth then increasing the levels of Max through different vectors might phenotypically oppose an increase in Myc levels. Likewise, decreasing Max levels, e.g., through anti-sense vectors, might also influence cell growth.

5. Max appears to be expressed throughout embryonic development (M. W. King, unpublished), and therefore alterations in Max levels might influence key events in embryogenesis.

6. The Max:Myc, Max:Max, and possibly Myc:Myc complexes are likely to bind DNA sequences that are involved in regulation of transcription and/or DNA replication. In either case Myc and Max may regulate genes that themselves are involved in DNA replication and cell proliferation. Any of these genes and their products could lead to new insights into how to regulate growth and may be subject to analysis and intervention.

The invention also provides, in a representative embodiment, an isolated nucleic acid molecule (DNA or RNA) that is capable of hybridizing under stringent conditions to the nucleotide sequence residing between positions 1 and 1002 of the mad cDNA shown in FIGS. 14A–B. By "capable of hybridizing under stringent conditions" is meant annealing to a cDNA shown in FIGS. 14A–B, or its complementary strand, under standard conditions, e.g., high temperature and/or low salt content, which tend to disfavor hybridization. A suitable protocol (involving $0.1 \times SSC$, $68°$ C. for 2 hours) is described in Maniatis, T., et al., Molecular Cloning: A Laboratory Manual, Cold Spring Harbor Laboratory, 1982, at pages 387–389. The nucleic acid so annealed may be one of the two mad cDNAs shown in FIG. 14, portions thereof, or of any other alternatively spliced forms of mad-related cDNAs or genes.

The subject nucleic acid molecule preferably encodes a Mad polypeptide that can associate with a Max polypeptide. Mad is an inhibitor of Myc (and other bHLH proteins binding to Max) at least two levels. First, the Mad polypeptide is capable of competitively inhibiting binding of Myc to Max. Second, both Mad:Max and Myc:Max bind to the same CACGTG nucleotide sequence, such that Mad:Max complex is a competitive inhibitor of Myc:Max. It is reasoned likely by the inventors that once bound to DNA the Mad:Max complex acts a negative transcription regulator, while Myc:Max is a positive activator.

The subject Mad polypeptides are produced by operably linking the isolated nucleic acid molecule to suitable control sequences in recombinant expression vectors. Cells transfected or transduced with such recombinant expression vectors are capable of expressing the encoded polypeptides. Such polypeptides are generally encoded by a gene sequence capable of hybridizing under stringent conditions to the nucleotide sequence(s) residing between positions 148 and 809 of the mad gene shown in FIGS. 14A–B. Such polypeptides also preferably associate with Max polypeptides.

In a related embodiment, the invention provides an isolated polypeptide Mad:Max complex in which a Mad polypeptide is associated with a Max polypeptide. The Max polypeptide may be encoded by a nucleotide sequence capable of hybridizing with the nucleotide sequence of FIGS. 2A–B, and the Mad polypeptide may be encoded by a nucleotide sequence capable of hybridizing with the nucleotide sequence of FIGS. 14A–B. The isolated polypeptide Mad:Max complex is capable of binding to the nucleotide sequence CACGTG.

In related embodiments, the invention provides isolated DNA molecules capable of hybridizing under stringent conditions to: the nucleotide sequence residing between positions 355 and 399 of the helix I region of the mad cDNA shown in FIG. 14; the nucleotide sequence residing between positions 418 and 471 of the helix II region of the mad cDNA shown in FIGS. 14A–B; the basic region sequence residing between positions 319 and 354 of the mad cDNA shown in FIGS. 14A–B; and, the heptad hydrophobic zipper region sequences residing between positions 472 and 597 of the mad cDNA shown in FIGS. 14A–B. Mutant DNA molecules are also provided. In a representative example, the mutant DNA molecule encodes a Mad polypeptide that can specifically associate with a Max polypeptide and prevent Max binding to Myc; this particular mutant DNA molecule is capable of hybridizing to the nucleotide sequence residing between positions 148 and 810 shown in FIGS. 14A–B but not to the basic region residing between positions 319 and 354 shown in FIGS. 14A–B. A second mutant DNA molecule encodes a Mad polypeptide that can specifically associate with a Max polypeptide and inhibit binding of the mutant Mad:Max complex to DNA at the transcription regulatory CACGTG nucleotide sequence; this particular mutant DNA molecule is capable of hybridizing to the nucleotide sequence residing between positions 319 and 471 shown in FIGS. 14A–B but not to the region residing between positions 472 and 597 shown in FIGS. 14A–B.

In addition to its evident value as a research reagent, the following potential uses relating to Mad are contemplated:

1. Changes in the levels of Mad and especially of the Mad:Max complex could serves as a diagnostic or prognostic tool for diverse types of cancer. This might involve standard protocols using a reagent, such as a monclonal antibody, that recognizes the Mad:Max complex but not Mad, Max, Max:Myc, or Max:Max (i.e., homodimerized). Rearrangements of the mad gene chromosomal region may be implicated in neoplasia, since inactivation of the repressor activity of Mad may result in decreased regulatory control over endogenous positive regulatory elements, i.e., positive regulators that bind Max. In this respect, Mad may be similar to members of the tumor suppressor gene families, e.g., Rb and p53.

2. Interference with formation or maintenance of the Myc:Max complex could serve as a means of retarding neoplasia. Mad competes binding of the b-HLH zipper domains of Myc proteins to Max; and Mad:Max complexes may act as a repressor of Max:Myc activation of transcription or cellular replication. Increasing the levels of Mad polypeptides in a cell (e.g., over-expressing Mad) may counteract the activating effects of Myc. Alternatively, mutant Mad reagents (and mimetic compounds) having higher binding affinity for Max may interfere with Max binding to Myc.

3. A "dominant repressor Mad" which is capable of forming a complex with Max that either inhibits formation of Max:Myc complexes, or inhibits Max:Myc binding to CACGTG regions in DNA, may thereby influence neoplasia. One such Mad has substitutions in one or more nucleotides in the basic HLH region or zipper region of Mad that is involved in Max binding. Such HLH-region substitution or zipper-region substitution(s) in Mad preferably increase the binding affinity of Mad for Max, or of the Mad:Max complex for CACGTG regions in DNA.

4. If Mad itself is a negative regulator of Max-mediated cell growth (or Max:Myc-mediated cell growth) then increasing the levels of Mad in a cell by using gene transfer vectors may phenotypically oppose the transformed phenotype of a cell. In a related aspect, Mad (or Mad:Max complexes) may drive terminal differentiation in a cell, and gene transfer designed to increase the levels of Mad in a cell may be useful for driving terminal differentiation of a transformed (e.g., cancer) cell. Alternatively, decreasing Mad levels in a terminally differentiated cell, (e.g., through antisense vectors) could be useful to promote cell growth in vitro and tissue regeneration in vivo. For example, smooth muscle cells having a terminally differentiated phenotype may be induced to grow in vitro for prolonged periods of time using antisense Mad vectors to increase the level of expression of Mad in these cells.

5. Mad may be expressed as a competitive inhibitor of growth promoting elements in cells that specifically associate with Max, e.g., Myc, and Mad:Max complexes may act as negative repressor of such Max-binding growth promoting elements in a terminally differentiated cell. In this regard, alterations in Mad levels could influence certain key events in cellular differentiation.

6. The Mad:Max, Max:Myc, Max:Max, and possibly Myc:Myc complexes are likely to bind DNA sequences that are involved in regulation of transcription and/or DNA replication. In any case Myc, Max, and Mad may regulate genes that themselves are involved in DNA replication and cell proliferation. The genes regulated by Max:Mad, Max:Max, and Max:Myc, and the polypeptide products of such regulated genes, may lead to new insights into regulation of cell growth and terminal differentiation of cells. As such, the latter genes regulated by Max complexes may be important targets for drug development because selected chemical, polypeptide, and antisense inhibitors of expression of Mad and Max may alter cell growth and phenotype.

FIRST SERIES OF EXAMPLES

Max is a helix-loop-helix-zipper protein that associates in vitro with Myc family proteins to form a sequence-specific DNA binding complex.

EXAMPLE 1

Functional Cloning of a Myc Binding Protein

Biologically interactive proteins have been identified by functional cloning (40). This work encouraged us to use the c-Myc b-HLH-Zip region to identify proteins from a λgt11 cDNA expression library that interact with Myc. We prepared a construct that consisted of the carboxyl-terminal 92-amino acid residues of human c-Myc fused to the carboxyl terminus of glutathione-S-transferase (GST-MycC92). FIG. 1A is a diagram of the GST-MycC92 fusion protein used for iodination and screening, wherein the following abbreviations apply: CKII, casein kinase II phosphorylation site; BR, basic region; HLH, helix-loop-helix; and LZ, leucine zipper. This bacterially expressed fusion protein was soluble, easily purified, and contained 17 tryrosines as potential iodination sites (only one of which lies within the Myc segment). Furthermore, this protein, which was used to identify a specific DNA-binding sequence for c-Myc (17), contains the complete b-HLH-Zip region and thus should have the minimal structure required for DNA binding and protein interaction.

GST-MycC92 was expressed in *Escherichia coli*, purified by glutathione-agarose affinity chromatography and $^{125}$I-labeled to high specific activity. Specifically, GST-MycC92 fusion protein was expressed from a pGEX-2T plasmid (Pharmacia) that contained the 570-base pair Ava II-Eco RI fragment of human c-myc cDNA clone (0/1) ligated into the SMA I-Eco RI cloning sites. Fusion protein was purified as described [D. B. Smith and K. S. Johnson, Gene 67, 31 (1988)]. GST (50 mg) or GST-MycC92 (50 mg) were $^{125}$I-labeled to high specific activity (72 mCi/mg) with Iodobeads (Pierce) as recommended by the manufacturer [M. A. K. Markwell, Anal. Biochem. 125, 427 (1982)].

For cloning we used a random-primed λgt11 expression library derived from a baboon lymphoblastoid cell line. The λgt11 expression library was constructed from the baboon lymphoid cell line 594S as described [R. L. Idzerda et al., Proc. Natl. Acad. Sci. U.S.A. 86, 4659 (1989)]. Phage from this library produce nearly full-length β-galactosidase proteins fused with the open reading frames of the directionally cloned c-DNAs. More than $10^6$ plaques were screened for their ability to interact with $^{125}$I-labeled GST-MycC92. Specifically, the 594S λgt11 library was plated on the Y1088 bacterial strain. As plaques became visible, β-galactosidase fusion protein expression was induced by overlaying the lawns with IPTG [isopropyl β-D-thiogalactopyranoside (10 mM)]-impregnated nitrocellulose filters (Amersham; Hybond C Extra). Transfer of released proteins was allowed to proceed overnight. Filters were marked, rinsed to remove bacterial debris, and blocked with 5 percent dry milk in HND buffer [20 mM Hepes, pH 7.2, 50 mM NaCl, 0.1 percent NP-40, and 5 mM dithiothreitol (DTT)] for 1 hour at 4° C. $^{125}$I-labeled GST or GST-MycC92 (100 ng/ml, about 3 nM) was added to the filters in HND buffer supplemented with 1 percent dry milk. After a 4-hour incubation on a rotating platform at 4° C., filters were rapidly washed seven times with PBS (137 mM NaCl, 2.7 mM KCl, 4.3 mM Na$_2$HPO$_4$.7H$_2$O, 1.4 mM KH$_2$PO$_4$, pH 7.3) that contained 0.2 percent Triton X-100 (room temperature). Filters wrapped in plastic were exposed to X-ray film for 3 hours to overnight [see (40) for related protocols].

Figure 1B:
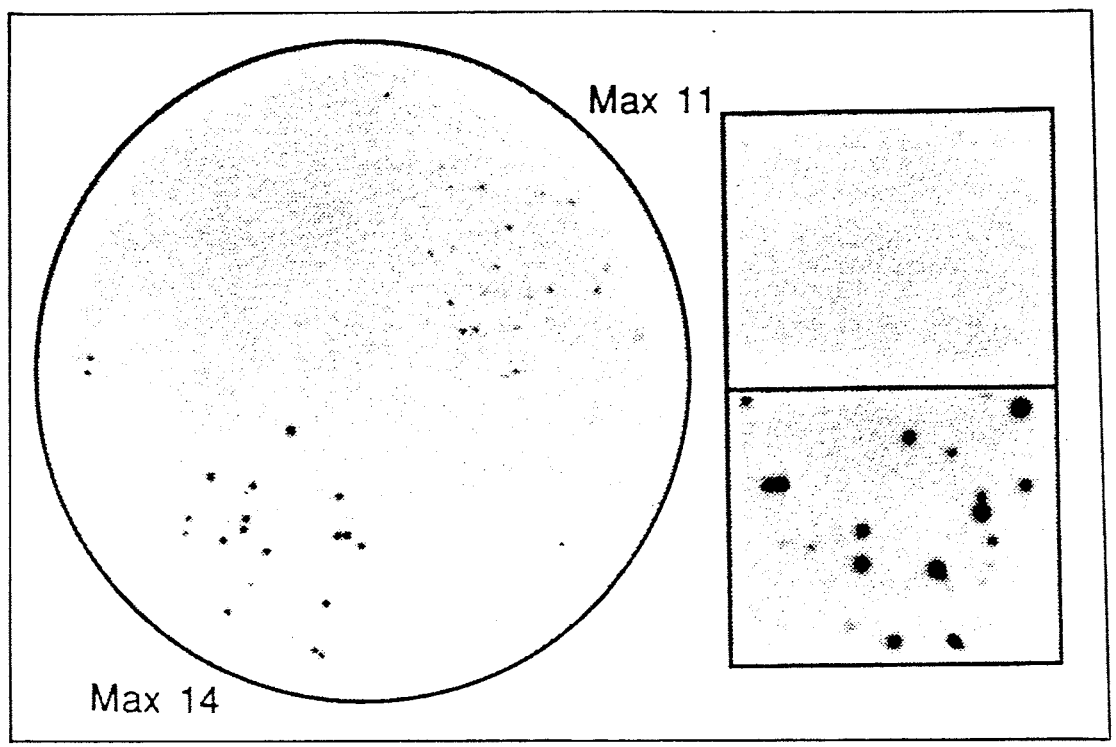
FIGS. 1B–C, show representative specific binding of the Myc fusion protein to Max polypeptide expressed by plaques, as described in Example 1.
Figure 1C:
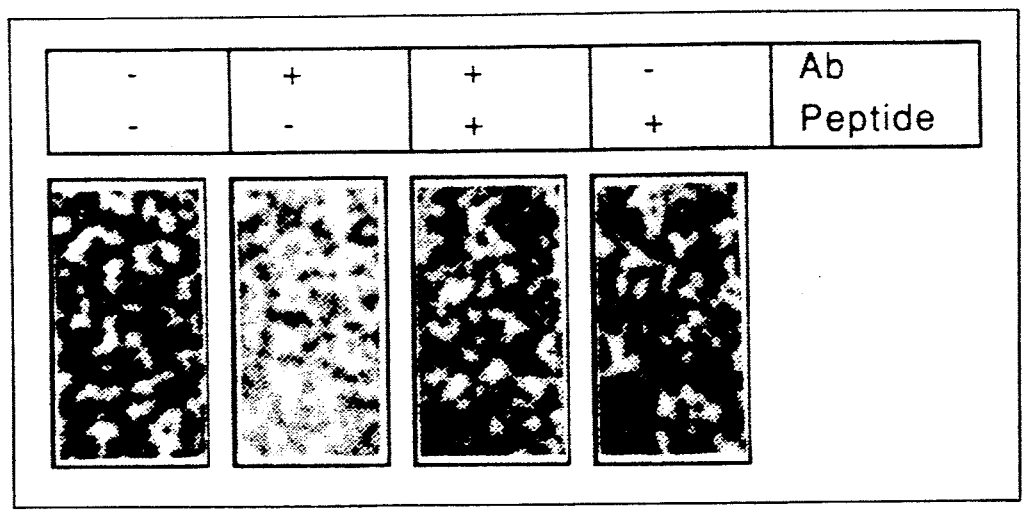

Several potential positive plaques were identified, two of which (Max11 and Max14) survived multiple rounds of plaque purification. Representative results are shown in FIGS. 1B-C, wherein: At top left, secondary plating of five putative positives demonstrates the reactivity of two of the primary plaques, Max11 and Max14. At top right, as a negative control, GST was labeled to a similar specific activity and compared with GST-MycC92 for binding to Max14 plaques.

Because the observed binding might have been mediated by the GST sequences in the fusion protein, the plaques were probed with GST $^{125}$I-labeled to the same specific activity as GST-MycC92. Only the GST fusion protein that contained c-Myc, and not GST alone, reacted with the Max14 plaques. Representative results are shown in FIG. 1B, wherein: At bottom, binding of GST-MycC92 to Max14 plaques was assayed with or without affinity purified carboxyl terminal-specific anti-Myc (Ab) or peptide immunogen (peptide). In addition, affinity-purified antibodies to the 12 carboxyl-terminal amino acids of human c-Myc (anti-Myc) (41) partially blocked the binding of GST-MycC92 to the plaques in a manner that was prevented by addition of the peptide immunogen (FIG. 1B).

To confirm that the association of GST-MycC92 with Max11 and Max14 was attributable to specific protein-protein interaction, Max11 and Max14 lysogen proteins were fractionated by SDS-polyacrylamide gel electrophoresis (SDS-PAGE), transferred to nitrocellulose filters, and subjected to protein blotting with $^{125}$I-labeled GST-MycC92. While GST-MycC92 failed to bind to β-galactosidase alone, it did bind to β-galactosidase fusion proteins in both Max11 and Max14 lysates (16). These results indicate that the Myc-containing segment of GST-MycC92 specifically interacts with the protein products encoded by Max11 and Max14 cDNAs.

EXAMPLE 2

Identification of a Helix-Loop-Helix-Zipper Domain in Max

Nucleotide sequence analysis of the inserts from both of the GST-MycC92 reactive λgt11 phages demonstrated that Max11 and Max14 encode the same protein as defined by the β-galactosidase open reading frame. Specifically, sequence analysis of Max11 and Max14 clones, along with Max clones derived from a Manca λgt10 library, was performed by the dideoxy method [F. Sanger, S. Miklen, A. F. Coulson, *Proc. Natl. Acad. Sci. U.S.A.* 74, 5463 (1977)]. The 513-nucleotide sequence presented (FIGS. 2A–B) was constructed from two overlapping Manca cDNA clones.

FIGS. 2A–B show nucleotide and amino acid sequences of Max. The Max open reading frame, as generated from overlapping Manca cell cDNAs (human), encodes a 151-amino acid polypeptide. The 9-amino acid insertion found in several PCR clones is shown above the inverted triangle. Helix I and helix II of the b-HLH homology region are underlined, while the hydrophobic heptad repeat, which extends from helix II into the zipper region, are in bold face and underscored. Basic and acidic regions are identified by their charge (+ or −), and termination codons are marked by asterisks.

Both Max11 and Max14 appear to be partial, overlapping cDNAs. Max11 and Max14 encode 124 and 131 amino acids, respectively, between the junction with β-galactosidase and a TAA termination codon. In retrospect, it is not surprising to have cloned only two functional inserts from the 10$^6$ plaques screened. Size selection of the cDNA inserts along with the presence of an in-frame stop codon located two codons 5' to the initiating AUG (see FIGS. 2A–B) limits the number of potentially functional points of lacZ fusion (that is, those that contain an intact HLH-Zip region) to 40. For comparison, screening of the 594S λgt11 library with a c-Myc carboxyl-terminal specific antiserum identified only 12 immunoreactive plaques.

Subsequent isolation of several overlapping cDNAs from a Manca (human Burkitt's lymphoma cell line) λgt10 library permitted deduction of an apparently complete open reading frame for Max that encodes 151 residues (FIGS. 2A–B). This is based on the assignment of an AUG in relatively good context for translational initiation (42) that was preceded by an upstream, in-frame termination codon. This amino acid sequence probably represents the complete Max open reading frame, because antibodies to Max (anti-Max) were used to immunoprecipitate a cellular protein that comigrated with, and produced an identical tryptic peptide map as the in vitro translation product of the Max cDNA (16). Sequencing of Max-specific polymerase chain reaction (PCR) products from Manca cDNAs revealed a putative variant form of Max that differed only by a 9-amino acid insertion amino-terminal to the basic region (FIGS. 2C–D). In the experiments described below, we utilized a Max cDNA that lacked this insertion.

Figure 3C:
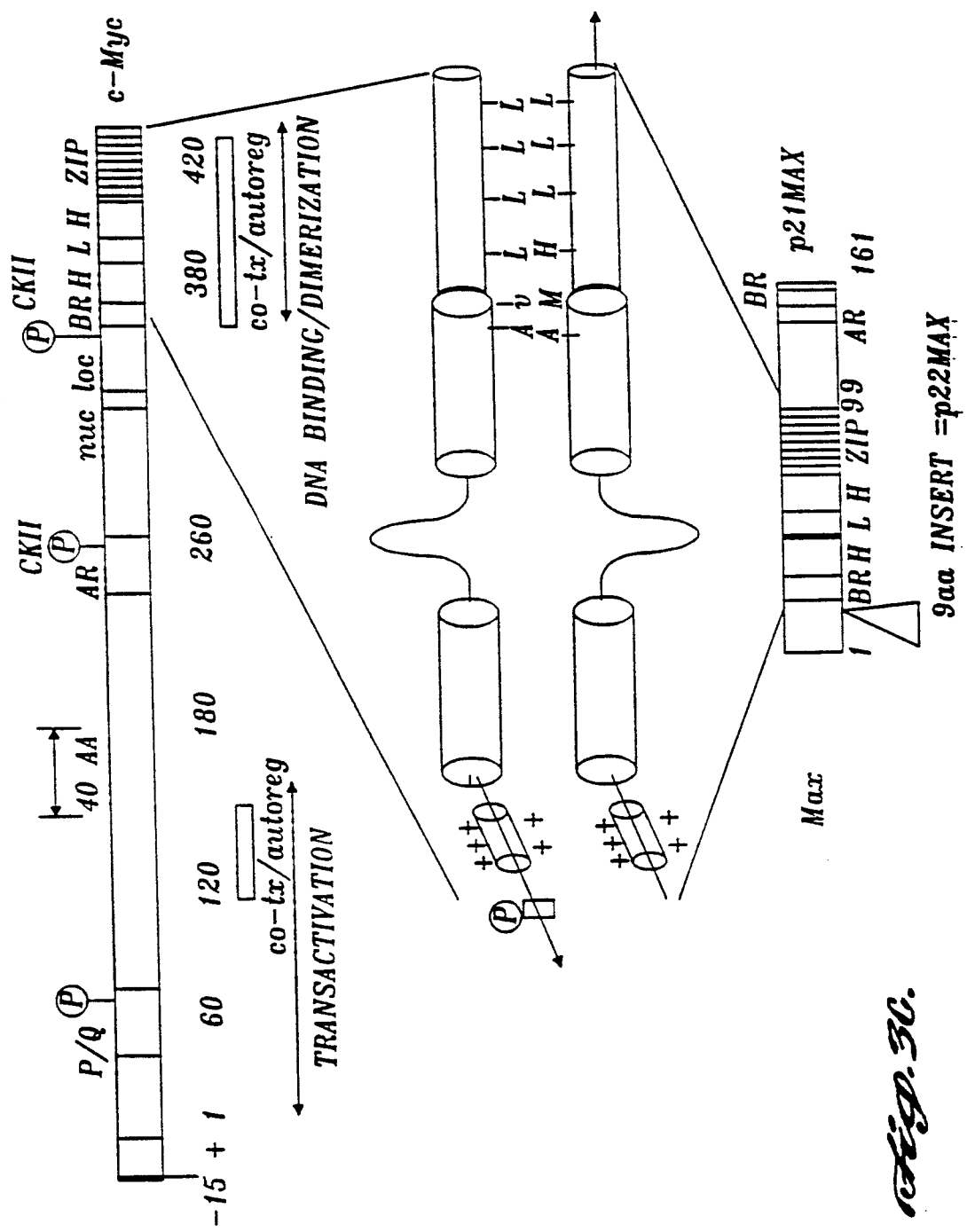
FIGS. 3C schematically depicts the alignment of the HLH regions in Myc and Max involved in protein-protein interactions that form the Myc:Max complex, and the alignment of Myc and Max bHLH-Zip regions involved in binding of Myc and Max and the Myc:Max complex to promoter sequences in DNA, as describe in Example 2.

FIGS. 3A–C show the structure of the Max protein and its sequence similarity shared with other bHLH-Zip proteins. FIGS. 3A–B show regions of sequence similarity shared with other bHLH transcription factors. The Max b-HLH-Zip region is compared and contrasted to that of other b-HLH proteins found in humans (MyoD, E12, AP-4, USF, c-Myc, L-Myc, and N-Myc), insects (As-C), plants (Lc), and yeast (CBF-1). Shaded regions identify residues that fit the consensus as derived from the known b-HLH family (43) (F=L, I, V, M; W=F, L, I, Y). Boxes denote the heptad repeat of hydrophobic residues, which extends from helix II into the putative leucine zipper.

Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

A computer search of the protein database IPIR Version 25) revealed sequence similarity between a segment of the Max open reading frame and the b-HLH proteins, including members of the Myc family (FIGS. 3A–B). The Max sequence in this region represents a nearly exact match with the HLH consensus (FIGS. 3A–B bottom) (43). The similarity among Max and the b-HLH proteins also extends in the amino-terminal direction into a basic region of Max. The Max sequence just carboxyl terminal to helix II contains a series of hydrophobic amino acid residues, three of which are leucines, spaced seven residues apart (FIGS. 3A–B boxed residues). Helical wheel analysis (12) of this region suggests that the amphipathic helix II may extend into and beyond the three leucines. These leucines and the other nonpolar residues might form a hydrophobic face similar to that in the leucine zipper proteins.

We have also shown that a 15-amino-acid deletion of the basic region abolishes the capacity of c-myc to cotransform Rat-1 cells i collaboration with the brc-abl oncogene. In contrast, a 9-amino-acid detection of a neighboring region, the CKII phosphorylation site (see FIG. 3C), has little effect on cotransformation (data not shown). These experiments lend further support to the notion that the b-HLH-Zip region of Myc is critical for function.

FIG. 3C presents a schematic representation of Myc and Max proteins as aligned by their regions of sequence similarity (stippled boxes). Abbreviations are used to designate the casein kinase II phosphorylation site (CKII), basic region (BR), helix-loop-helix (HLH), leucine zipper (LZ), and acidic region (AR). Numbering corresponds to their respective amino acid sequences.

The Max polypeptide sequence is hydrophilic in nature. More than one-third of its residues are charged, and the most abundant amino acid is serine (14 percent) Max contains no cysteines. Despite a predicted molecular size of 17,200 daltons, Max, like Myc, exhibits aberrant electrophoretic mobility in SDS-polyacrylamide gels (see FIG. 5A). The organization of the Max cDNA protein coding sequence and the relative extents of the basic, HLH, zipper, and carboxyl-terminal regions are depicted in FIG. 3C. The similarity of Max with other bHLH proteins is limited to the Max bHLH region, and the sequences of baboon and human Max do not correspond to those of any previously identified protein.

EXAMPLE 3

Specific interaction of Max with Myc family proteins

The present of putative bHLH and leucine zipper domains in Max suggests that Max interacted with a similar region of GST-MycC92 in the functional library screening. To further investigate the potential of this region of Max to associate with Myc, we developed an affinity chromatography assay in which the Max protein, linked to a solid support, was used to test for binding of full-length, wild-type Myc and a series of mutant Myc proteins.

A set of deletion and point mutations were introduced into a wild-type human c-myc cDNA (pHLmyc 0/1) that contained the complete c-Myc open reading frame (44). Specifically, oligonucleotide-directed mutagenesis was used to generate a variety of mutant Myc proteins: $\Delta$C89, deletion of the carboxyl-terminal 89 resides (deleted amino acids 351 to 439, added Arg-Arg-Thr-Ser); $\Delta$BR, deletion of the basic region (deleted amino acids 353 to 367); $\Delta$CKII, deletion of the casin kinase II phosphorylation site located 5' of the basic region (deleted amino acids 346 to 354); $\Delta$Helix 1, deletion of $\Delta$helix 1 (deletion of amino acids 368 to 381); $\Delta$LZ, deletion of the leucine zipper (deleted amino acids 416 to 439); BR21M, replacement the basic region of Myc with that of MyoD (replaced Myc amino acids 347 to 367 with MyoD amino acids 102 to 122); BR21MDLZ, double mutant that consists of BR21M and D LZ; and ProZip, replacement of Leu (amino acid residue 420) with Pro (from A. J. Street). Deletion of sequences 5' to the Pvu II site in the 0/1 cDNA resulted in D N100; translation from this construct initiates at the first internal methionine (amino acid 101). Numbering corresponds to the amino acid sequence of human c-Myc [R. Watt et al., Nature 303, 725 (1983)]. Dideoxy sequencing and immunoprecipitation of in vitro translation products were used to confirm the identity of each construct.

RNAs prepared from the normal and mutated clones by in vitro transcription were translated in a rabbit reticulocyte lysate to generate c-Myc proteins labeled with [$^{35}$S]methionine. Specifically, in vitro transcription and translation were performed under conditions recommended by the Promega Protocols and Applications Guide. [$^{35}$S]Methionine labeled proteins were produced from each of the following vectors: pVZ1-Max11/13/14, pBluescribe vectors that contained the mutant Myc constructs, pU313S (L-Myc) (from K. Alitalo), pNmycB (N-Myc) (from R. Bernards), pV2C11a (MyoD) (from A. Lassar) (11), E12R (E12) (from C. Murre) (7), pBS-B065 (myogenin) (from W. Wright) (45), tal-SP6pGem (Tal) (from R. Baer) (46), pJun7'8 (Jun) (from R. Turner), pSP65fos1B (Fos) (from T. Curran), D12.2 (USF) (from R. Roeder) (47), and T7bAP-4 (AP-4) (from Y-F. Hu and R. Tijan) (48). Programmed reticulocyte lysate (1 ml) was subjected directly to SDS-PAGE, or lysates (20 ml) were diluted into HND buffer (400 ml) that contained bovine serum albumin (BSA) (10 mg/ml). Half of this dilution was incubated with either GST or GST-Max124 beads [approximately 5 mg of fusion protein adsorbed to 10 ml of glutathione-Sepharose (Pharmacial)] for 1 hour at 4° C. The resin was then washed four times with PBS that contained NP-40 (0.1 percent) at room temperature. The bound proteins were eluted with SDS-containing sample buffer and subjected to SDS-PAGE and autoradiography.

A fusion protein that contained the carboxyl-terminal 124 amino acids of Max (GST-MaxC124) was coupled to glutathione-Sepharose beads. GST-MaxC124 was constructed by insertion of the Ava II-Eco RI fragment of Max14 into the Sma I site of pGEX-3X expression vector (Pharmacia). The resulting fusion protein had the 124 carboxyl-terminal amino acids of Max in frame with GST sequences. Fusion protein was purified as described in Example 1, supra. The labeled in vitro translation products (FIG. 4A, top panel) were incubated with GST-MaxC124 or GST resin, washed under low stringency conditions, and the bound material was eluted with SDS and analyzed by SDS-PAGE as described above.

Figure 4:
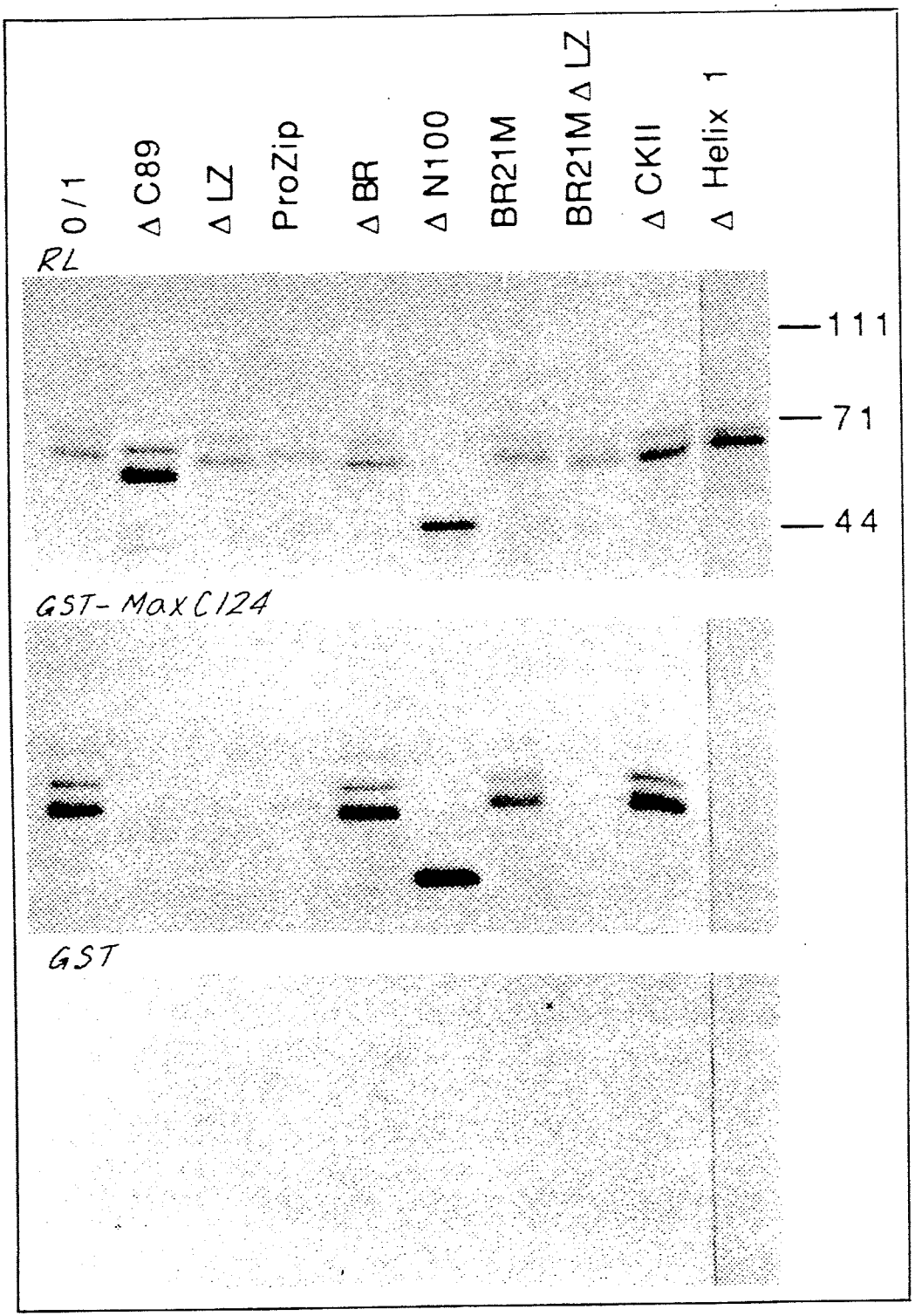
FIG. 4 shows representative binding of Myc with Max to form the Myc:Max complex isolated by affinity chromatography, as described in Example 3.

FIG. 4 presents structural requirements for Myc-Max association. Wild-type (0/1) or mutant forms of the c-Myc protein were assayed for their ability to associate with the HLH-Zip motif of Max. After in vitro translation, programmed reticulocyte lysate (RL) was subjected directly to SDS-PAGE analysis (1 ml), or the sample (10 ml) was purified on GST or GST-MaxC124 affinity columns and the bound material was subjected to SDS-PAGE as described above. Mutations: $\Delta$N100, deletion of the amino-terminal 100 amino acids of c-Myc (this mutation removes the two alternative initiation codons that normally are translated to produce the p64-p67 doublet); $\Delta$C89, deletion of the carboxyl-terminal 89 amino acids; $\Delta$LZ, deletion of the leucine zipper, $\Delta$BR, basic region deletion, $\Delta$Helix 1, helix I deletion, $\Delta$CKII, casein kinase II phosphorylation site deletion (49); ProZip, proline was substituted for leucine at position 2 of the zipper region; BR21M, the basic region of C-Myc was replaced with that of MyoD). Migration of the molecular size markers are indicated.

None of the c-myc translation products bound to GST alone (FIG. 4C, bottom panel), while GST MaxC124 resin retained the wild-type c-Myc proteins, p64 and p67 (0/1; FIG. 4, middle panel). The ability of c-Myc protein to interact with Max was dependent on an intact carboxyl terminus, as deletion of the carboxyl-terminal 89-amino acid residues ($\Delta$C89) completely abolished binding to Max, while deletion of 100 residues at the amino terminus ($\Delta$N100) had no effect (FIG. 4B, middle panel). To ascertain what regions within the carboxyl-terminal domain were required for the binding, we examined a series of mutations. Neither deletion of the Myc basic region ($\Delta$BR), its substitution with the MyoD basic region (BR21M), or deletion of one of the CKII phosphorylation sites (CKII, just amino terminal to the basic region) (49) had any effect on association with Max. In contrast, binding to Max was inhibited by deletion of either c-Myc helix I or the leucine zipper, as well as by substitution of a helix-disrupting proline residue for the second leucine in the zipper. These results suggest that full-length c-Myc interacts with the carboxyl-terminal region of Max and that this association is mediated by the c-Myc HLH-Zip domain.

Figure 5A:
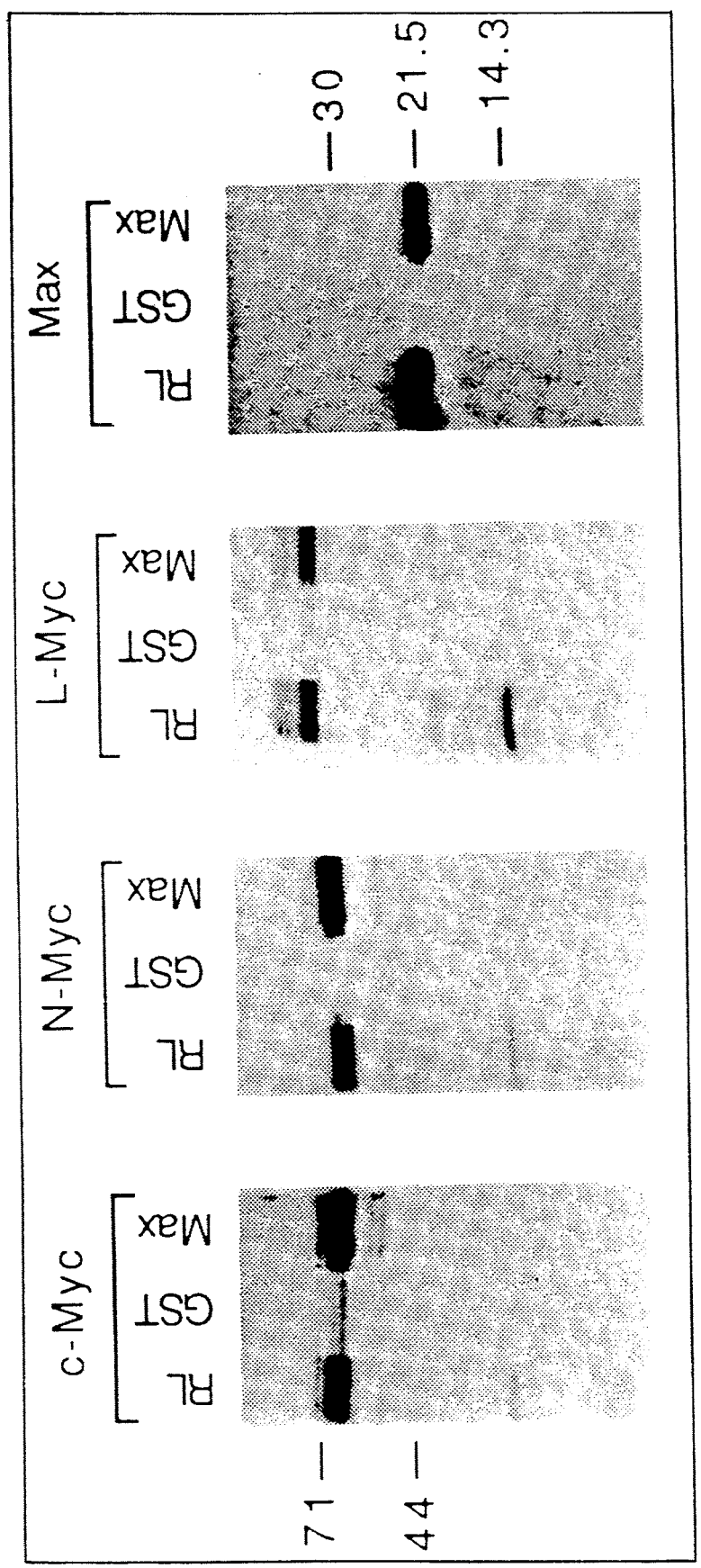
FIG. 5A shows binding of Max to Myc family members, as described in Example 3.
Figure 5B:
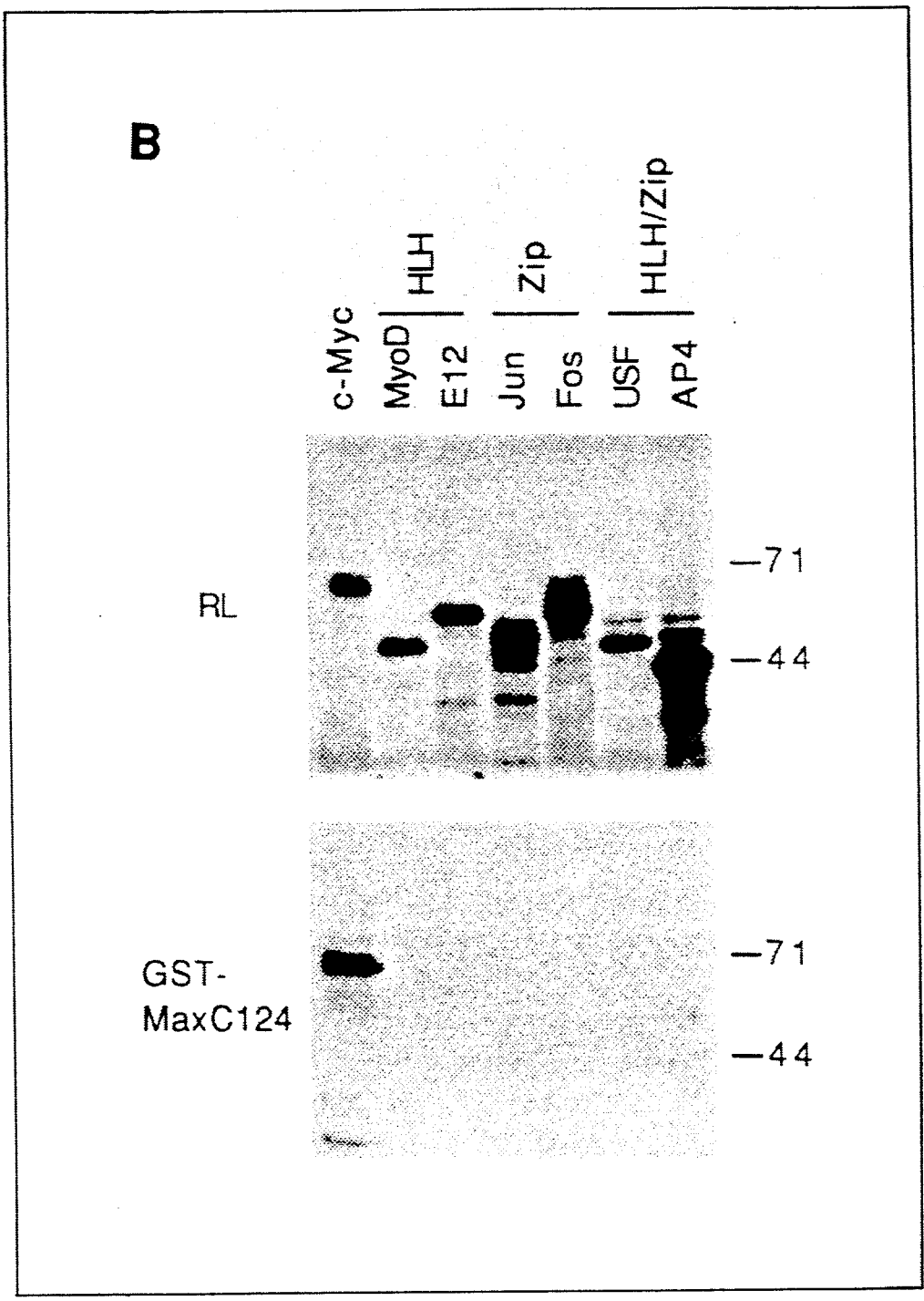
FIG. 5B presents the results of experiments showing the specificity of the Myc:Max interaction and failure of Myc to interact with other HLH bZip polypeptides, as described in Example 3.

Because N-Myc and L-Myc also have b-HLH-Zip regions at their carboxyl termini (7, 12), we assessed their ability to bind Max. Results are shown in FIGS. 5A-B which presents an analysis of Max binding to Myc family members (5A), and to b-HLH, bZip, and b-HLH-Zip (5B) proteins. In vitro transcription and translation were used to produce proteins labeled with [$^{35}$S]methionine. After in vitro translation, programmed reticulocyte lysate (RL) was subjected directly to SDS-PAGE analysis (1 ml), or the lysate (10 ml) was purified on GST or GST-Max C124 (Max) affinity columns and the bound material was subjected to SDS-PAGE as described above. Molecular size markers migrated as indicated on the SDS-PAGE analysis.

[$^{35}$S]Methionine-labeled in vitro translation products, generated from N-myc cDNAs, bound to GST-MaxC124 resin with the same efficienty as the c-Myc protein (FIG. 5A). In vitro translated, full-length Max protein also bound to the Max-containing resin suggesting that Max may homo-oligomerize. Neither the Myc family proteins nor Max bound GST alone. To test the possibility that any protein that contains an HLH or leucine zipper motif might associate with Max, we obtained cDNAs that encode other transcription factors and determined the ability of their in vitro translation products to bind to GST-MaxC124 resin. Categories of transcription factors examined included MyoD, E12, Tal, and myogenin, all of which possess b-HLH domains (8, 45, 46); Fos and Jun, each of which contain a leucine zipper (12); and AP-4 (48) and USF (47), which contain adjacent HLH and leucine zipper regions. Although none of these proteins bound either GST or GST-MaxC124, specific interaction between c-Myc and GST MaxC124 was again observed (FIG. 5B). This assay is a rather stringent test of association, because relatively low amounts of labeled protein compete for binding with a large excess of max homodimers (or homo-oligomers). Furthermore, the reticulocyte lysate may containing competitors or inhibitors of binding. Therefore, the inability of specific proteins to interact with Max in the assay may not be a reflection of the in vivo situation.

EXAMPLE 4

Formation of a Myc-Max complex with sequence-specific DNA-binding activity

Experiments in which bacterially expressed GST-MycC92 was used to select preferred DNA sequences from a pool of partially randomized oligonucleotides have shown that c-Myc has specific DNA-binding activity for the sequence CACGTG(17). Compared to other bHLH proteins used in this assay, in vitro translated c-Myc bound relatively poorly to an oligonucleotide that contained this sequence (CM-1). These results might be explained in terms of inefficient homodimerization, inefficient binding of homodimers to the CM-1 sequence, or both. Because Max is capable of specifically associating with Myc, we tested the possibility that the Myc-Max heterocomplex might exhibit increased binding to CM-1 compared to Myc alone.

Figure 6:
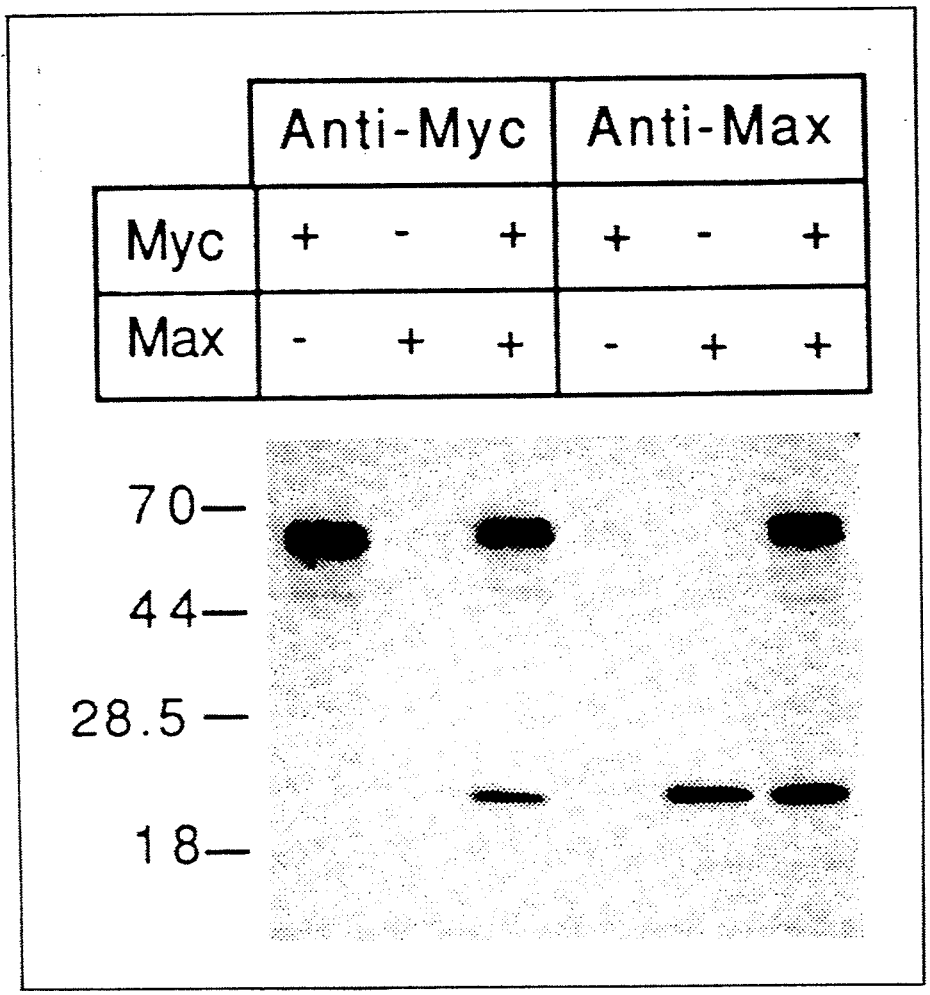
FIG. 6 shows formation of the Myc:Max complex by Myc and Max polypeptides synthesized in vitro and isolation of the complex by immunoprecipitation and SDS-PAGE, as described in Example 4.

For the DNA-binding assays, it was important to use full-length Myc and Max proteins in a soluble complex. Therefore, we first determined whether the full-length forms of both Max and c-Myc specifically associate in solution. The p64 and p67 c-Myc proteins and the p21 Max protein produced by in vitro translation of their respective cDNAs were recognized by their cognate antisera (FIG. 6). Specifically, in vitro transcripts from the c-Myc and Max vectors were added to a Promega reticulocyte lysate translation mixture and incubated for 1 hour at 30° C. c-Myc and Max (2:1) were mixed after translation, thus compensating for differences in the translational efficiencies of the two RNA species; association was allowed to proceed for 30 minutes at 30° C., after which the lysates were diluted into PBS with 1 percent NP-40. Proteins were immunoprecipitated under these mild conditions with anti-Myc (5 mg of affinity purified) (41) or anti-Max (5 ml of polyclonal antisera to the GST-Max124 fusion protein (described above). Immunoprecipitations were blocked by the addition of the cognate immunogen. Antigen-antibody complexes were isolated on protein A-Sepharose beads (Sigma), and the pellets were washed five times with PBS that contained 1 percent NP-40. The [$^{35}$S]Methionine labeled samples were analyzed by SDS-PAGE under reducing conditions.

FIG. 6 shows post-translational association of full-length Myc and Max. After separate in vitro translations, c-Myc and Max lysates were mixed, incubated for 30 minutes at 30° C., and immunoprecipitated with the indicated antibodies under the low stringency conditions described above. Anti-Myc was specific for the carboxyl-terminal 12 amino acids of human c-Myc (41); anti-Max was raised against the GST-MaxC124 fusion protein. Immunoprecipitated [$^{35}$S]methionine labeled proteins were resolved by SDS-PAGE.

Under low stringency immunoprecipitation conditions, anti-Myc failed to recognize Max and anti-Max failed to recognize c-Myc. However, when Max and c-Myc were combined after translation, each antiserum precipitated Max was well as c-Myc. The ability of a specific antiserum to precipitate the two proteins after mixing is best explained by formation of Myc-Max complexes that are stable under the immunoprecipitation conditions. This idea is supported by the results of blocking experiments, which demonstrate that coprecipitation of both proteins occurs only through the antigenic determinants of one of them (16). The Myc mutants that fail to bind to truncated Max in the affinity chromatography experiments (FIG. 4) also did not associate with full-length in vitro translated Max in the coimmunoprecipitation assay (16).

Having established that full-length Max and c-Myc associate in solution, we next determined whether the Myc-Max complex could bind a specific DNA sequence in a gel retardation assay. Specifically, Max or c-Myc transcripts were translated in vitro with nonradioactive methionine. Post-translational mixes were performed as in described above, and the resulting lysates were analyzed for binding to the synthetic CM-1 oligonucleotide by the electrophoretic mobility shift assay [A. Revzin, BioTechniques 7, 346 (1989)]. Final conditions within a 25-ml binding reaction were: 20 mM Hepes, pH 7.2, 50 mM KCl, 3 mM MgCl$_2$, 1 mM DTT, 1 mM EDTA, 8 percent glycerol, 25 ng of sheared salmon sperm DNA as a nonspecific competitor, 10 ml of programmed reticulocyte lysate, and 0.2 ng of $^{32}$P-labeled CM-1 oligo (17). The DNA-binding reaction was allowed to proceed at room temperature for 10 minutes. For antibody experiments, affinity purified anti-Myc or anti-Max (1 mg) was added for 10 minutes after the formation of the nucleoprotein complex; the cognate immunogen (10 mg) blocked this supplemental shift. As competitors, double-stranded oligonucleotides were added at 1, 10, and 100 ng per reaction; the core sequence of the B1/B2 and CM-1 templates are 5'-CCCCCAACACCTGCTGCCTGA-3' and 5'-CCCCCACCACGTGGTGCCTGA-3', respectively (17). Protein-DNA complexes were resolved on a 5 percent acrylamide gel (50 mM tris base, 50 mM borate, 1 mM EDTA), and gels were dried prior to autoradiography.

Incubation of an unprogrammed reticulocyte translation lysate with the $^{32}$P-labeled CM-1 oligonucleotide resulted in retardation of the probe (FIG. 7A). This binding appeared to be due to endogenous USF protein, which also recognizes the CM-1 sequence. Specifically, the background bands in the gel retardation assays were due to endogenous USF binding factor activity, and binding of USF could be inhibited by the addition of the CM-1 probe. USF specifically binds to the CM-1 consensus [R. W. Carthew, L. A. Chodosh, P. A. Sharp, Cell 43, 439 (1985); M. Sawadogo and R. Roeder, ibid., p. 165; A. C. Lennard and J. M. Egly, EMBO J. 6, 3027 (1987)] and is present in the reticulocyte lysates, as evidenced by the ability of antibodies to USF to alter the mobility of these bands (L. Kretzner, unpublished data). Antibodies to USF were provided by M. Sawadoto.

When the translation lysates were programmed with Max RNA, no additional binding to the probe was detected, while lysates that contained c-Myc reproducibly showed a faint band of retarded probe (FIG. 7A). Retardation of the CM-1 probe was observed when reticulocyte lysate that contained both c-Myc and Max were used in the assay. That both c-Myc and Max proteins were bound to the retarded DNA probe was demonstrated by the ability of both anti-Myc and anti-Max to decrease the electrophoretic mobility of the bound probe. The specificity of this antibody effect on mobility of the probe was confirmed by the fact that it could be reversed for each antibody by addition of the cognate immunogen (FIG. 7A). The specificity of binding to CM-1 was verified in competition experiments in which a 5 fold excess of unlabeled CM-1 was sufficient to compete for binding by the Myc-Max complex. By contrast, a 500-fold excess of an oligonucleotide (B1/B2) that contained a binding site for MyoD and E12 (50) and differed by only three nucleotides from CM-1 was required to achieve a similar degree of competition (FIG. 7B).

Considered in additional detail, FIG. 7 presents analysis of Myc-Max complex DNA-binding activity. FIG. 7A: the ability of in vitro translated Myc and Max proteins to bind to the CM-1 oligonucleotide (CACGTG core consensus) was assessed by electrophoretic mobility shift assay. Post-translational mixes of Myc and Max were performed as in reference to FIG. 6. Lysates were incubated with $^{32}$P-labeled CM-1 prior to resolution in a 5 percent acrylamide gel. In experiments where antibodies were added, affinity purified antibody (1 mg) was added after formation of the nucleoprotein complex to minimize steric interference. To block the antibody effect, cognate immunogen (1 mg) was added. The positions of probe specifically bound and further retarded by antibody are indicated with asterisks. The arrow indicates free oligonucleotide. CM-1 oligonucleotide alone (probe) and unprogrammed reticulocyte lysate (RL) served as background controls. FIG. 7B: The specificity of the Myc-Max shift was tested by competition with 5-, 50-, and 500-fold excess of unlabeled oligonucleotide. B1/B2 contains the 3' MCK enhancer binding site for MyoD (CACGTG core consensus) and differs from CM-1 at only three positions. FIG. 7C: Requirements for the formation of a nucleoprotein complex. Various c-Myc mutants (see FIG. 4 discussion for abbreviations) were assayed for their ability to bind CM-1 in association with Max.

Binding of Myc to immobilized Max was dependent on the integrity of the HLH and leucine zipper domains (FIG. 4). To ascertain whether the association of Myc and Max in a nucleoprotein complex required the same sequences, some of the c-Myc mutants were examined for their ability to bind to CM-1 in a complex with Max. Specific binding to the CM-1 probe by Max and c-Myc was abolished when c-Myc mutants that lacked the putative leucine zipper domain or basic region were used in place of wild-type c-Myc. By contrast, a c-Myc deletion mutant that did not directly affect the b-HLH-Zip region (such as DN100, which lacks 100 amino-terminal residues of c-Myc), both associated with Max (FIGS. 5A-B) and bound to the CM-1 oligonucleotide. Therefore, loss of DNA binding correlates with the inability of c-Myc mutants to associate with Max in the binding assay. An exception to this is the basic region deletion mutant, which associated with Max but did not bind the CM-1 probe (FIGS. 7A-C), a result that suggests a requirement for the basic region of c-Myc in specific DNA binding but not in protein-protein interactions.

Implications for Myc function: Studies on the b-HLH and bZip regions within a number of eukaryotic transcription factors have distinguished two essential yet separable functions for these domains: dimerization (HLH, Zip) and DNA-binding activity (basic region) (9, 10). Here we show that the b-HLH-Zip domain of c-Myc is capable of specific interaction with a newly identified b-HLH-Zip protein, Max. Our in vitro experiments are consonant with studies on the structure and properties of Myc (1) and may serve as a basis for understanding the mechanism of Myc function in vivo. Using anti-Myc, we have identified the Max protein in immunocomplexes from avian and human cells, a further indication that the Myc-Max association is likely to be biologically relevant (16).

Two regions within the c-Myc protein appear to be critical for c-Myc function as judged by assays for cotransformation, inhibition of differentiation, and suppression of endogenous Myc expression; these are (i) an approximately 40- to 60-amino acid segment centered about residue 120, and (ii) the 95-amino acid carboxyl-terminal region (3-5). Our results suggest that the carboxyl terminus mediates association with Max and formation of a sequence-specific DNA-binding complex. The mutations that negatively affected the ability of c-Myc to interact with Max and bind CM-1 (FIGS. 4 and 7A-G), such as deletion or disruption of the zipper, are either identical or very similar to those that abolish c-Myc activity in biological assays (3-5).

The dimerization function that resides within the c-Myc HLH-Zip domain appears to be independent of the basic region, which is likely to directly mediate DNA binding. The same c-Myc basic region deletion mutant that had no effect on association with Max completely abolished the ability of the Myc-Max complex to bind the CM-1 DNA probe (FIG. 7C). This basic region deletion mutation also abolished the ability of c-Myc to transform Rat 1 cells in collaboration with bcr-abl, while deletion of the adjacent upstream segment had no effect (16). Replacement of the c-Myc basic region with that of MyoD was likewise biologically inactive although, as expected, the chimeric protein was capable of association with Max (FIG. 4). Taken together, these results demonstrate that both the dimerization and DNA-binding activities that reside in the carboxyl-terminal bHLH-Zip domain are essential for important aspects of c-Myc activity.

A striking finding of our study is that Max interacts specifically with three members of the Myc family of proteins. Numerous attempts to demonstrate heterodimer formation between Myc and other b-HLH, bZip, and b-HLH-Zip proteins have not been successful (10, 15, 16). However, under our assay conditions Max is capable of associating with c-Myc, N-Myc, and L-Myc (FIG. 5A). Other proteins that contain related dimerization domains, including the b-HLH-Zip proteins USF and AP-4, did not associate (FIG. 5B). Leucine zipper segments alone determine specificity in Fos-Jun association (51) and act to organize the two proteins in a parallel array (13). Max and the Myc proteins, however, all have HLH domains in addition to zipper regions, and our data show that the integrity of the HLH region is also important for heterodimer formation (FIG. 4). If an initial interaction between parallel zipper regions is required for proper orientation, then the appropriate alignment of contiguous HLH regions required for proper orientation might influence binding. In Max and the Myc family, the hydrophobic residues of the putative leucine zipper appear to maintain their heptad spacing well into helix II, possibly extending the coiled-coil interaction. By contrast, in USF (47) the heptad phasing is disrupted at the helix II-zipper boundary, and in AP-4 (48) the hydrophobic array does not extend as far into helix II (FIGS. 3A-B). While it remains to be determined whether these differences are important for the apparent restricted specificities of binding, other factors are likely to influence association, including the size and composition of the loop region (11), the nature of specific residues within the helical segments (52), and the presence of other domains in the protein that may facilitate or block interaction. Although we have assumed that Myc and Max interact to form dimers, it is possible that they may also participate in higher order associations.

The fact that N-Myc and L-Myc as well as c-Myc specifically associate with Max suggests that Max may serve to integrate the functions of the these three proteins that are differentially expressed during development, differentiation, and neoplasia(1). If so, Max might be expected to be expressed in at least as many cell types as are Myc family proteins. Initial experiments with Northern (RNA) blotting indicate that a 2.1-kb Max RNA is expressed in many cells and tissues at concentrations comparable to those of c-Myc. In addition, low stringency Southern (DNA) blot analysis suggests that Max is highly conserved as a single gene or a small family of genes in vertebrate genomic DNA, but is absence from invertebrates that also lack Myc homologs(16). These results are consistent with the possibility that Max, or a small number of Max-related proteins, interacts with Myc family proteins to mediate their specific biological functions. Whether Max can also be oncogenically activated poses an interesting biological question.

Important questions raised by this work concern the way in which the properties of Myc and Max are altered through association. Our experiments demonstrate that complex formation generates sequence-specific DNA binding activity for the CM-1 oligonucleotide under conditions where neither Myc nor Max alone bound significant amounts of probe (FIG. 7). This oligonucleotide contains the CACGTG consensus, which serves as a binding site for presumptive Myc homodimers (17,36). That this is a weak binding site may be reflected by the low but detectable binding by in vitro translated Myc. No binding by Max alone could be detected, indicating that either Max doe not recognize CM-1 or that it does not homodimerize under the conditions of the assay. A key point becomes whether the Myc-Max heterocomplex has a specifity for DNA binding that is distinct from that of either of the homodimers. By analogy with MyoD and the E2A proteins, each member of a Myc-Max complex might contribute half-site recognition in defining DNA-binding specificity (38). The Myc-Max complex can be used directly to select a putative new binding sequence with the method for preferential binding and amplification of random sequences (38).

Another major question concerns the function of the Myc-Max complex. It has been suggested that Myc may function in transcription, DNA replication, or both (1). The characteristics of the Myc-Max complex places there proteins in the same general class as b-HLH transcription factors, but the results do not rule out other possible functions. The essential amino-terminal region of c-Myc has been shown to act as a transcriptional activation domain when linked to yeast or prokaryotic DNA-binding domains (53). However, introduction of c-myc alone into cells only induces variable, usually low, activation of different promoters (54). While the HLH-Zip region constitutes the very carboxyl terminus of all the Myc family members, the HLH-Zip region of Max is nearly 50 residues from its carboxyl terminus (FIG. 3C). This region, which probably extends past the dimerized regions of Myc and Max, contains additional acidic and basic patches (FIGS. 2C-D) that could interact with components of the transcriptional machinery or other factors (55). Whatever their function, the ability of these polypeptides to form multiprotein complexes suggests that the differential regulation of their relative concentrations could be important determination of Max-Myc family associations, consequent DNA-binding specificities, and ultimately, the influence of Myc on cell proliferation and behavior.

SECOND SERIES OF EXAMPLES

Here we have identified the Myc-binding protein Max in vivo and have shown that Myc and Max are associated in the cell.

The protein encoded by the c-, L- and N-myc protooncogenes are short-lived nuclear phosphoproteins which possess DNA binding and protein dimerization domains structurally related to those found in an increasing number of transcription factors (see 56-58). For this class of factors dimerization is mediated by a putative helix-loop-helix region which in some cases (as in the Myc family proteins) is contiguous with a leucine zipper motif (HLH-Zip). Dimerization is required for specific DNA binding by the short stretch of basic amino acids (b) which precedes the HLH-Zip region. (see 58, 59 for reviews) As described above, by employing a functional cloning strategy we previously identified a novel human cDNA which encodes a bHLH-Zip protein Max. Max associates in vitro with the c-Myc, N-Myc, and L-Myc proteins but not with other bHLH-Zip proteins tested (60). A murine homolog of Max has also been identified (61). Association between Myc and Max requires the HLH-Zip regions of both proteins (60, 61). In addition, the human c-Myc:Max complex binds to DNA in a sequence-specific manner under conditions where Myc or Max alone display relatively, weak binding. DNA binding is dependent on the basic region as well as the HLH-Zip domains of both partners (60-62). Given the results of these in vitro studies it seemed important to identify and characterize Max and determine whether it associates with Myc in vivo.

EXAMPLE 5

Myc Associates in vivo with Max

To study Max in vivo we produced an antiserum against a purified fusion protein containing the 124 carboxyl-terminal residues of human Max linked to the carboxyl-terminus of glutathione-S-transferase (GST-MaxCI24). Specifically, GST-Max C124 was constructed and purified as described above. Affinity purified antibodies to the 12 carboxy-terminal amino acids of human c-Myc (anti-Myc) have been characterized elsewhere (63).

The anti-GST-MaxCI24 serum (anti-Max) was used to immunoprecipitate max from whose cell lysates prepared from [$^{35}$S]-methionine-labeled human Burkitt's lymphoma cells (Manca). Specifically, immunoprecipitations from from [$^{35}$S]methionine-labeled cells were performed using high stringency conditions as previously described [B. Lüscher, L. Brizuela, D. Beach, R. N. Eisenman, *EMBO J.* 10, 865 (1991)]. All SDS PAGE samples were resolved on 15% acrylamide gels under reducing conditions. For two-dimensional tryptic peptide analysis, Max proteins were immunoprecipitated and treated with alkaline phosphatase prior to gel purification and peptide mapping (64).

Figure 8A:
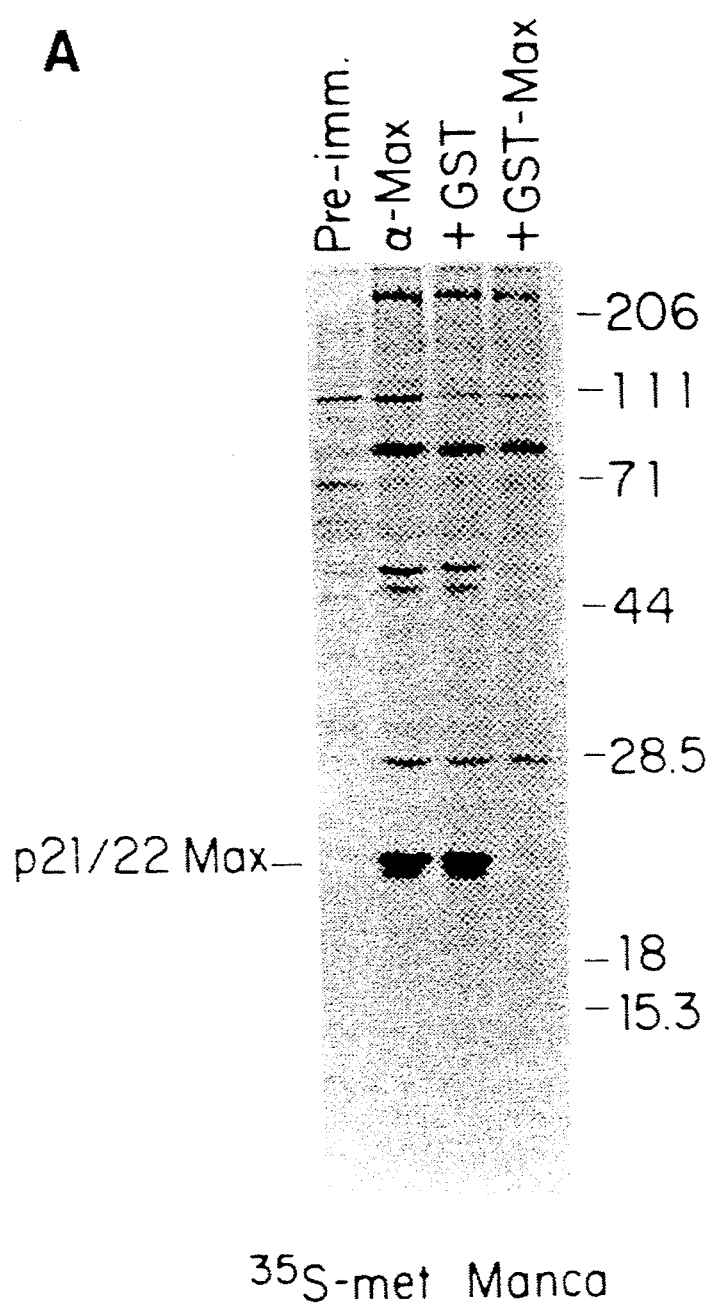
FIG. 8A shows detection and isolation of Max p21 and Max p22 polypeptides from mammalian cells, as described in Example 5.

SDS-PAGE analysis of an anti-Max immunoprecipitate revealed a predominant doublet with relative molecular masses of 21,000 and 22,000 ($M_r$ 21K and 22K) which was not recognized by the cognate preimmune serum (FIG. 8A). Immunoprecipitation of the 21/22K proteins could be competitively inhibited by excess GST-MaxC124 protein, but not by excess GST alone, suggesting that p21/22 are recognized through determinants specific to the Max segment of the immunogen. To determine whether p21/22 are also structurally related to Max we compared two-dimensional $^{35}$S-methionine tryptic peptide maps of the protein generated by in vitro transcription/translation of the p21 Max cDNA clone and of the p21/22 proteins from Manca cells. FIGS. 8B-E show that the labeled peptide patterns are superimposable suggesting that the p21/22 proteins recognized by anti-Max are highly related to Max.

Figures 8B, 8C:
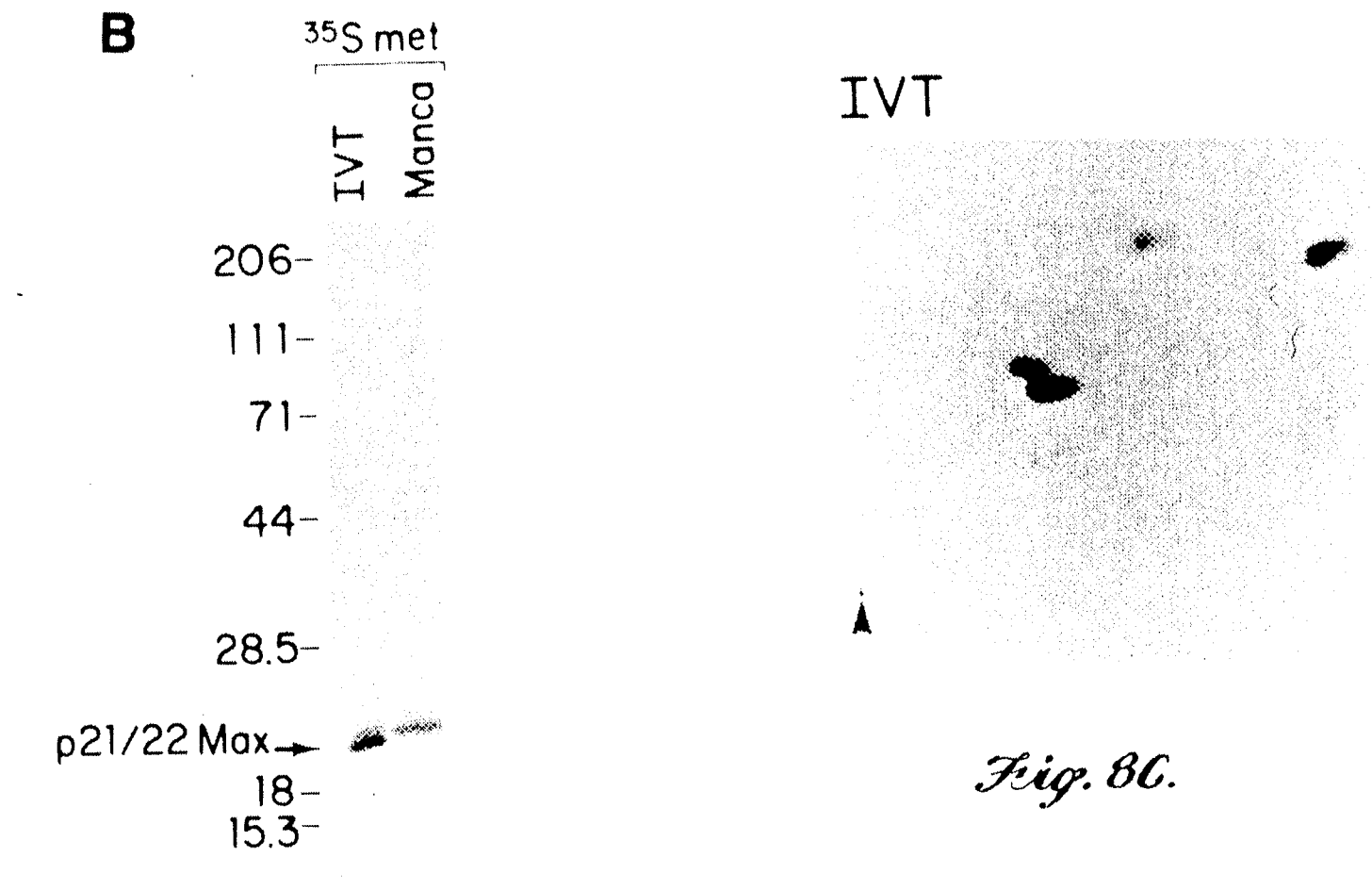
Figure 8F:
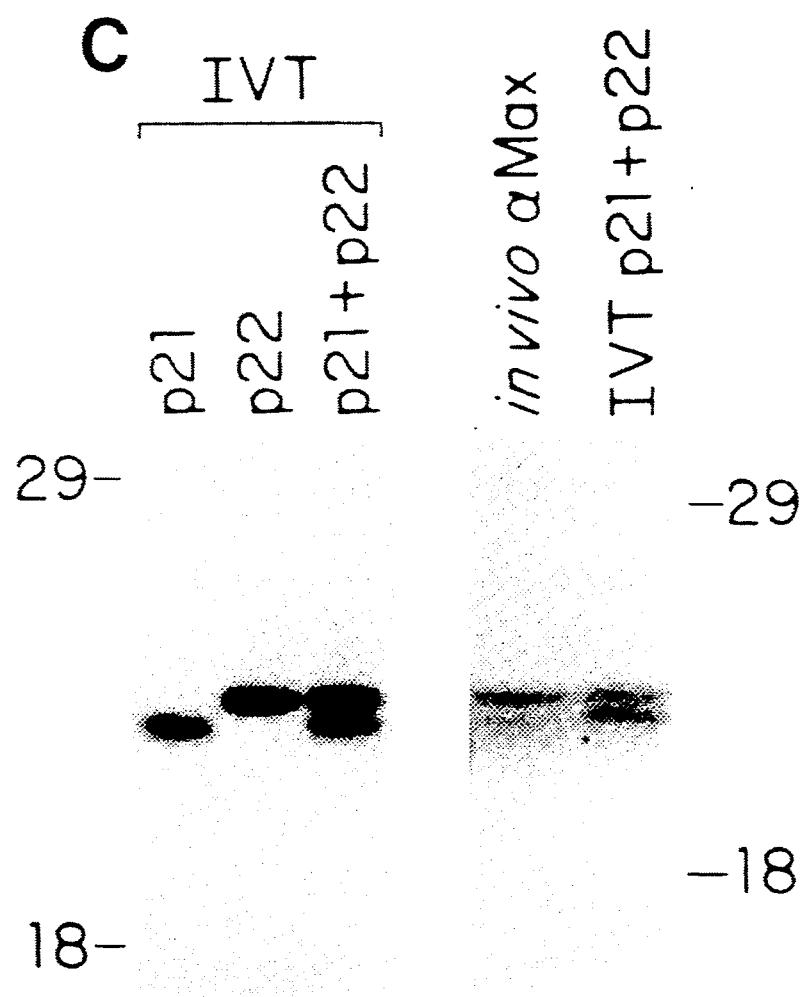
FIG. 8F compares Max p21 and Max p22 polypeptides purified from mammalian cells with synthetic Max polypeptides resulting from in vitro translation, as described in Example 5.
Figure 9I:
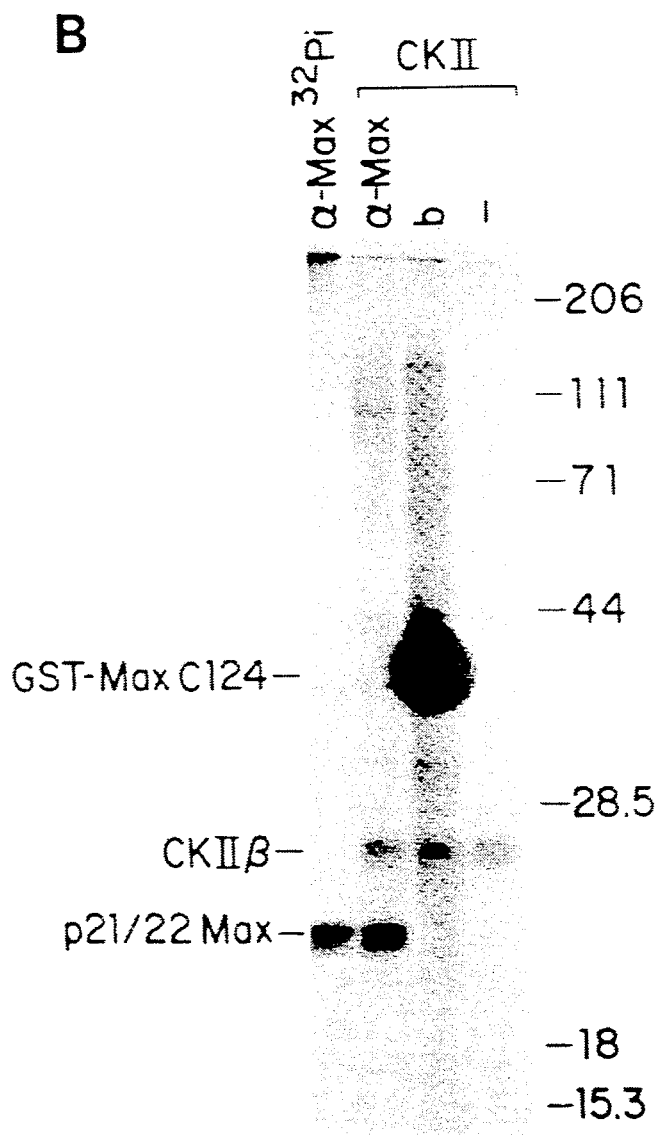
FIG. 9I portrays phosphorylation of Max by protein kinases involved in regulation of cell growth and replication, as described in Example 5.

As both p21 and p22 proteins can be identified in Manca as well as other cell types (FIG. 8A) (65) it was important to determine the relationship between the two proteins. They did not appear to be differentially phosphorylated forms of the same protein since phosphatase treatment did not resolve the p21/p22 doublet into a single species (65). Previous work had identified two Max cDNAs differing only by the addition of a 9-amino acid segment N-terminal to the basic region (60,61), In vitro translation of the two variant cDNAs shows that they differ in Mr by approximately 1K and that their individual electrophoretic mobilities correspond to those of p21 and p22 immunoprecipitated from Manca cells with anti-Max (FIG. 8F). These data suggest that p21 and p22 are Max proteins which differ by the 9-amino acid insertion. [The nine amino acid insertion would not be expected to contribute to the tryptic peptide pattern shown in FIG. 8B since the initiating N-terminal [$^{35}$S]methionine of Max is likely to be removed (R. Moerschell, S. Hosokawa, S. Tsunasawa, F. Sherman *J. Biol. Chem.* 265, 19639 (1990).] We conclude, on the basis of antigenicity, electrophoretic mobility, and two-dimensional peptide mapping analysis that p21 and p22 are encoded by max.

Referring to FIG. 8A in more detail, Max protein was immunoprecipitated from [$^{35}$S]methionine labeled Manca cells using anti-GST-MaxC124 (α-Max). Preimmune serum (Pre-imm) served as a background control, while excess immunogen (GST or GST-Max) was used to compete for specific anti-Max binding. Referring to FIGS. 8B-E, the left-hand panel shows SDS-PAGE analysis of the immunoprecipitated and in vitro translated proteins used for peptide maps of [$^{35}$S]methionine labeled protein comparing in vitro translated p21 Max (IVT) with in vivo labeled protein comparing in vitro translated p21 Max (IVT) with in vivo labeled p21/22 Max proteins (Manca). Referring to FIG. 8C, the two Max cDNA's (IVT p21 and p22) were translated in a reticulocyte lysate and compared in 2-dimensional SDS-PAGE with in vivo labeled Max polypeptides (in vivo α-Max).

Proteins belonging to the Myc family have long been characterized as nuclear phosphoproteins (see ref. 66). The Max is also nuclear can be demonstrated by immunofluorescence analysis of fixed HeLa cells. Specifically, indirect immunofluorescence staining was performed on fixed HeLa cells using previously described methods [D. K. Palmer and R. L. Margolis, *Mol. Cell Biol.* 5, 173 (1985)]. Briefly, cells were fixed with paraformaldehyde, permeabilized with Triton X-100, blocked with bovine serum albumin and incubated with affinity purified anti-Max or polyclonal and anti-Myc serum. Secondary antibody was fluorescein-conjugated goat anti-rabbit immunoglobulin.

Anti-Max produces granular nuclear staining exclusive of nucleoli, as observed for Myc (FIGS. 9A-H) (67). In addition both the p21 and p22 Max proteins appear to be predominantly nuclear as shown by cell fractionation experiments(65). That Max is a phsophoprotein was demonstrated by immunoprecipitation of radioactive p21/p22 from [$^{32}$PO$_4$]-labeled Manca cells (FIG. 8B). [In vivo [$^{32}$P]orthophosphate labeling as well as in vitro CKII kinase assays were performed as previously described (64).] Several major in vivo phosphorylation sites on c-Myc have been shown to correspond to those phosphorylated by casein kinase II (CKII) in vitro (64). Because Max also contains putative CKII consensus phosphorylation sites we determined whether CKII would phosphorylate Max in vitro by treating immunoprecipitated p21/p22 Max with purified CKII and γ-$^{32}$P-ATP. FIG. 8B shows that radiolabeled phosphate was specifically incorporated into both Max proteins. Tryptic phosphopeptide maps of in vivo [$^{32}$PO$_4$]-labeled Max are identical to those produced by CKII phosphorylation in vitro (65). Thus both Max and Myc proteins appear to be in vivo targets for CKII phosphorylation.

Referring to FIGS. 9A-H in more detail, subcellular localization of Max protein was assayed by indirect immunofluorescence on fixed Hela cells. Anti-Max and polyclonal anti-Myc immunoreactive proteins were detected with FITC-labeled goat-anti-rabbit Ig secondary reagent. Excess immunogen (block) or preimmune serum (Prei.) were used as negative controls, respectively. Phase-contrast images of the immunostained cells are shown to the right. Referring to FIG. 9I, Max polypeptides were immunoprecipitated from [$^{32}$P]orthophosphate labeled cells (α-Max$^{32}$Pi) or from unlabeled cells and phosphorylated in vitro with casein kinase II (CKII, α-Max). The immunogen (GSTMaxC124) served as an excellent substrate for CKII when added as a blocking reagent (b). Autophosphorylation of the β subunit of CKII ("-") is shown in the enzyme only control.

Myc proteins have extraordinary short half-lives, on the order of 20–30 minutes (63,68). In contrast both Max proteins are highly stable as demonstrated by the pulse-chase analysis shown in FIG. 10. No change in the levels of pulse-labeled Max are detectable 6 hours after removal of label, and Max appears stable even after a 24-hour chase period (65). In addition the relative levels of p21 and p22 Max are unaltered during the case period, consistent with the idea that the two proteins are independent translation products (FIG. 10).

Figure 10:
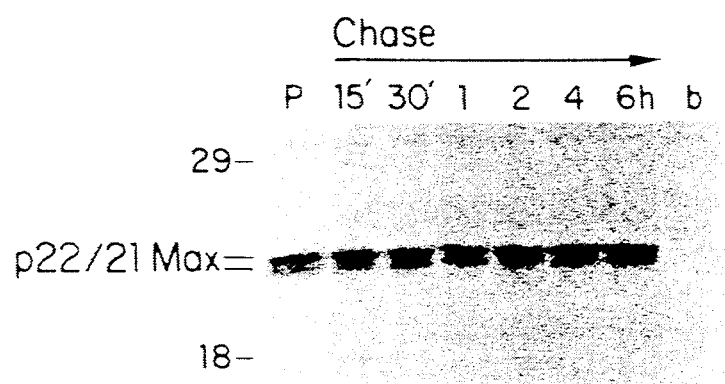
FIG. 10 presents the results of studies showing the stability of Max p21 and Max p22 in cells, as described in Example 5.

Referring to FIG. 10, to analyze protein stability, K562 cells were pulse-labeled with [$^{32}$S]methionine for 30 min (P), then "chased" for various lengths of time in the presence of excess nonradioactive methionine. Samples were immunoprecipitated under high stringency conditions with anti-Max and subjected to SDS PAGE. GST-MaxC124 was used to block specific immunoprecipitation (b).

The c-myc gene belongs to the class of immediate early genes in that while myc RNA and protein are virtually undetectable in quiescent cells they are transiently induced to high levels which several hours following mitogenic stimulation (69, 70). The peak of c-myc expression is followed by a decrease to a basal level that remains invariant throughout the cell cycle (71, 72, 73). Since c-myc and max are expressed in many of the same cell types (70), we asked whether max was also an immediate early gene by examining its expression levels following mitogen stimulation of serum-starved A31 Balb/c 3T3 cells. Specifically, quiescent A31 Balb/c-3t3 cells were serum stimulated as previously described [M. E. Greenburg and E. B. Ziff, Nature 311, 433 (1984)]. [$^3$H]thymidine incorporation was measured in triplicate from 24 well plates as described [D. F. Bowen-Pope and R. Ross, J. Biol. Chem. 257, 5161 (1982)]. In parallel, RNA was extracted by the acid-guanidinium thiocyanatephenol-chloroform procedure [P. Chomczynski and N. Saachi, Anal. Biochem. 162, 156 (1987)]. For Northern analysis, 10 μg of total RNA was hybridized with a 560 bp Max probe. For analysis of steady state protein levels, Max polypeptides were immunoprecipitated from unlabeled cultures (3×10$^6$ cells), blotted to nitrocellulose and reprobed with anti-Max and [$^{125}$I]Protein A.

Figure 11A:
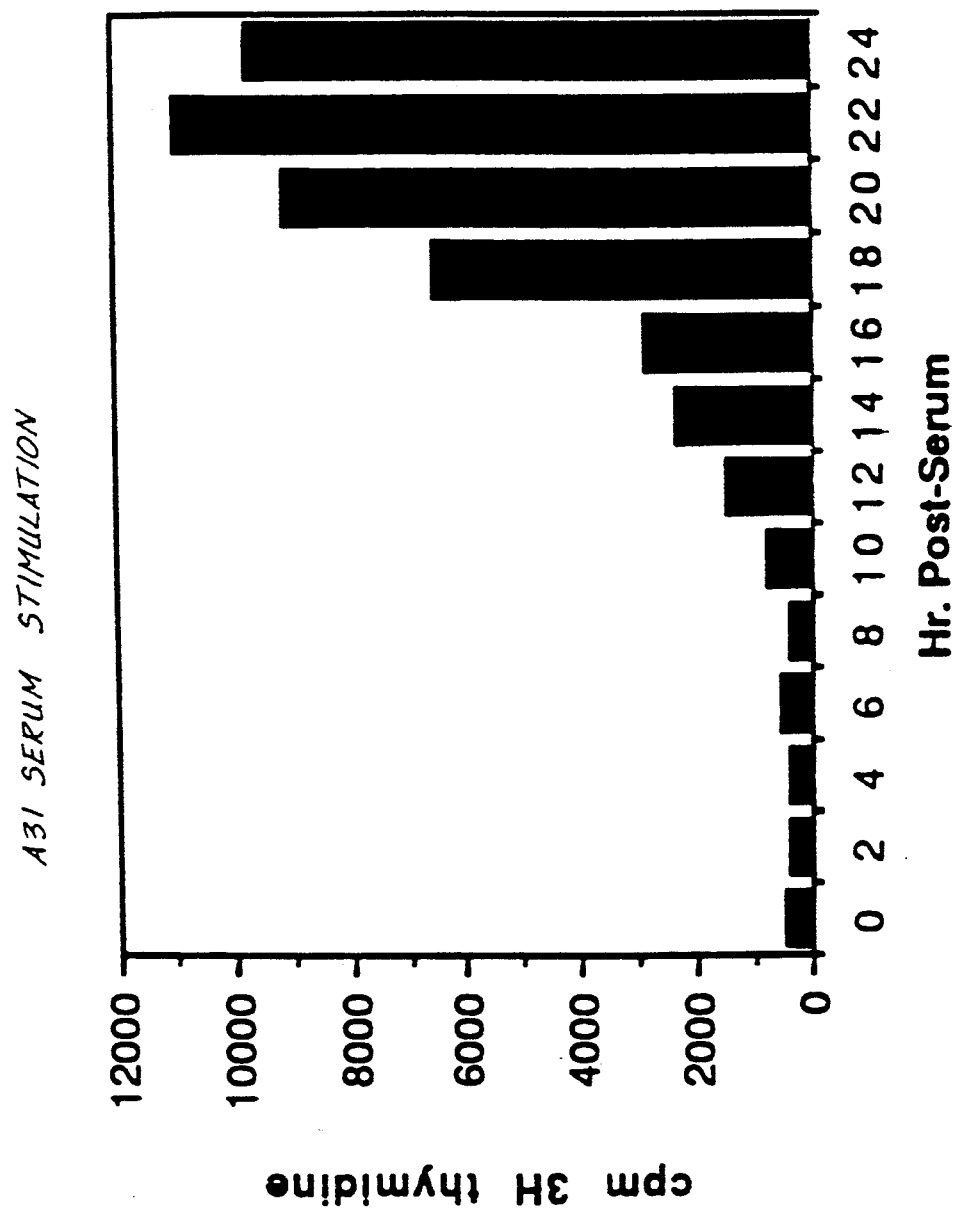
FIGS. 11A-C depict the relationship between the expression of the Max mRNA and polypeptides and growth and replication of mammalian cells, as described in Example 5.
Figure 11B:
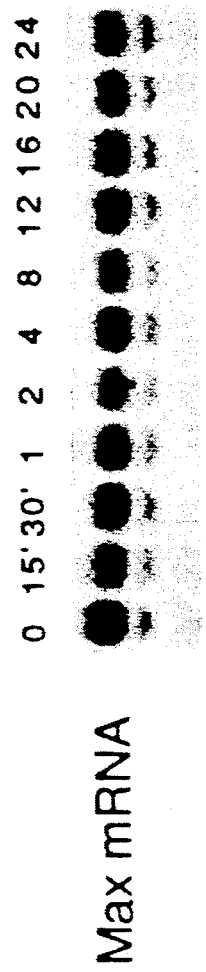
Figure 11C:

Steady state expression levels were determined by immunoblotting with anti-Max and by Northern blotting. Surprisingly both Max protein and max RNA were readily detected in quiescent culture (FIGS. 11A–C). Addition of serum clearly resulted in entry of cells into G1 and S phases, as judged by the 20 fold increase in 3H-TdR incorporation (FIGS. 11A–C) and an early increase in c-myc RNA (65). However no significant change in steady state max RNA or protein levels was observed. In addition Max expression levels are also not altered during the cell cycle as determined by centrifugal elutriation experiments(65). Therefore Max is not a member of the class of mitogen inducible genes and its levels of expression are independent of cell growth.

Referring to FIGS. 11A–C, A31 Balb/C 3T3 cultures were serum depleted for five days prior to stimulation with 15% fetal calf serum. [$^3$H]thymidine incorporation was measured in 2 hour pulse labelings following addition of serum (top). Max mRNA levels were analyzed by Northern blotting using the max cDNA as probe (60). An ethidium bromide-stained agarose gel was used to normalize the amount of RNA (10 μg, middle). To monitor steady state levels of Max protein, anti-Max immunoprecipitates (from unlabeled cells) were resolved by SDS-PAGE, transferred to nitrocellulose and reprobed with anti-Max and [$^{125}$I]-Protein a (bottom). Anti-Max antibody serves as a control for ]$^{125}$I]-Protein A-reactive immunoglobulin (Ab). The time course is in minutes (') or hours following serum stimulation.

In vitro c-Myc homodimerizes poorly, if at all (62, 74), while Max self-associates, but preferentially forms heterodimers with c-Myc (60). A major question raised by the in vitro demonstration of Myc:Max association is whether these proteins also interact in vivo. To answer this question we began by examining the conditions required for immunoprecipitation of Myc from cells. Analyses of Myc proteins by immunoprecipitation are frequency carried out using a mixture of non-ionic and ionic detergents which permit efficient extraction of Myc from nuclei and decrease non-specific binding of proteins to the immunocomplex (67, 75–78). As deoxycholate and SDS, however, disrupt the Myc:Max complex formed following in vitro translation of both proteins (65), in vivo association between Myc and Max might be similarly disrupted under standard "high stringency" immunoprecipitation conditions. Standard "high stringency" (HS) immunoprecipitations were carried out as previously described (76). Briefly, cells were lysed in Ab buffer (20 mM Tris-HCl, pH 7.4, 50 mM NaCl, 1 mM EDTA, 0.5% NP40, 0.5% deoxycholate, 0.5% SDS, 0.5% aprotinin), sonicated, clarified by centrifugation and subjected to immunoprecipitation with saturating amounts of antibody. Immunocomplexes were collected using protein A-Sepharose CL4B (Sigma). The beads were washed sequentially with RIPA buffer twice (10 mM Tris. pH 7.4, 0.15 M Nacl, 1% NP40, 1% deoxycholate, 0.1% SDS, 0.5% aprotinin), with high salt buffer (2M NaCl, 10 mM Tris, pH 7.4, 1% NP40, 0.5% deoxycholate) and finally with RIPA buffer.

Figure 12A:
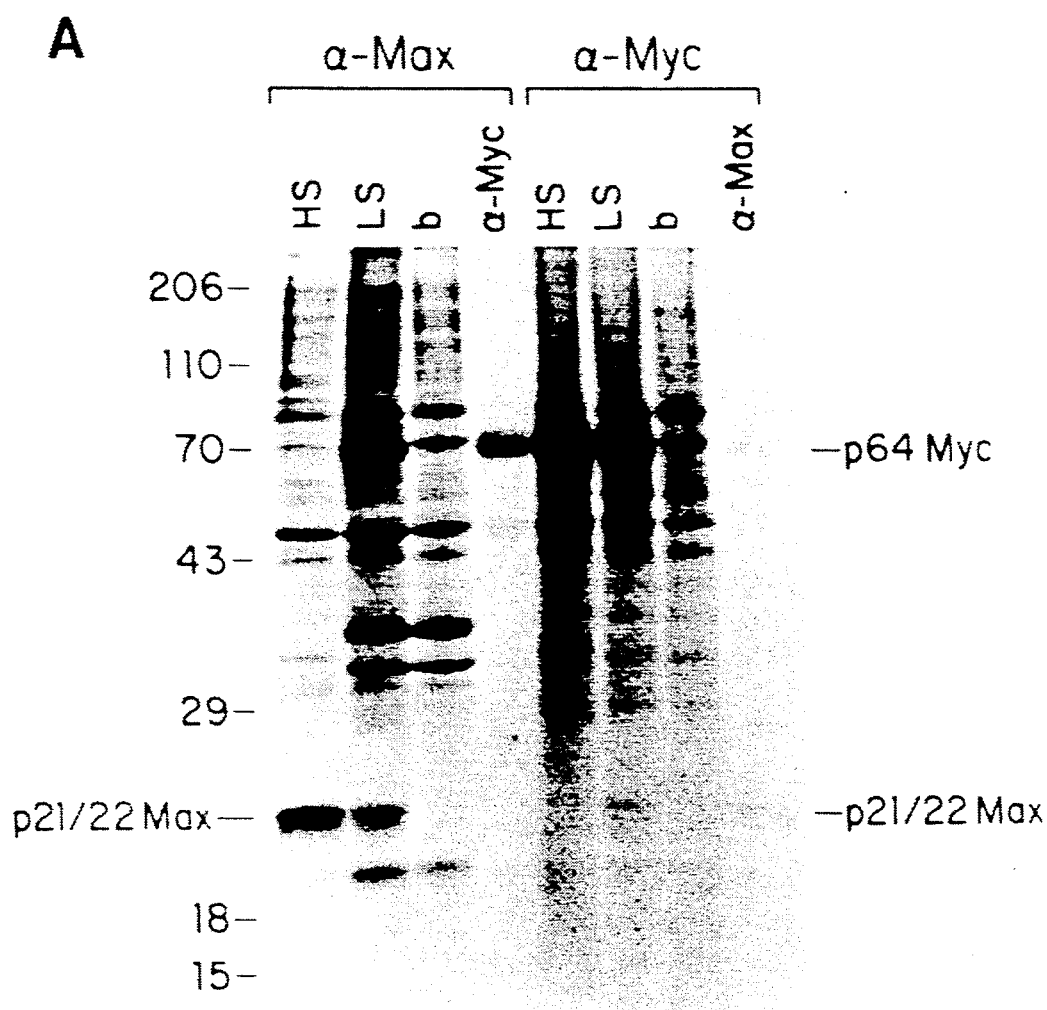
FIG. 12A depicts representative isolation and purification of Myc:Max complexes from mammalian cells and compares the results of high-stringency (HS) and low-stringency (LS) isolation conditions, as described in Example 5; and, FIGS. 12B-D depict representative isolation and purification of Myc:Max complexes from mammalian cells at low-stringency and purification of the Myc polypeptides from the isolated complexes at high stringency for determing Myc stability with a Myc:Max complex, as described in Example 5.

However, the Myc:Max oligomers formed in vitro were not disrupted in buffers containing only non-ionic detergents ("low stringency" conditions) (60). FIG. 12A shows a comparison of anti-c-Myc and anti-Max immunoprecipitates from Manca cells carried out under high and low stringency conditions. To increase the specific activity of the Max polypeptides for low stringency (LS) immunoprecipitations, cells were metabolically radiolabeled for 1 hour. All subsequent steps were done at 4° C. to stabilize Myc:Max complexes. Washed cells were lysed in PBS containing 1% NP-40 and a cocktail of protease and phosphatase inhibitors (0.2 mM phenylemthylsulfonyl fluoride, 0.7 μg/ml pepstatin, 0.5% aprotinin, 10 mM NaF, 50 mM β-glycerophosphate). The lysate (1×10$^7$ cells/ml) was sonicated on ice and microfuged to clarify. 5×10$^6$ cell equivalents were immunoprecipitated with 5 μg of anti-Max and collected on Protein A-Sepharose beads. Low stringency buffer was used to wash the precipitate four times including a single wash with 0.5M NaCl. The nonimmunoreactive component of the complex was eluted with 0.5 ml Ab buffer (described above), and precipitated under high stringency conditions. Samples were analyzed by SDS-PAGE under reducing conditions.

The immunocomplexes formed using high stringency buffer contain either p64 c-Myc or p21/22 Max (FIG. 12A, lanes HS). Reduction of the stringency of the buffer results in an increase in the background precipitation as well as the appearance p21/22 in the anti-Myc precipitate, and p64 in the anti-Max precipitate. (FIG. 12A, compare lanes LS). That these proteins are specifically precipitated is demonstrated by the ability of Max and Myc immunogens to competitively block their precipitation (FIG. 12A, compare lanes b and lanes LS), while the elevated background is unaffected. Furthermore, FIG. 12A, (α-Myc lanes) shows that anti-Myc can cleanly precipitate Myc protein released from a low stringency anti-Max immunocomplex by addition of SDS and deoxycholate. Similarly, anti-Max can precipitate Max protein released from the anti-Myc complex in the same manner (FIG. 12A, α-Max lanes). The ability of the anti-Myc and anti-Max sera to precipitate the complex without disrupting it is consistent with our results on Myc:Max oligomers formed in vitro (60). That Max and Myc can be coimmunoprecipitated from cells under nondisassociating conditions suggests that these two proteins do interact in vivo. Similarly, we can demonstrate association between N-Myc and Max as well as between different retrovirally encoded v-Myc proteins and Max (65).

Considering the highly stable nature of Max it was of interest to determine whether the short-half life of c-Myc might be affected by its association with Max. Myc protein stability was evaluated by pulse-chase experiments using BK3A cells, a chicken bursal lymphoma cell line in which Myc protein metabolism has been extensively studied (68). Following the pulse label, and at different time points during the "chase" period, the cells were lysed under low stringency conditions and Myc proteins immunoprecitated under high stringency conditions with anti-Myc to determine the total amount of radiolabeled Myc present (FIG. 12B). Specifically, for analysis of protein and complex stability, cells were pulse-labeled with [$^{35}$S]methionine for 30 min, washed free of unmetabolized radiolabel, and chased in the presence of excess cold methionine (0.5 mM). At specified time points, lysates were prepared in low stringency buffer, immunoprecipitated under either high or low stringency conditions and analyzed by SDS PAGE.

Figure 12C:
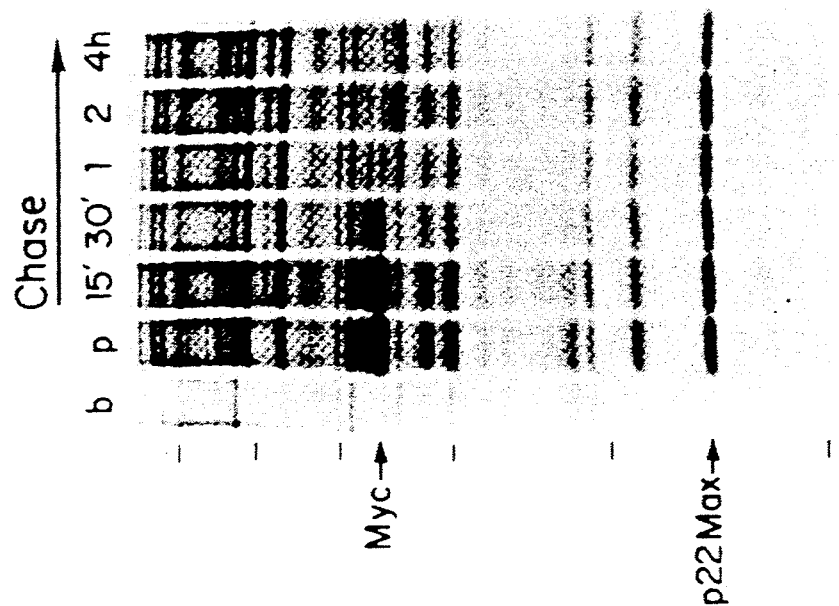
Figure 12B:
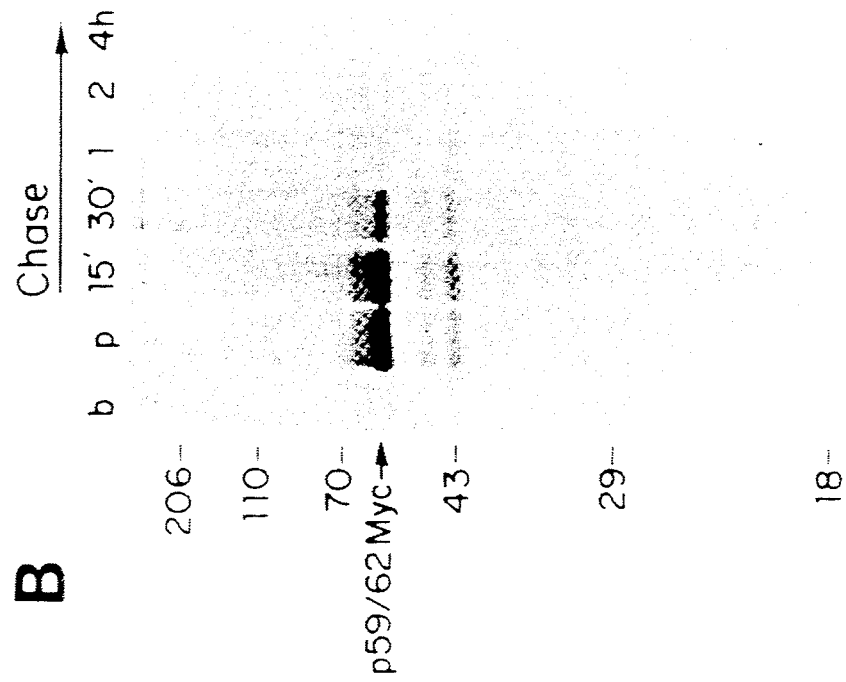
Figure 12D:
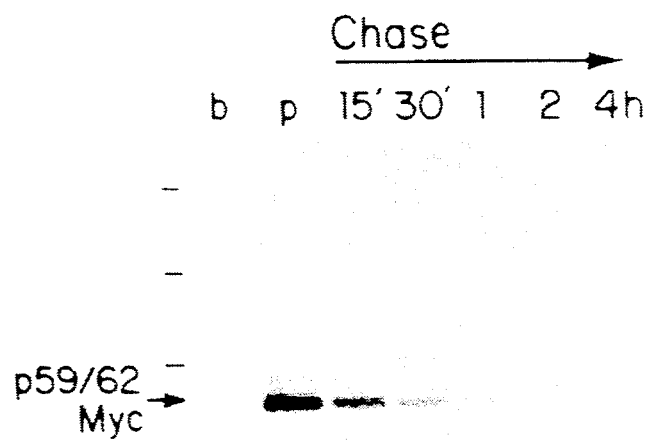

In parallel, the amount of labeled Myc protein associated with Max was determined by immunoprecipitation with anti-Max under the low stringency conditions (FIG. 12C). Although Myc protein can be resolved under these conditions we verified the amount of Myc present in the Max complex by treating the a-Max immunocomplex with high stringency buffer followed by reimmunoprecipitation with anti-Myc (FIG. 12D). The results clearly show that the majority of the newly synthesized Myc protein is present in the complex with Max and, furthermore, that Myc's half-life is unchanged by its association with Max. It is important to bear in mind however that these low stringency lysis conditions may not efficiently extract all of the Myc protein (65).

Referring to FIG. 12A in more detail, [$^{35}$S]methionine labeled Manca cell lysates were immunoprecipitated under the described high (HS) or low (LS) stringency detergent conditions. An excess of the cognate immunogen was used to block specific immunoprecipitation (b). To verify the identity of the coprecipitated component, low stringency Myc:Max complexes were disassociated with SDS and reimmunoprecipitated under high stringency conditions with the converse antiserum (α-Myc or α-Max). Referring to FIGS. 12B, the stability of Myc protein was analysed by pulse-chase labeling (30 min. pulse label) of BK3A, an avian bursal lymphoma cell line. Low stringency extracts of Myc protein were directly immunoprecipitated under high stringency conditions (HS α-Myc) or coprecipitated in a complex with Max (LS α-Max). To verify the levels of Myc protein found in anti-Max immunoprecipitates, low stringency complexes were disassociated with ionic detergent and reprecipitated with anti-Myc (LS α-Max→HS α-Myc). Identical exposures are shown.

Here we have identified the Myc-binding protein Max in vivo and have shown that Myc and Max are associated in the cell. Most if not all of the newly synthesized Myc passes through an in vivo complex with Max: a result consistent with the dimerization properties of Myc and Max observed in vitro (60, 62, 74). The half-life of Myc protein is not altered by its association with Max although Max itself is an extremely stable nuclear phosphoprotein.

Max protein and RNA are readily detected in quiescent cells at levels that are unchanged by serum stimulation or cell cycle phase. However in response to mitogenic stimulation Myc levels increase from near background in quiescent cells to a peak of expression which then declines to a basal level prior to S phase (69). During the cell cycle Myc synthesis and rapid turnover are maintained at a constant basal level (71, 72, 73). Therefore in contrast to Myc, Max expression appears to be independent of the growth state of the cell.

The contrasting properties of Myc and Max suggest first, that it is the abundance of Myc which limits or drives formation of heterocomplexes, and second that Myc function is mediated through a Myc:Max heterocomplex. Short-lived Myc monomers may be continually competing with Max homodimers for interaction with Max. One possibility is that Max homodimers function in a manner distinct from Myc:Mas heterodimers and that Myc serves to transiently "switch" Max between its different activities. Thus the extraordinary degree to which Myc expression is regulated, and the loss of this regulation during oncogenic activation (see 78), may critically influence the balance hereto and homodimer function. It will be of interest to determine whether complex formation of function is further regulated by CKII phosphorylation, the expression pattern of two alternative Max proteins, or potential interactions with other cellular components.

In retrospect, the experiments described in the prior art lead to a picture of Max as a highly conserved, stable nuclear phosphoprotein expressed in many cell types. Although numerous immunoprecipitation experiments have been carried out over the last five years with anti-Myc antibodies, Max had never been previously identified as being associated with Myc. One explanation may be related to the immunoprecipitation conditions used to study Myc, which are usually high stringency (i.e., with multiple detergents) in order to efficiently extract Myc from nuclei and reduce background. To determine whether Myc and Max interact in vivo we carried out immunoprecipitations with either anti-Myc or anti-Max antibodies under low stringency conditions. Such conditions result in an increase in background, but among the proteins precipitated Myc and Max are visible. Their presence was confirmed by solubilizing the immunocomplexes using high stringency buffer followed by a second immunoprecipitation with anti-Myc and anti-Max. The results clearly demonstrate that both Myc and Max are present in anti-Max and anti-Myc immunocomplexes.

Our experiments show that Myc and Max are likely to associate in vivo and that a significant fraction of the population of each protein is involved in the interaction. These findings raise a number of questions relevant to the physiological function of Myc. Since Max appears to self-associate (60), while Myc homodimerizes weakly if at all, it is possible that populations of relatively stable Max homodimers and unstable Myc:Max heterodimers exist in cells. Max or Myc alone have been shown to bind the sequence CACGTG, presumably as homodimers (62). Recent experiments indicate that Myc:Max heterodimers bind this sequence more strongly (60) and that the binding specificity is unchanged (K. Blackwell and E. Blackwood, unpublished data). Even through homodimers and heterodimers might bind the same sequence, the difference in binding strength, as well as the very nature of the complex bound to DNA (i.e., the heterocomplex obviously has a structure quite distinct from the homodimeric complex), could have profound consequences. Whatever these effects may be they are probably largely dependent on the levels of Myc protein. This is because Myc may be competing for binding with Max:Max homodimers and because Myc is degraded so rapidly while Max is highly stable. Thus, even small changes in Myc regulation at transcriptional or post-transcriptional levels might be biologically important by affecting the concentration of heterodimeric complexes.

If we assume that Myc exerts its proliferation promoting function through its interaction with Max then events that interfere with this interaction are likely to modulate Myc's function. This would include post-translational alterations, such as phosphorylation, which might after Myc's ability to associate with Max, or the presence of other proteins interacting with Myc, Max, or both. Such proteins acting at the level of complex formation might act as tumor suppressor proteins. Alternatively, such proteins could also function after the complex is formed: to attenuate its activity or prevent its interaction with other positively acting factors. Finally, the possibility that Max is itself a negative regulator of growth needs to be considered. One scenario is that Myc diverts Max's proliferation suppressor activity into a proliferation promoting activity by forming an active complex with it. The finding that Myc and Max can interact specifically both in vitro and in vivo now permits a direct test of these ideas.

Constitutive high-level myc expression has previously been shown to lead to changes in growth rate (79, 80), increased sensitivity to growth factors (81–83), inhibition of differentiation of numerous cell types (84–87), and the capacity to cooperate with other activated oncogenes in the tumorigenic conversion of normal cells (88–90; for review, see 91). Thus, it is not difficult to rationalize even subtle changes in myc regulation with an increased potential for neoplastic growth.

The findings that c-Myc has sequence-specific DNA-binding activity and is also capable of specific association with another HLH-Zip protein puts it firmly in the same general functional class as the bHLH and bZip transcription factors. Nonetheless, Myc would seem to be structurally distinct from these other proteins, in that it possesses contiguous HLH and zipper domains and appears to have its own restricted set of interactions. Whether this restricted set includes the other HLH-Zip proteins remains to be determined. We surmise that both Myc:Myc and Myc:Max complexes function in transcription activation or repression through their specific DNA-binding activities, and that formation of complexes is dependent on the relative levels of expression of myc and max genes. This model does not exclude a role for Myc in DNA replication, since its transcriptional activity could well affect the expression of genes involved in induction of S phase. Alternatively, Myc might be more directly involved in DNA synthesis through binding to the class of replication origins that contain enhancer or promoter elements (see 92). The delineation of the specific interactions of Myc may provide a means to resolve these possibilities and elucidate the role of Myc in normal and neoplastic cell behavior.

THIRD SERIES OF EXAMPLES

Here we have identified the Max-binding protein Mad in vitro and have shown that Mad can compete binding of Myc to Max.

The Materials and Methods and Discussion sections for the Third Series of Examples appears at the end of EXAMPLE 11.

EXAMPLE 6

Identification of a New Max Binding Partner

Figure 13A:
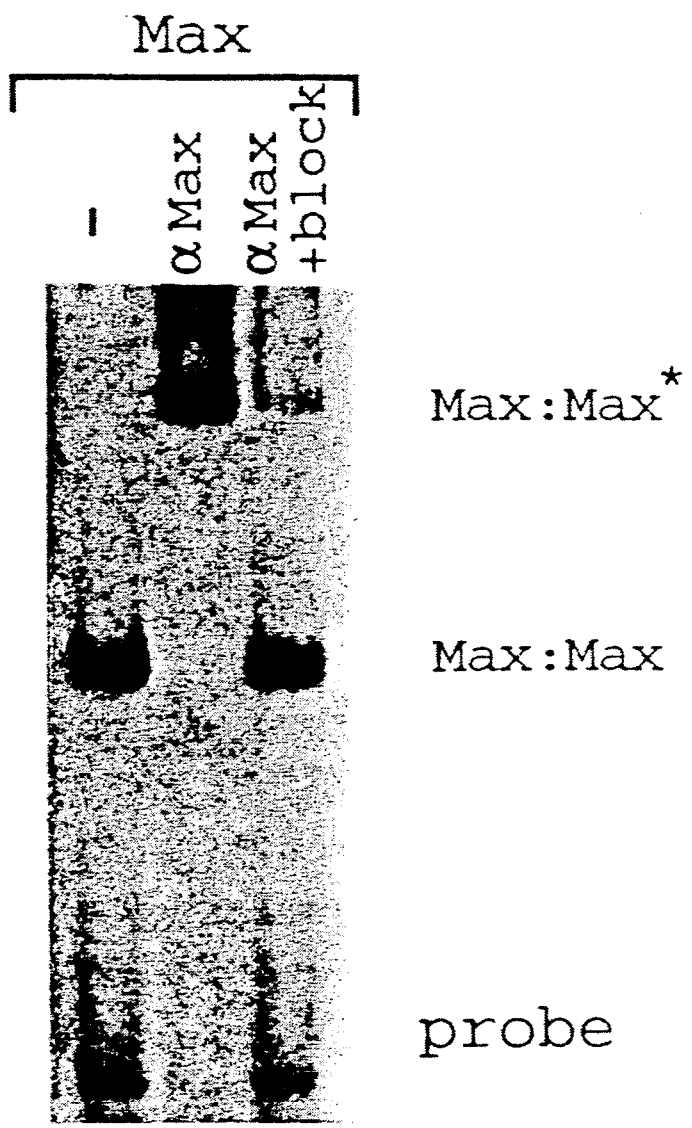
FIG. 13A-C show autoradiograms of gels in which altered electrophoretic mobility of Max:oligonucleotide complexes was used to identify polypeptides that bound specifically with Max. The ability of Max purified from sf9 cells to bind the CM-1 binding site was assayed by an electrophoretic mobility shift assay as described below, (FIGS. 13A and 13B).

There are several findings that suggest the potential for a protein, other than Max, that could regulate Myc activity: Myc expression is regulated during entry to and exit form the cell cycle while Max expression is constitutive, vast differences in the stability of the two proteins and differences in the cell type and tissue distribution. One might speculate that a protein that could alter the activity or the availability of Max might influence Myc function. Therefore, we have used purified Max protein to screen an λgt11 expression library for Max binding partners. Max protein was overexpressed using the baculovirus expression system. Sf9 cells were infected with a recombinant baculovirus containing the Max cDNA insert and Max protein was purified to apparent homogeneity from a cytoplasmic cell extract using cation and anion exchange chromatography. We tested this protein preparation for Max DNA binding activity using the electrophoretic mobility shift assay [EMSA] (FIG. 13A).

The purified Max preparation formed a retained complex in the presence the Myc/Max binding site, CM-1. This complex was a result of Max binding because it is further retained in the gel matrix in the presence of an anti-peptide antibody specific for Max. The binding activity in the Max preparation was specific for the CM-1 oligo as it was competed by increasing amounts of unlabeled CM-1 but not by equivalent amounts of a unrelated oligo (FIG. 13B).

The purified Max was also able to form heterodimers with Myc and was therefore competent for dimerization as well as DNA binding (data not shown). We concluded that the insect cell expressed Max protein was highly active in DNA binding and heterodimerization and therefore suitable to use as a probe to screen for potential max binding partners.

Max was first identified by screening an expression library was an iodinated fusion protein containing the C-terminal 92 amino acids of Myc (FIRST SERIES OF EXAMPLES, above). We have used a similar approach to screen for Max binding partners however, we have used casein kinase II (CKII) and [γ-$^{32}$P]ATP to label Max. The Max protein has two CK II phosphorylation sites in the n-terminus (serines 2 and 11) and a cluster of 5 serine residues near the C-terminus of the molecule. Max protein from insect cells is partially phosphorylated but can still be labeled to high specific activity by CKII in vitro (data not shown). Furthermore, the β-subunit of CKII is known to be autophosphorylated but was not labeled under our reaction conditions and therefore Max was the only labeled protein in the probe preparation (data not shown). The labeled Max was used to screen a λgt11 expression library constructed from the baboon pre-B cell line 594-S. In the initial screen $10^6$ individual phage were plated and screened. Labeled Max bound to a bacterial lysate infected with a phage (Max 14) that encoded Max (above) (FIG. 13C).

Figure 13B:
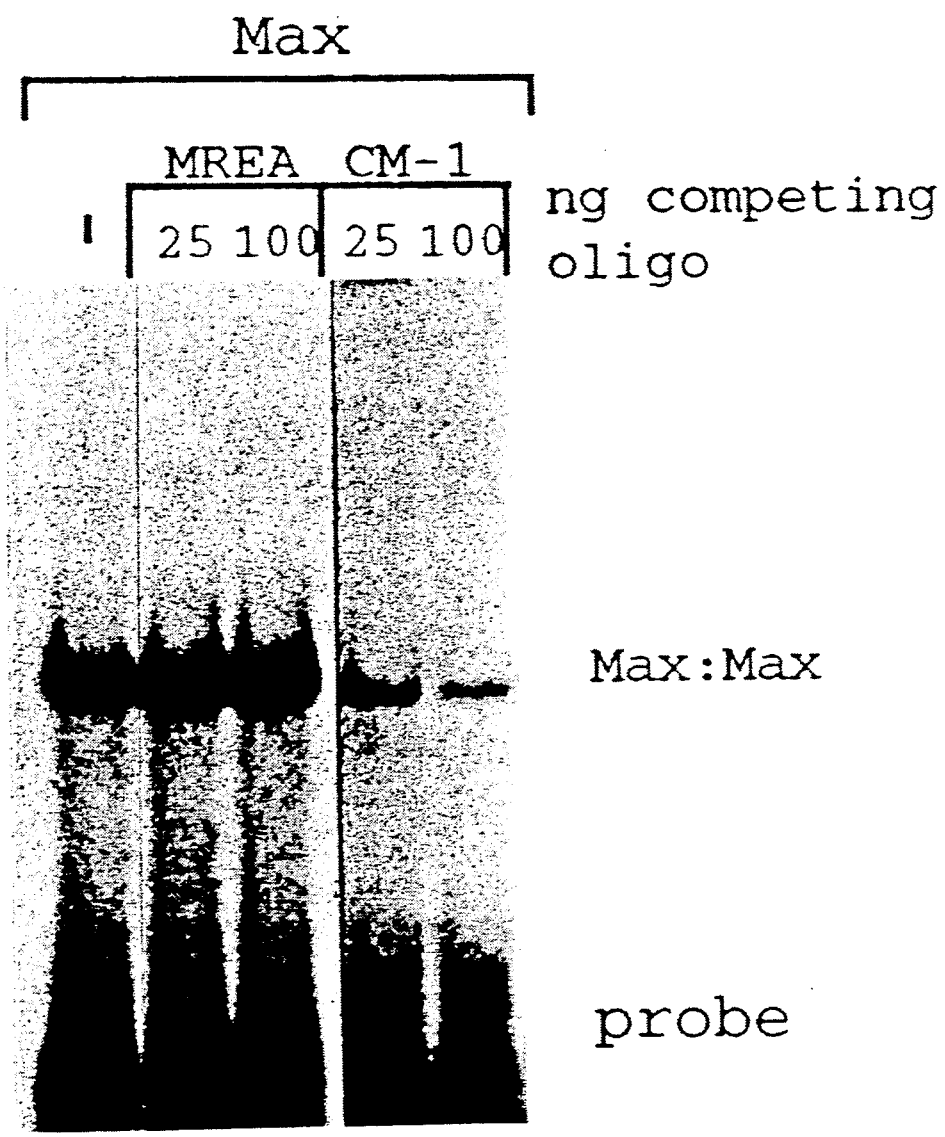
Figure 13C:
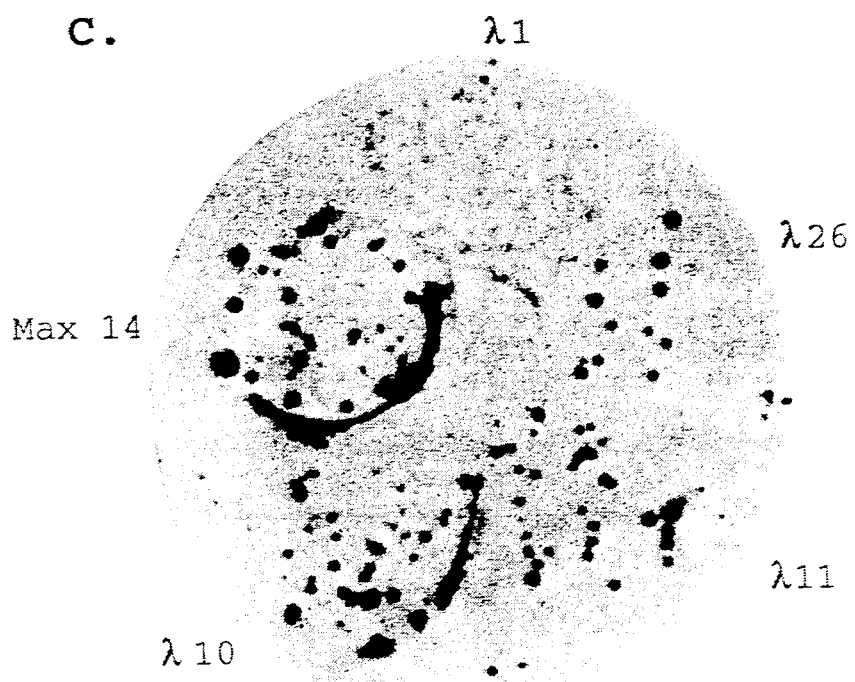

FIGS. 13A–C Identification of Max binding partners. The ability of max purified from Sf9 cells to bind the CM-1 binding site was assayed by the electrophoretic mobility shift assay (FIG. 13A and 13B).

FIGS. 13A shows Max DNA binding assayed in the absence (−) or the presence of a Max specific anti-peptide antiserum (αMax). αMax+block indicates the inclusion of the immunizing peptide in the binding reaction.

FIGS. 13B shows Max binding activity assayed in the presence of unlabeled CM-I or an unrelated oligonucleotide, MREA. The amount of competing oligonucleotide is give in ng; "−" denotes no unlabeled oligonucleotide in the binding reaction. The position of the free probe and the Max homodimer mobility shift is as marked. The asterisk denotes the antibody:Max:Max complex.

FIG. 13C shows $^{32}$P-labeled Max binding to a filter containing phage lysates from different gt11 lambda clones. Max 14 wash previously identified as a binding partner for Myc. λ1 encoded a lacZ fusion protein with no specific Max binding activity and served as a negative control in this experiment.. λ10, 11, and 26 encoded lacZ fused to potential Max binding partners.

Three additional phage encoded proteins that were positive for Max binding through multiple rounds of screening and purification (FIG. 13C). It was likely that these clones encoded Max or one of the Myc family members fused to lacZ. λ10 and 11 hybridized to a Max DNA probe and encoded a protein that was immunologically related to Max. λ26 was not related to any of the Myc family members by DNA hybridization and therefore represented a potentially new binding partner of Max. We have subcloned the cDNA insert from λ26 termed it Mad-1 (Max associated dimerization). The baboon Mad-1 cDNA had a 186 amino acid open reading frame fused to lacZ. Using this partial baboon Mad-1 cDNA from λ26 we have isolated a human Mad-1 cDNA from a embryonic lung cDNA library (FIGS. 14A–B).

FIGS. 14A–B Nucleotide and amino acid sequence of the human Mad-1 cDNA. The nucleotide and the amino acid sequence of the coding region of the 3.2 kb human Mad1 cDNA from the WI26 λgt10 library is shown. Nucleotide positions are indicated. Amino acid positions are denoted by bold faced numbers and in frame stop codons are shown. The basic region homology is boxed and the positions of the positively charged residues in this region are marked by +. The shaded boxes locate helix I and helix II. The amino acids that form the hydrophobic heptad repeat are given in bold underline text. The region rich in acidic amino acids is located between amino acids 152 and 189.

Comparison of the baboon and the human CDNA sequences revealed no amino acid differences. We believe that the human cDNA is full length because the first AUG encoded in the RNA is in good translational context and is proceeded by an in frame amber stop codon. In addition, the human Mad-1 cDNA is 3.2 kb in size in agreement with the size of the Mad-1 RNA as determined by northern blotting(data not shown).

The Mad-1 cDNA encodes a protein of 221 amino acids with a predicted molecular weight of 25,200 daltons. A search of the protein data base with the predicated Mad-1 amino acid sequence revealed no identities suggesting that it is a previously unrecognized protein. However, the Mad-1 protein sequence is a near perfect match to the consensus sequence determined for the basic-helix-loop-helix (b-HLH) family of transcription factors (FIGS. 15A–B).

Mad-1 is most similar to the Drosophila proteins extramacrocheatae and hairy had has some similarity to the Myc family members. The similarity to the Myc proteins is limited to the basic region and suggests that Mad-1 is not another member of the Myc family. Mad-1 has little similarity outside the conserved amino acids of the b-HLH consensus to Max or two other b-HLH proteins (USF and TFE3) that bind the CACGTG element. Like Myc and Max, Mad-1 has a heptad repeat of hydrophobic amino acids following helix II of the HLH domain. This repeat of amino acids might form a structure similar to the coiled-coil leucine zipper domain that has been shown to mediate dimerization other transcription factors with similar domains. The b-HLH-zipper structure of Mad-1 is a similar to those found on Max and Myc but the structural organization of the three proteins is quite different (FIG. 15 C).

Figure 15C:
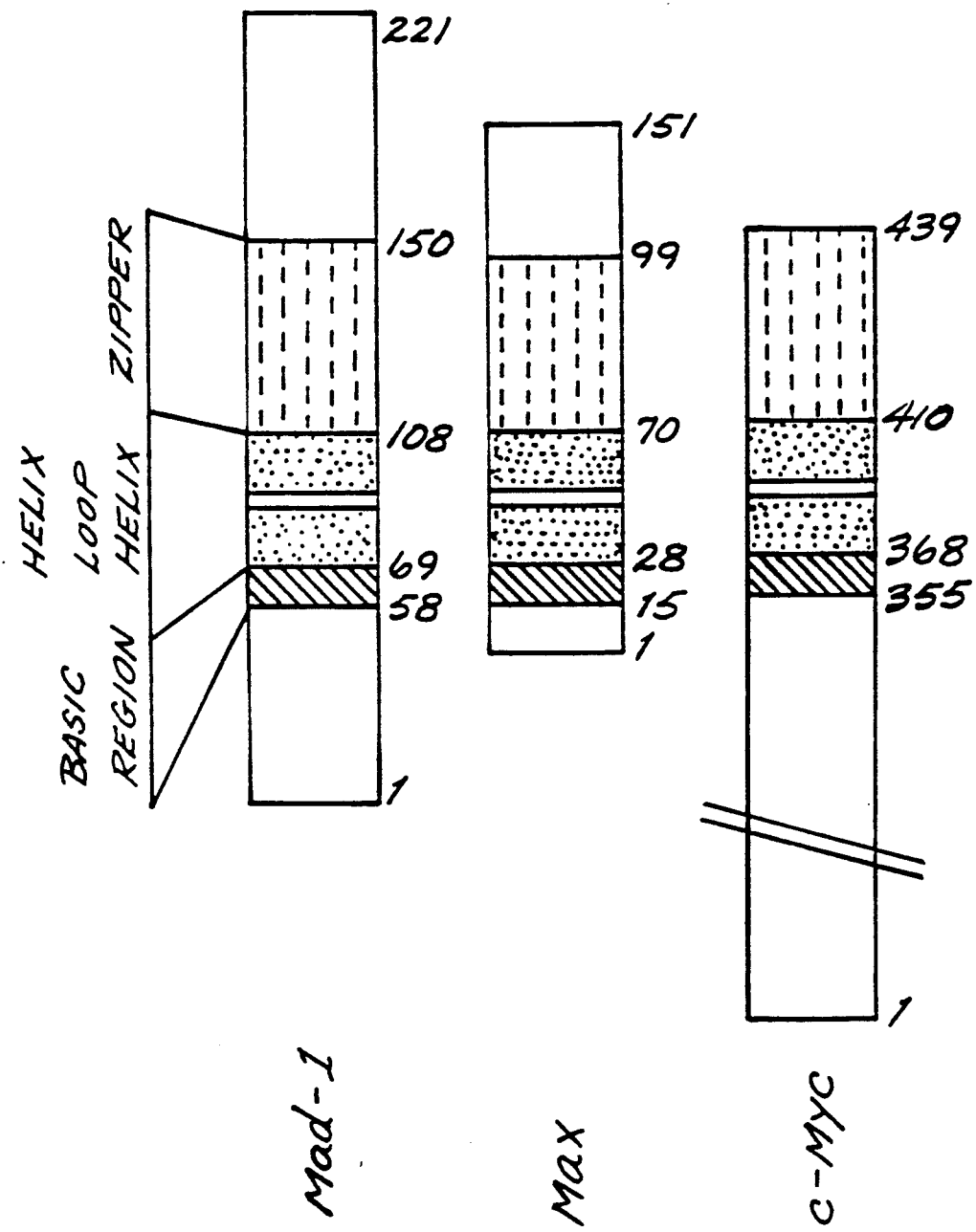
FIG. 15C shows the organizational structure of the Mad-1, Max and Myc polypeptides. The numbers indicate amino acid position. The basic region, helix-loop-helix, and leucine zipper homologies are as indicated by cross-hatching, shading, and dashed-lines, respectively.

FIGS. 15A–C. Comparison of Mad-1 to other b-HLH proteins. The predicated amino acid sequence of Mad-1 is compared to other members of the b-HLH family of transcription factors and to the b-HLH consensus (FIGS. 15A–B). The amino acids are denoted by the single letter code. The Drosophila proteins EMC (extramacrocheatae) and hairy were found to be most similar to Mad-1 is searches of the data base while TFE3 and USF both recognize the same DNA binding site (CACGTG) as Myc and Max. The matches to the b-HLH consensus are shaded and the residues that form a heptad repeat of hydrophobic amino acids are shaded and boxed. The primary structure of a generalized b-HLH-zipper protein is shown schematically at the bottom of the panel. The structural organization of Mad-1, Max and Myc is shown in FIG. 15C. The numbers indicate amino acid position. The basic region, helix-loop-helix, and leucine zipper homologies are as indicated.

In Mad-1, the b-HLH-zipper region is localized to the middle of the primary amino acid sequence. By contrast, the b-HLH-zipper domains of Myc and Max are localized to the carboxy and the amino termini, respectively. It is not clear if the different structural organization of these proteins has functional consequences.

Myc and Max are both nuclear phosphoproteins. The similarity of Mad-1 to these proteins suggests that it should be localized to the nucleus as well. There is a potential bipartite nuclear localization (Dingwall and Laskey, (1991) signal in Mad-1 found between amino acids 20 and 50. Myc and Max are in vivo and in vitro substrates for casein kinase 11 (CKII). The COOH-terminus of Mad-1 is rich in negative charge (amino acids 152–189) and contains several potential CKII phosphorylation sites. This region may function as a transcriptional activation domain similar the acidic region of Myc and other transcription factors. If utilized, CKII phosphorylation of this region would increase the negative charge density of this region even further.

EXAMPLE 7

Mad-1 Binds Specifically to Max

Figure 16A:
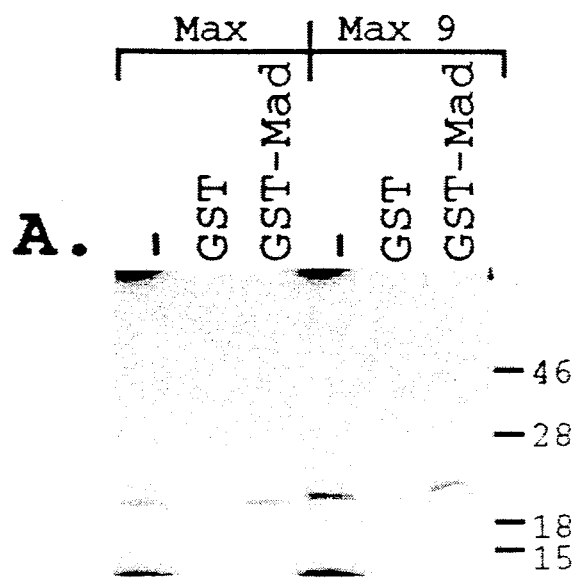
FIGS. 16A-F, show autoradiograms of gels in which Mad-1 was mixed with other b-HLH polypeptides to test its binding specificity as described in the THIRD SERIES OF EXAMPLES, below. The results of the electrophoretic gel shift experiments show the specificity of Mad-1 binding to Max. In this experiment, RNAs encoding the proteins given at the top of each panel (e.g., Max RNA and Max 9 RNA in FIG. 16 Panel A) were translated and labeled with $^{35}$S-methionine in vitro in the presence of either purified glutathione-S-transferase (GST) or glutathione-S-transferase fused in frame to baboon Mad-1 cDNA (Mad). The proteins bound by GST or GST-Mad were analyzed on SDS polyacrylamide gels. The lanes marked "-" indicated translation products obtained in the absence of added purified GST or GST-Mad protein.

In Order to test the binding specificity of Mad-1 we have constructed a fusion protein between the COOH-terminal 186 amino acids encoded by the baboon Mad-1 cDNA and glutathione-s-transferase. This fusion protein is expected to contain the domains of the Mad- 1 protein required heterodimer formation and DNA binding. Either the purified fusion protein (GST-Mad) or purified glutathione-s-transferase (GST) was added to in vitro translation reactions programmed with RNAs encoding either Max or Max 9. Following translation the products were allowed to bind to glutathione-sepharose. The beads were washed extensively and the bound proteins were analyzed on SDS-PAGE gels (FIG. 16A).

Figure 16B:
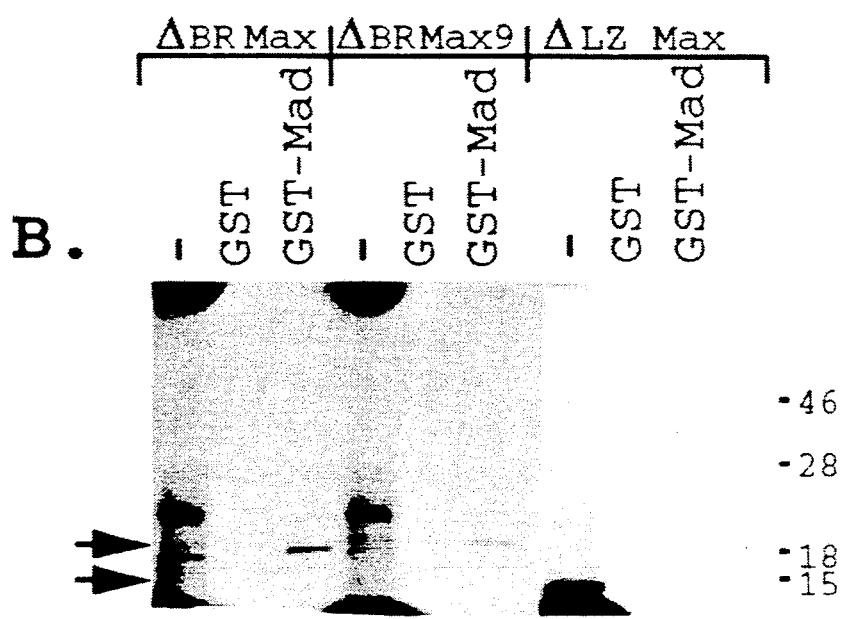

Both Max and Max 9 were retained on the glutathione beads if they were translated in the presence of GST-Mad; however, neither protein was retained in they were translated in the presence of GST alone. This indicated that the Max proteins were retained on glutathione beads through the Mad segment of the fusion protein. If the Mad-1 cDNA was translated and assayed in a similar manner there was high background binding to GST alone; however, there was no Mad-1 binding to GST-Mad above this background level (data not shown). This suggested that Mad-1 formed homodimers poorly. Because Mad1 seemed to bind the glutathione-sepherose non-specifically we were concerned that it may have a generalized non-specific binding activity. We, therefore, have determined which regions of Max are needed for interaction with GST-Mad. Various Max mutants were tested for binding to GST-Mad or GST (FIG. 16B).

Proteins that had the basic region either Max or Max 9 deleted both bound to GST-Mad. By contrast, deletion of the last two leucines from the Max hydrophobic heptad repeat abolished binding to GST-Mad (i.e., $leu_{86}$ and $leu_{93}$; FIGS. 2C–D). These two leucines were also required for Max heterodimerization with Myc. These data suggest that the heptad repeats of hydrophobic amino acids in Mad-I and Max are responsible mediating their interaction. We have not tested the role of the HLH motif in Mad-1:Max interaction but based on mutational analysis of other members of the b-HLH family the HLH region is expected to play a role in dimerization as well.

Figure 16C:
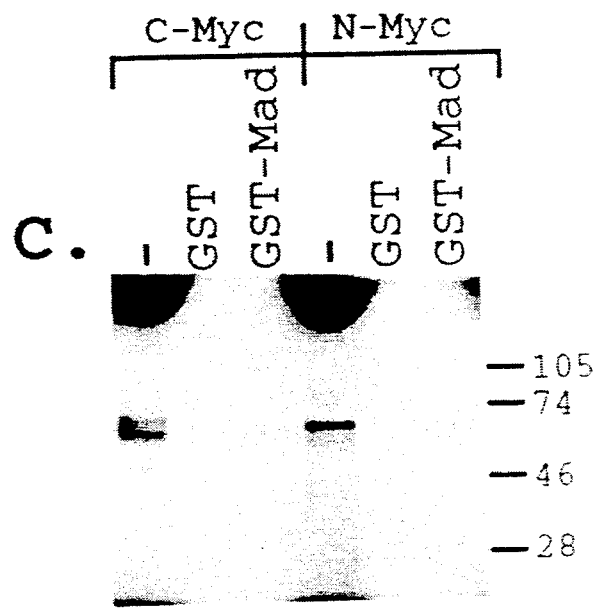

Because Mad-1 and Myc both bind to max it seemed reasonable that Myc and Mad-1 might also interact. Using conditions where we readily detected Max interaction with GST-Mad there was no binding of C- or N-Myc to GST-Mad was detected above background (FIG. 16C).

Figure 16D:
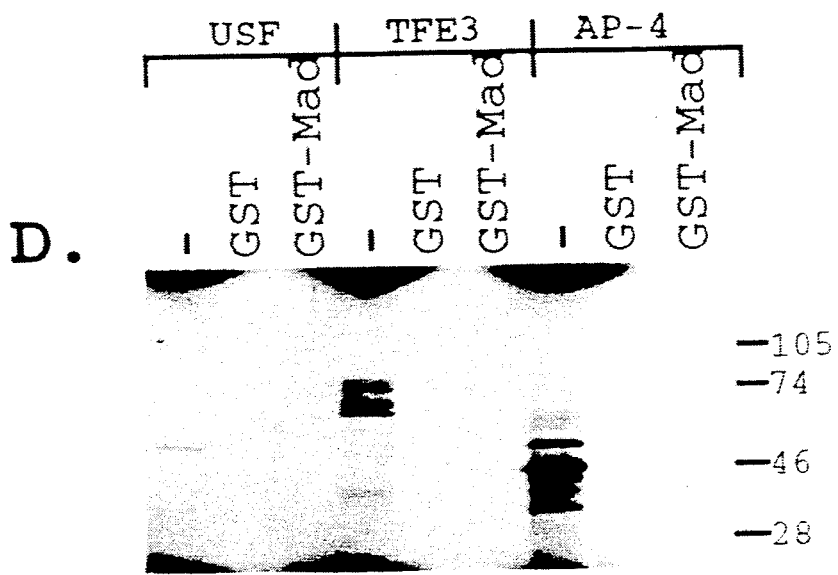
Figure 16E:
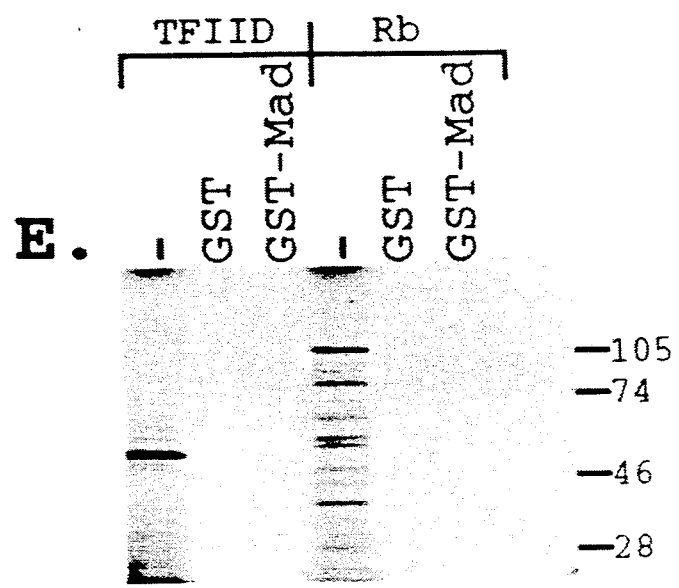
Figure 16F:
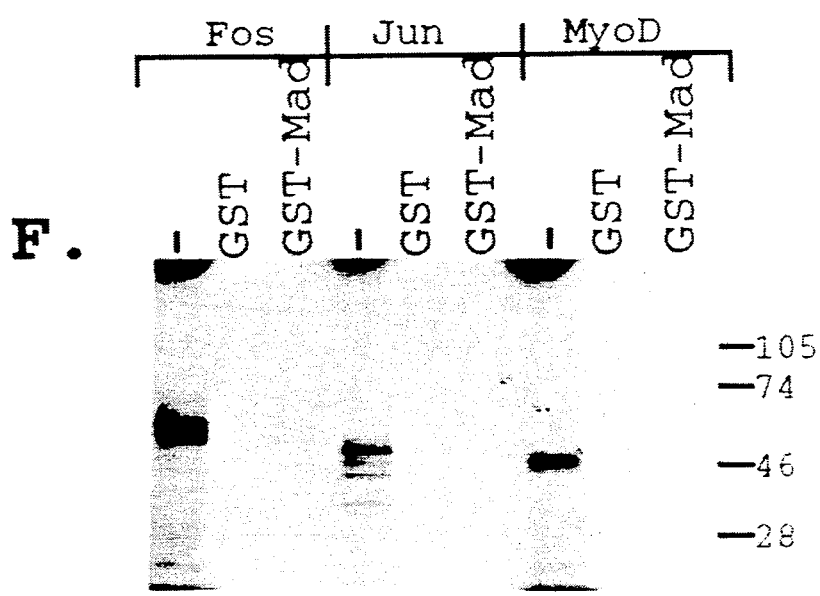

Therefore, these results suggest that Mad-1 has dimerization properties similar to those of Myc. Both Mad-1 and Myc homodimerize poorly but both readily form heterodimers with Max. It is likely that the physical characteristics of Mad-1 and Myc that prevent their homodimerization also prevent their heterodimerization. We have also examined the generality of Mad-1 binding by testing other members of the bHLH family and other proteins might be involved in Myc/Max function for interaction with GST-Mad. USF, TFE3 and AP-4 all have a structure similar to Myc, Max and Mad (i.e. b-HLH-zipper motif) and USF and TFE3 have similar DNA binding specificity to Myc and Max(i.e. bind the CACGTG site). MyoD has only a b-HLH motif whereas Fos and Jun use a leucine zipper for dimerization but use a region different from the basic region for DNA binding. Rb and TFIID have been reported to be in vitro binding partners for Myc. None of these proteins were able to interact with GST-Mad above background levels (FIGS. 16D,E,F).

FIG. 16. Specificity of Mad-1 protein binding. RNAs encoding the proteins given at the top of each panel were translated and labeled with $^{35}$S-methionine in vitro in the presence of either purified glutathione-s-transferase (GST) or glutathione-s-transferase fused in frame to baboon Mad-1 cDNA sequence encoding the c-terminal 186 amino acids of the Mad-I protein (GST-Mad). The proteins bound by GST or GST-Mad were analyzed on SDS polyacrylamide gels. The lanes marked - indicate translation products obtained in the absence of added purified protein. In FIG. 16B the arrows mark the position of either the ABR Max or Max9 and ALZ Max polypeptide The position of molecular weight markers (in kD) are given at the right of each panel.

EXAMPLE 8

The Mad-1:Max Heterodimer Binds DNA Specifically

The Max homodimer and the Myc:Max heterodimer bind the sequence CACGTG (CM- 1). We wondered if Mad-1 alone or with Max could recognize the same sequence. Using the electrophoretic moblility shift assay purified (EMSA) GST-mad or GST alone were tested in the presence or absence of Max for binding to the CM- I oligo (FIG. 17A).

In the absence of Max no binding was detected. This rules out nonspecific interaction of the GST portion of the fusion protein with DNA and suggests, as above, that mad homodimers did not form or were not stable. In the presence of Max a new slower migrating protein-DNA complex was seen in the presence of GST-Mad. Again, GST protein alone had no effect. The new complex was caused by binding of the GST-Mad:Max heterodimer because it was further retained in the gel matrix by antibodies specific for Max or GST. This supershift was reversible when the corresponding immunogen was added to the binding reaction and therefore specific for the given antibody-antigen complex. Mad:Max binding of the CM-1 oligo was specific because its activity in the EMSA was competed by cold CM-1 but not by equivalent amounts of a unrelated oligo of similar length (data not shown). We also wanted to investigate the binding of a potential Mad-1:Myc complex binding to the CM-1 oligo. Consistent with the lack of interaction between GST-C92Myc and GST-Mad (FIG. 16C) there was little or no DNA binding from a putative GST-Mad:GST-C92Myc heterodimer under conditions where the GST-C92Myc:Max and the GST-Mad:Max heterodimers form and bind DNA (FIG. 17C).

Figure 17A:
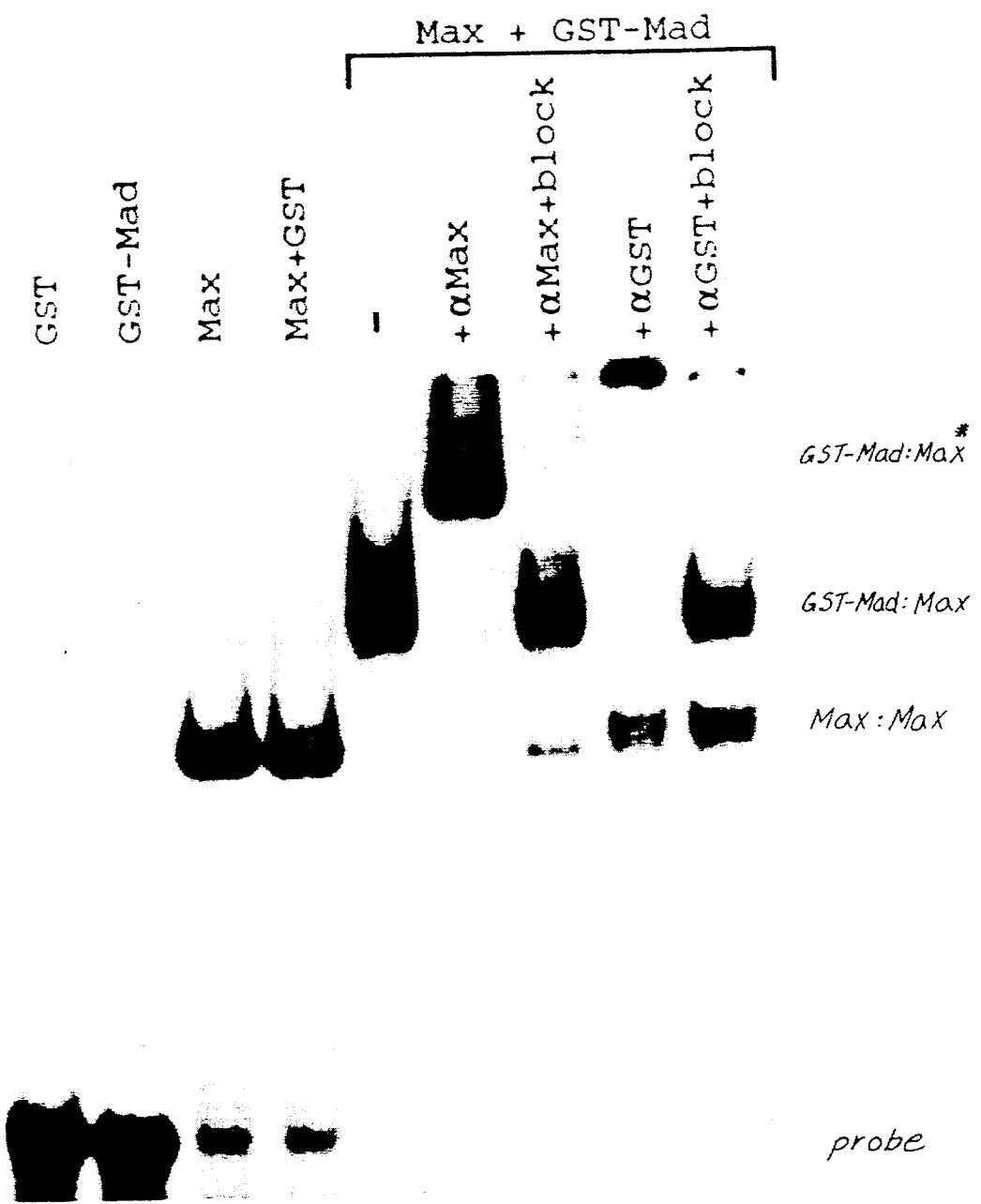
FIGS. 17A-C shows autoradiograms of gels from experiments designed to determine the DNA binding specificity of the Mad:Max heterodimer. The ability of Mad-1 to bind DNA and interact with Max and Myc was examined by the electrophoretic mobility shift assay. Purified fusion proteins, GST-Mad (FIG. 17A), and GST-C92Myc (FIG. 17B) were tested alone or in the presence of Max for binding to the CM-1 oligonucleotide. Non-fusion GST protein was used as a control. The protein(s) present in the binding reaction is indicated at the top of each gel lane in FIGS. 17A-B. As a control, the specificity of the electrophoretic mobility shift was assayed by including antibodies to either Max (αMax), GST (αGST) or Myc (αMyc) were added to the binding reaction. The activity of these antibodies was inhibited by adding the appropriate immunoglobulin to the binding reaction ("+block"). The lanes marked "-" had no additional protein present in the binding reaction. The position of each protein-DNA complex and the unbound probe is given. The "*" asterisk, (e.g., GST-Mad:Max*), indicates electrophoretic mobility of the control antibody complex. A diagram of the organizational structures of the GST polypeptides used in this experiment is shown below FIG. 17C.
Figure 17B:
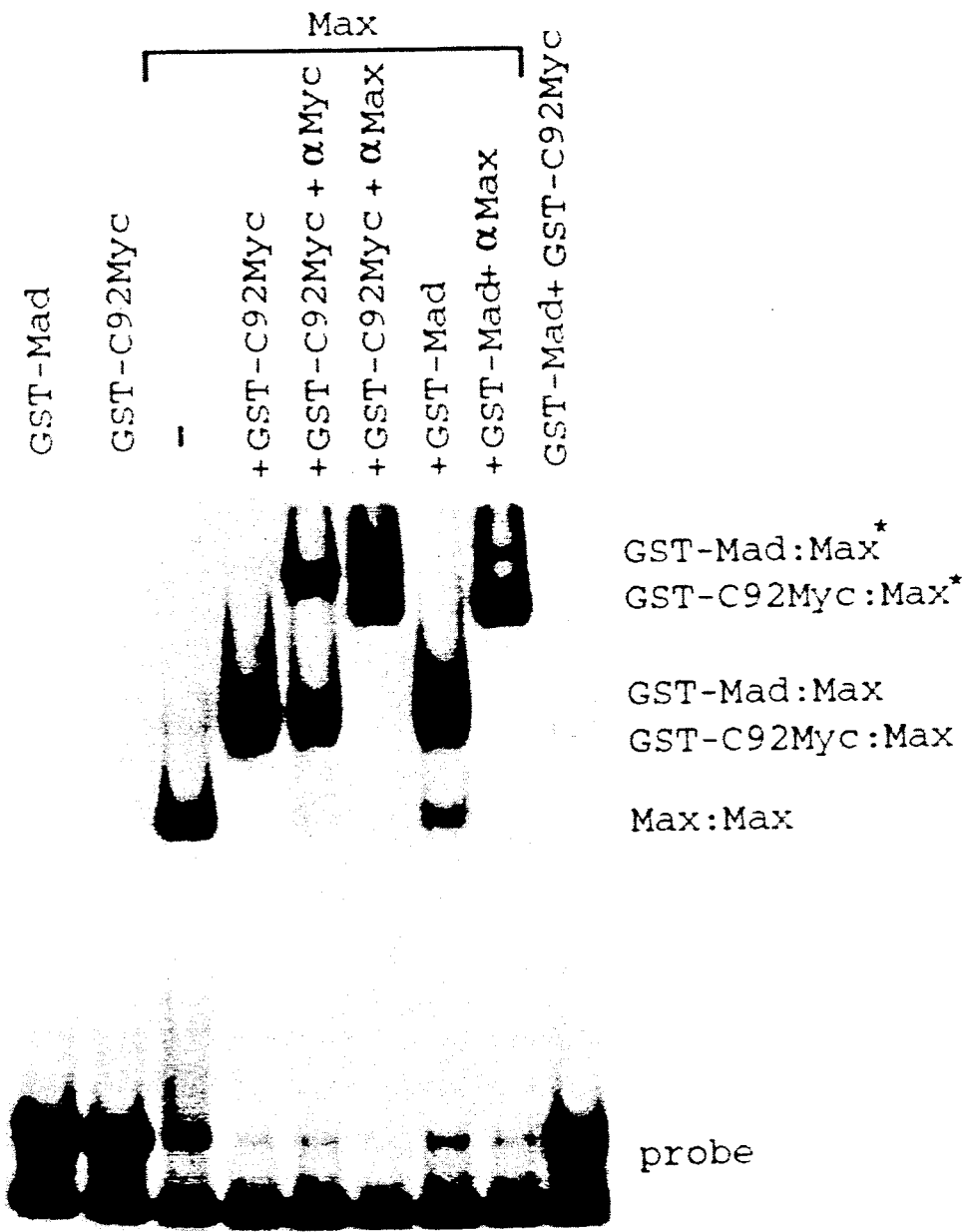
Figure 17C:
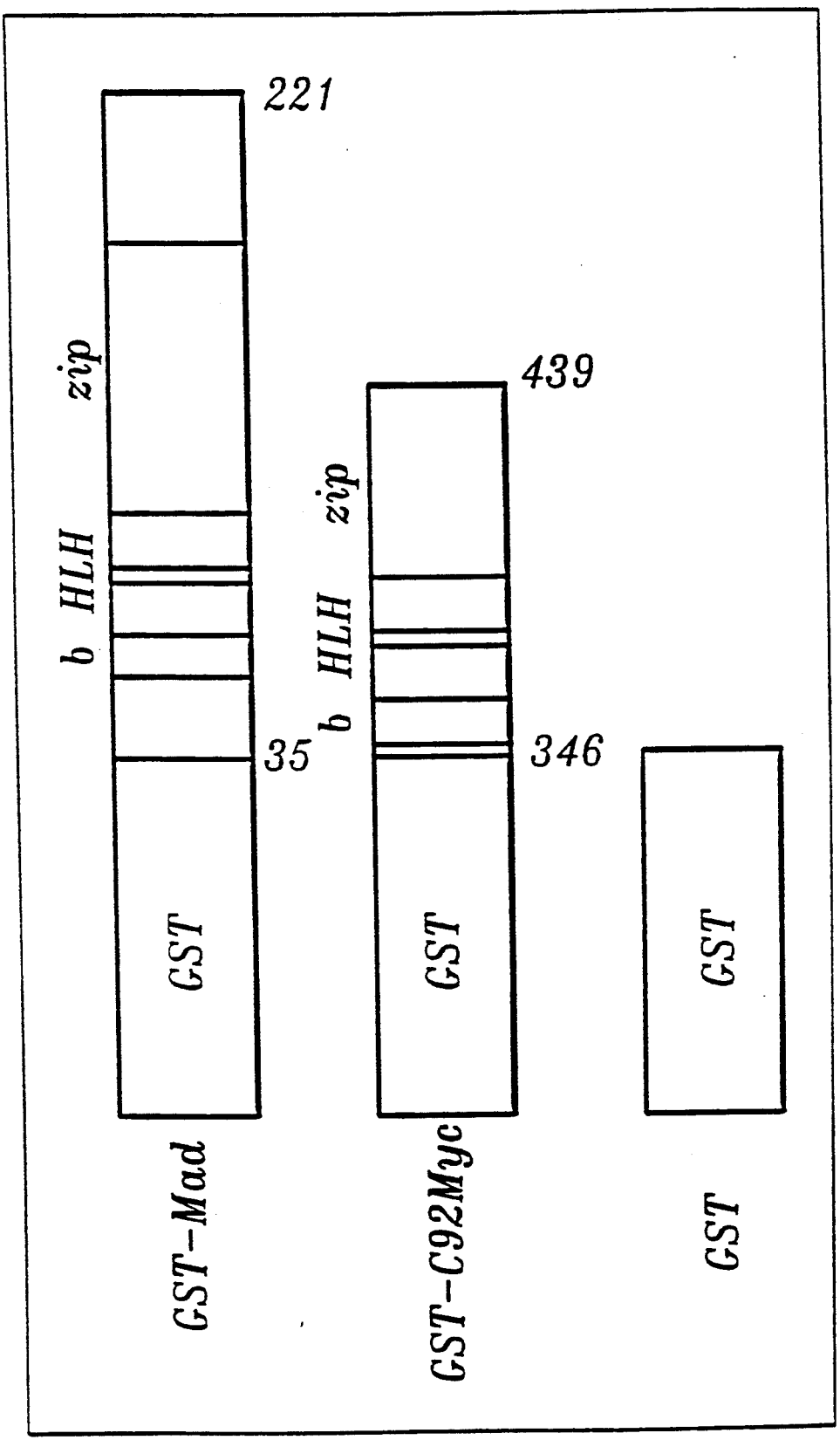

FIGS. 17A–C. Specific DNA binding by the Mad:-Max heterodimer. The ability of Mad-1 to bind DNA and interact with Max and Myc was examined by the EMSA. Purified proteins, GST, GST, GST-Mad, and GST-C29Myc were tested alone or in the presence of Max for binding to the CM-1 oligonucleotide. Which protein(s) was present in the binding reaction is indicated at the top of FIGS. 17A-B. In each experiment the specificity of the mobility shift was assayed by including antibodies to either Max((xMax), GST((xGST) or Myc((xMyc) were added to the binding reaction. The activity of these antibodies was inhibited by adding the appropriate in-imunogen to the binding reaction (+block). The lanes marked — had no additional protein present in the binding reaction. The position of each protein-DNA complex and the unbound probe is given. The asterisk indicates inclusion of antibody in the complex. A diagram of the GST proteins used in this experiment are shown.

EXAMPLE 9

Either GST-C92Myc:Max or GST-Mad:Max are Favored Over Max:Max Homodimers

The data presented in FIGS. 17A-C suggest that either GST-C92Myc:Max or GSTMad:Mad heterodimers bind the CM-1 site more tightly than the Max:Max homodimer. However, at the concentrations of protein used in that experiment the DNA probe is nearly exhausted and therefore the observed DNA binding was not in the linear range. To answer this question directly we assayed the amount of DNA binding derived from increasing amounts of Max in the presence or absence of either GST-C92Myc or GST-Mad. Under conditions where there was little or no Max homodimer DNA binding the addition of either GST-Myc or GST-Mad results in significant heterodimer DNA binding (FIG. 17A and 17B). As the amount of Max in the binding reaction was increased the heterodimeric binding increased until saturation was reached. This result suggested that either the GST-C92Myc:Max or the GSTMad:Max heterodimer was favored over the Max homodimeric complex. Based on current models it is most likely that the increased DNA binding of the heterodimeric species reflected increased levels of heterodimers rather than heterodimers having increased DNA binding activity per se.

EXAMPLE 10

DNA Binding of the Mad:Max Heterodimer Is Not Affected by Phosphorylation

The activity of many transcription factors is regulated by post-translational modification. DNA binding of Mad homodimers but not Myc:Max heterodimers is blocked by CKII phosphorylation. We wished to determine what effect CKII phosphorylation had on the DNA binding activity of the GST-Mad:Max heterodimer. Purified Max was treated with CKII in the presence or absence of ATP and assayed for DNA alone or with GST or GST-Mad. DNA binding activity tested by the EMSA (FIG. 18).

Figure 18A:
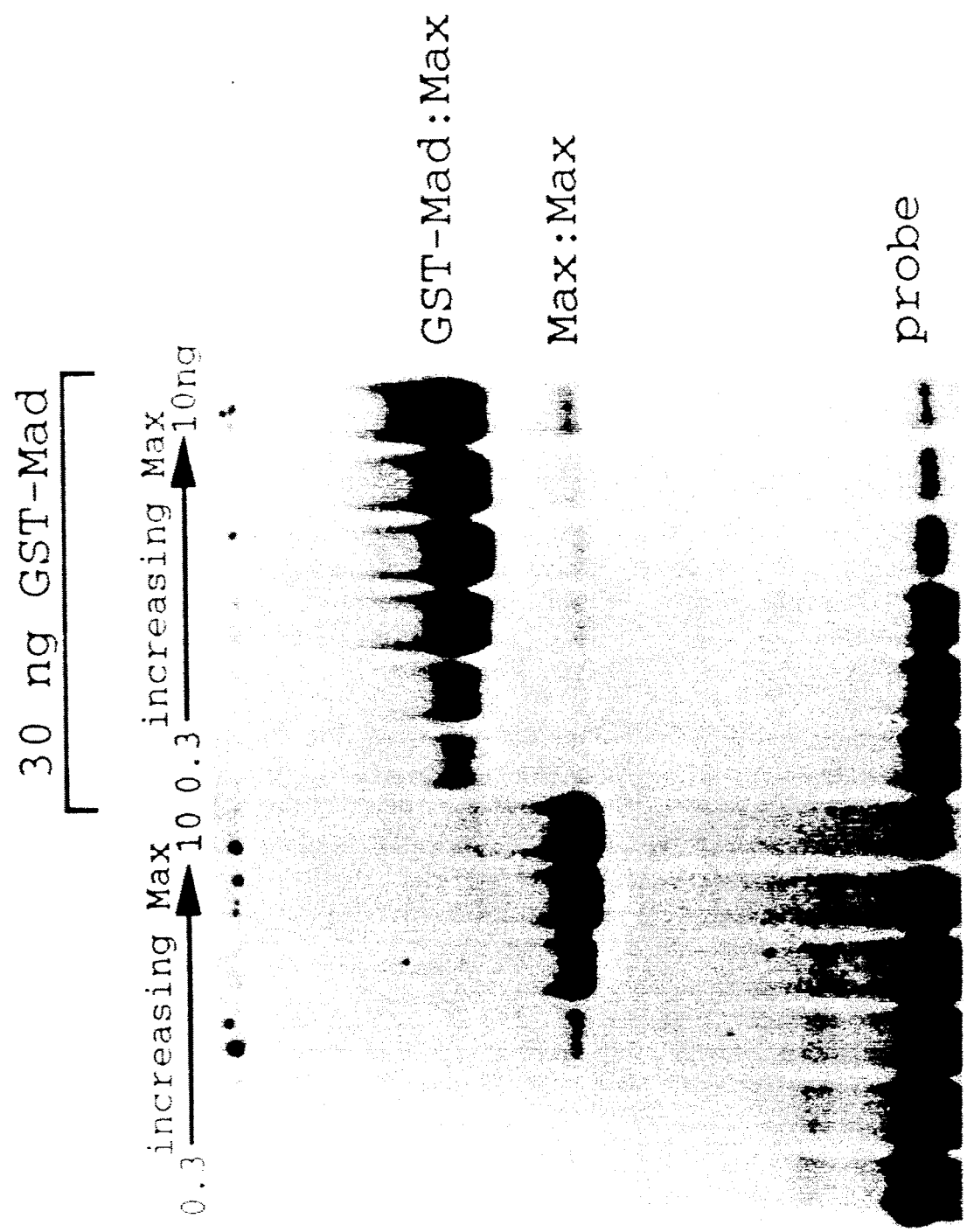
FIGS. 18A-B show an autoradiogram of a gel in which formation and DNA binding of Max:Max or Mad:Max complexes (FIG. 18A); and, the Myc:Max heterodimer (FIG. 18B) were evaluated as a function of increasing concentrations of Max (right directed arrows; "increasing Max" at the top of the gel lanes); at a constant concentration of either GST-Mad (i.e., 30 ng) or GST-C92Myc (i.e., 25 ng). The formation of Mad:-Max heterodimeric complexes was found to be favored over the Max:Max homodimer. (Increasing amounts of Max were assayed for DNA binding to the CM-1 oligonucleotide by the electrophoretic mobility shift assay either alone or in the presence of 30 ng GST-Mad or 25 ng GST-C92Myc). When assayed alone Max in the binding reactions was increased in roughly 2 fold increments from 0.3 ng to 10 ng. The same amounts of Max were tested with the indicated amount of fusion protein. In the lane marked "-" there was no protein in the binding reaction. The positions of the unbound probe and the protein:DNA complexes are indicated.
Figure 18B:
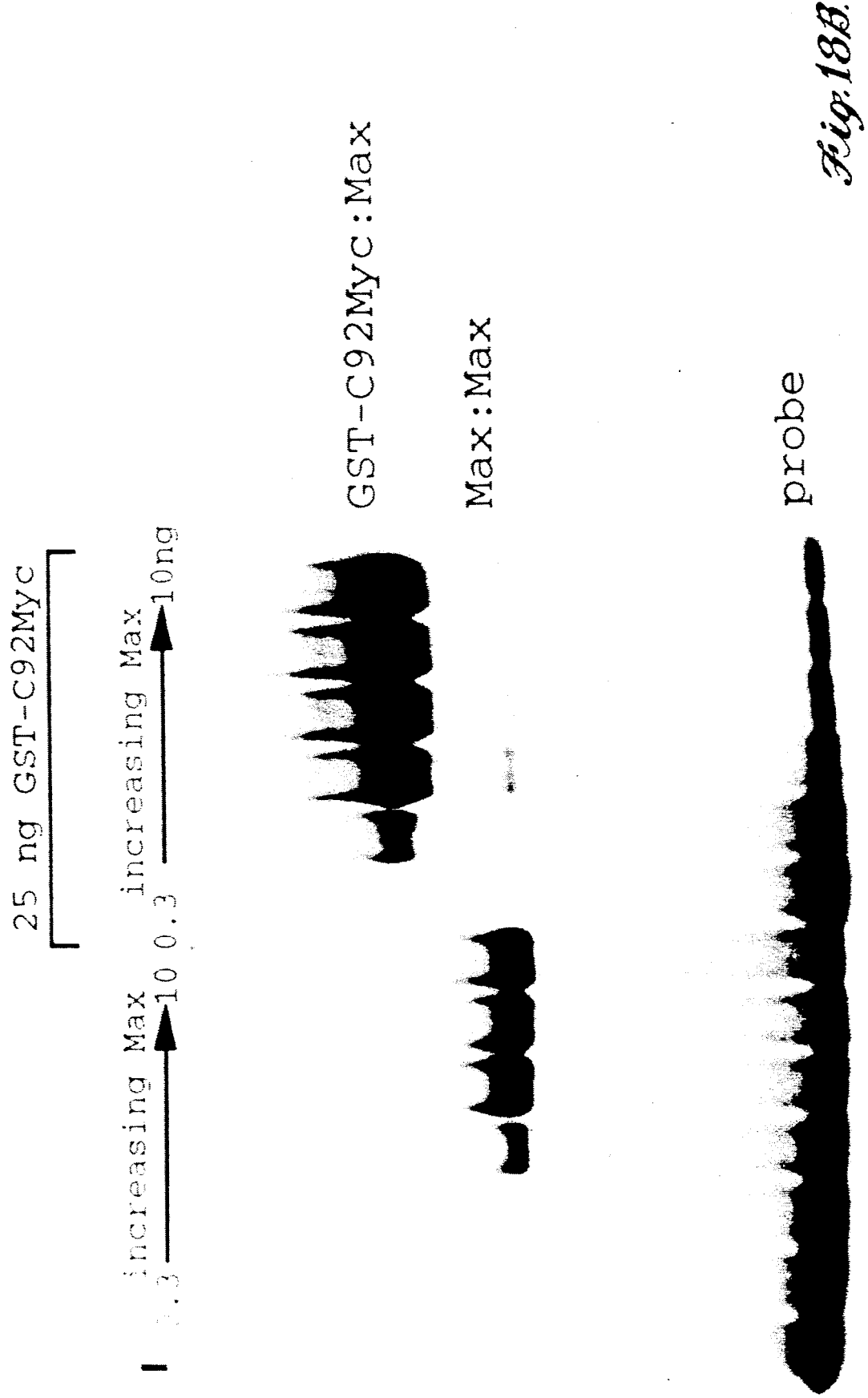

FIGS. 18A-B. Either the Mad:Max or the Myc:Max heterodimer is favored over the Max:Max homodimer. Increasing amounts of Max were assayed for DNA binding to the CM- I oligonucleotide by the EMSA either alone or in the presence of 30 ng GSTMad (FIG. 18A) or 25 ng GST-C92Myc (FIG. 18B). When assayed alone max in the binding reactions was increased in roughly 2 fold increments from 0.3 ng to 10 ng. The same amounts of Max were tested with the indicated amount of fusion protein. In the lane marked — there was no protein in the binding reaction. The positions of the unbound probe and the protein:DNA complexes are indicated.

There was no effect of GST or CKII in the absence of ATP on the Max homodimer mobility shift. As before, the addition of GST-Mad to Max resulted in the slower heterodimer mobility shift which was not effected by CKII in the absence of ATP. The addition of both CKII and ATP to the binding reaction resulted in a complete loss of Max homodimer binding but the binding of the Mad:Max heterodimer was unaffected. As expected the loss of Max homodimer binding was not restored by GST alone. Therefore, like the Myc:Max heterodimer, the GST-Mad:Max heterodimer can over ride the effect of CKII phosphorylation on Max.

EXAMPLE 11

Mad Competes for Max Cmplexed to Myc and Vice Versa

Because the GST-Mad fusion protein only encoded the C-terminal 186 amino acids of the Mad-1 protein and the fact that the GST-Mad:Max DNA complex comigrated with the GST-Myc:Max DNA complex in the EMSA we have made construct which encodes the full length Mad-1 coding region fused in frame to six histidines. This fusion protein, which we will refer to as Mad-1 throughout, was purified from *E. coli* by nickel chelate chromatography. The full length histidine tagged Mad-1 protein behaved identically to the GST-Mad fusion protein. It was able to form a heterodimer with Max capable of specific DNA binding (FIG. 19 and data not shown).

The Mad:Max heterodimer and the Max homodimer DNA complexes migrated as a closely spaced doublet. The Mad:Max complex is the faster migrating of the two protein:DNA complexes. As expected, Mad-I could neither bind CM-I in the absence of Max nor in the presence of GST-C92Myc.

Both Myc and Mad-1 can bind Max. It is possible that one of the heterodimers is more stable than the other and would be expected to predominate even in the presence of the other Max binding partner. In order to test this we assayed the stability of one heterodimer by allowing it to form in the presence of the other Max binding partner. Both GSTC92Myc and Mad-1 were greater than 50% pure as judged from Coomassie stained gels (data not shown); however, it was difficult to determine the amount of active protein in each preparation. We therefore first determined the minimal amount of each fusion protein that would complex with 2 ng of purified Max (data not shown). In order to determine the stability of the GST-C92Myc:Max heterodimer complex (in a ratio of 6 ng:2 ng) it was allowed to form in the presence of increasing amounts of Mad-1. The converse experiment was done to test the stability of the Mad:Max (7.5 ng:2 ng) heterodimer by allowing the complexes to form the presence of increasing amounts of GST-C92Myc. The resulting protein-DNA complexes were resolved on nondenaturing gels (FIG. 19).

Figure 19:
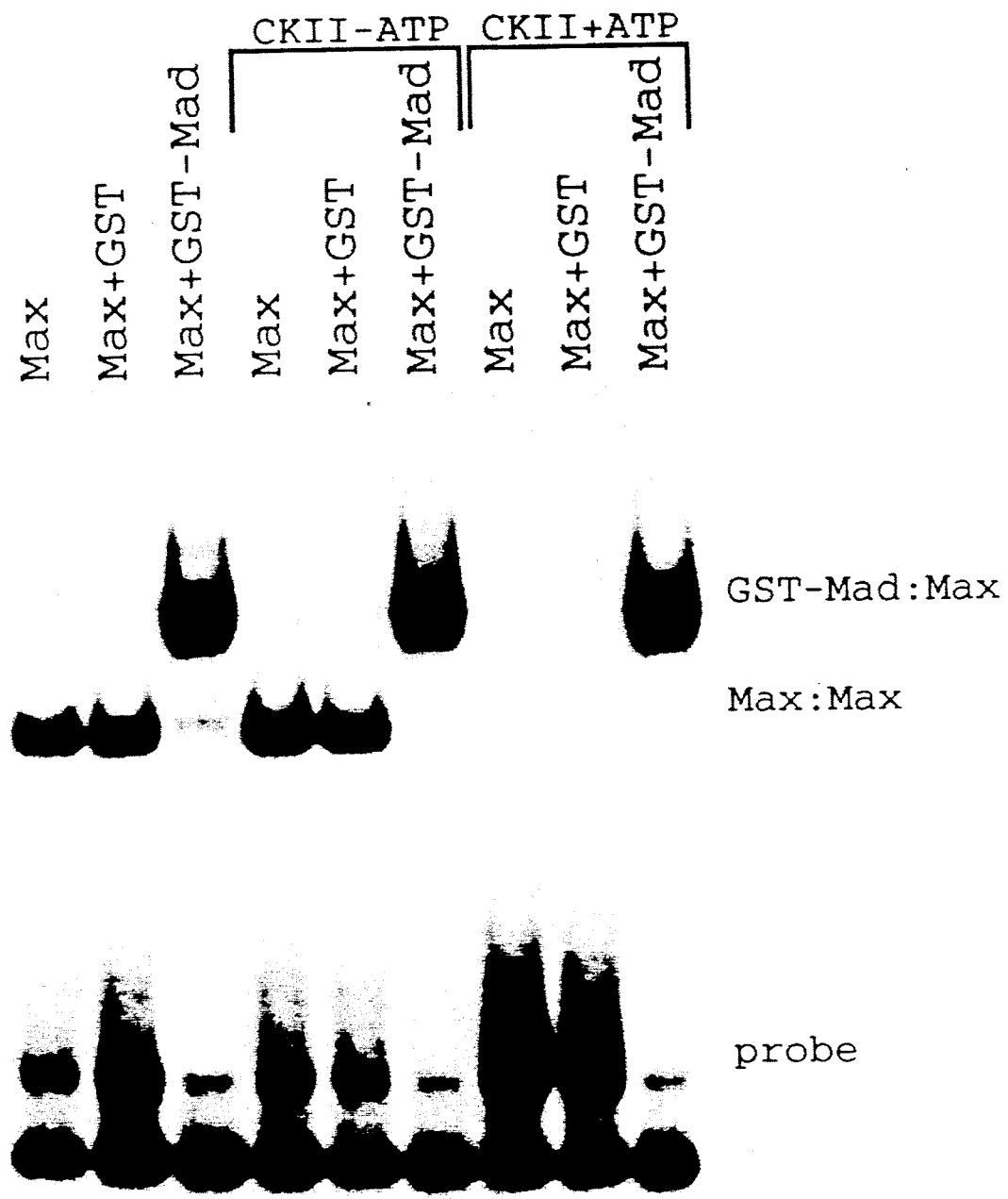
FIG. 19 shows an autoradiogram of a gel in which the binding of phosphorylated Mad was tested for formation of complexes with Max and binding to DNA. The results show that CKII phosphorylation does not affect the DNA binding of the Mad:Max heterodimer. (Max or Max treated with CKII was tested for DNA binding to the CM-1 oligonucleotide by the electrophoretic mobility shift assay presence of GST or GST-Mad. The proteins in the binding reactions are given at the top of the FIGURE. In the lanes marked "CKII-ATP" or "CKII+ATP Max" was treated with CKII either in the absence or the presence of ATP, respectively, prior to inclusion in the DNA binding reaction. The positions of the free probe and the protein DNA complexes are indicated.)

FIG. 19. CKII phosphorylation does not affect the DNA binding of the Mad:Max heterodimer. Max or Max treated with CKII was tested for DNA binding to the CM-1 oligonucleotide by the EMSA presence of GST or GST-Mad. The proteins in the binding reactions are given at the top of the figure. In the lanes marked CKII-ATP or CKII+ATP Max was treated with CKII either in the absence or the presence of ATP, respectively, prior to inclusion in the DNA binding reaction. The positions of the free probe and the protein DNA complexes are indicated.

Figure 20A:
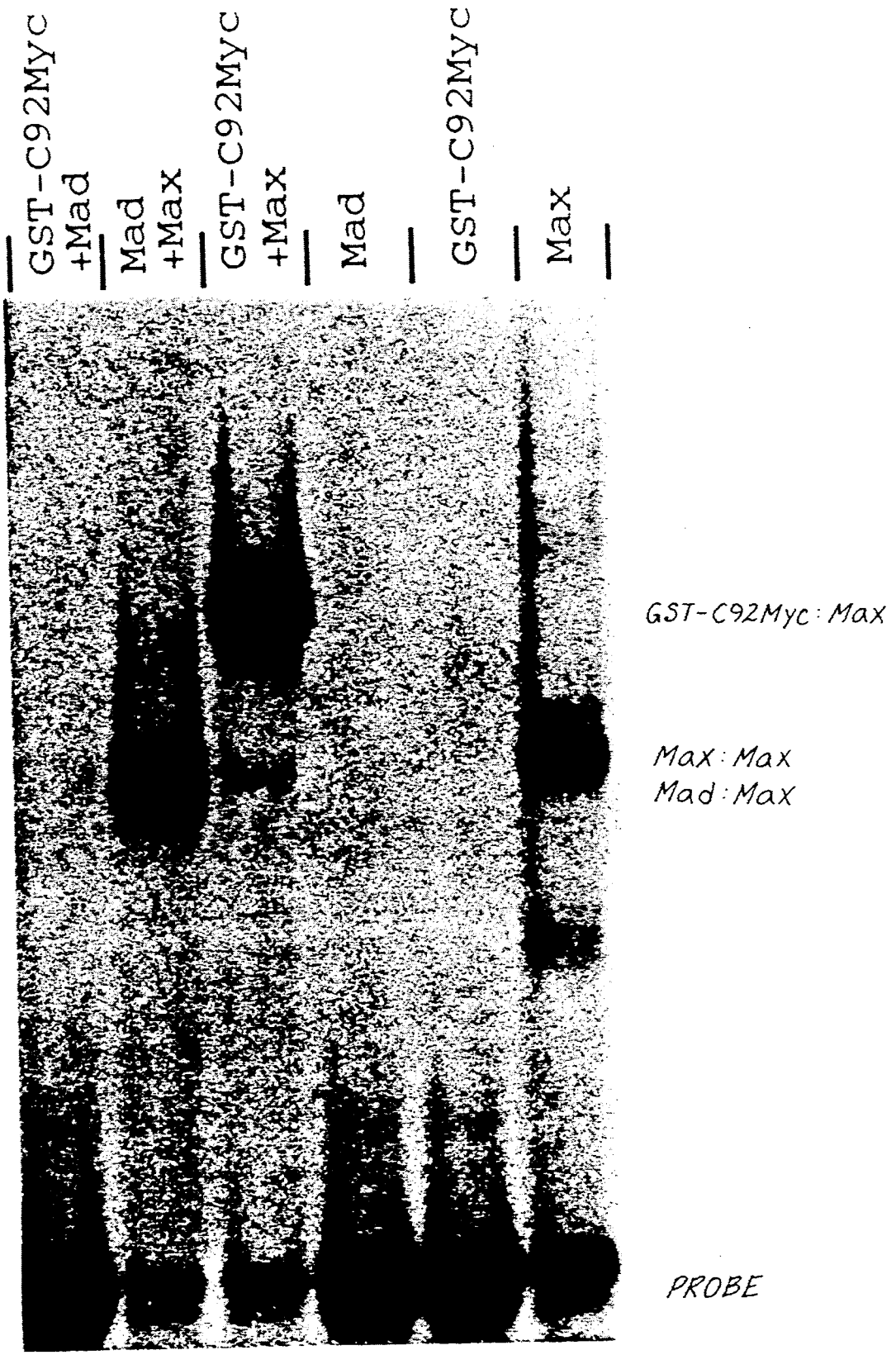
FIGS. 20A-C show autoradiograms of gels in which the binding affinity of Myc:Max and Mad:Max to DNA was compared in electrophoretic mobility shift assays. The proteins present in the binding reactions is given at the top of each gel lane. ("-") indicates the absence of protein in the binding reaction. The positions of the protein:DNA complex and the unbound probe is given at the right of each panel.
Figure 20B:
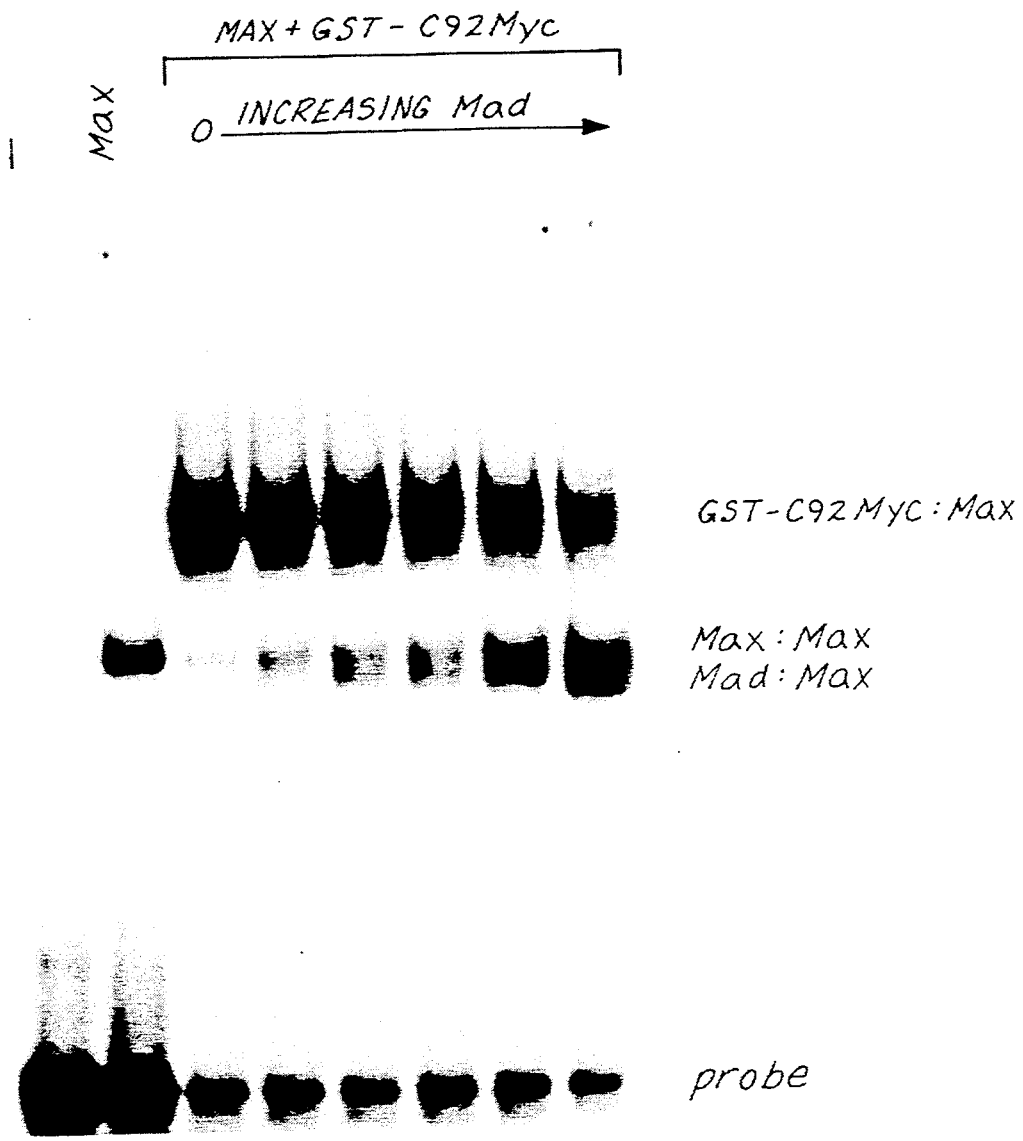
Figure 20C:
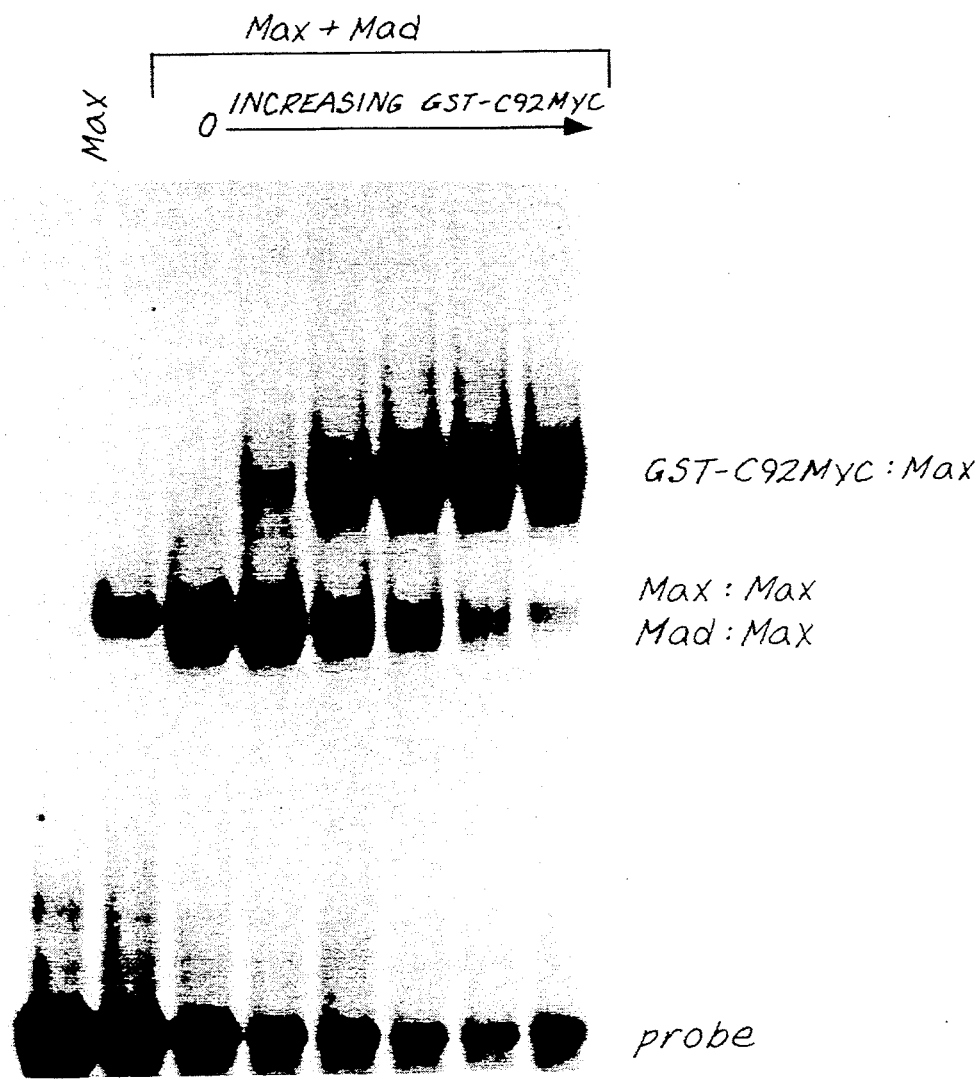

FIGS. 20A–C. The Myc:Max and the Mad:Max DNA binding complexes have similar affinities for DNA. The DNA binding characteristics of the purified histidine tagged Mad was assayed by the EMSA (FIG. 20A). In all three panels the proteins present in the binding reactions is given at the top of FIG. 20. ("—") indicates the absence of protein in the binding reacfion. The positions of the protein:DNA complex and the unbound probe is given at the right of each panel. In the experiment shown in FIG. 20B and FIG. 20C a constant amount of either GST-C92Myc:Max (6ng:2ng) (FIG. 20B) or Mad:Max (7.5ng:2ng) (FIG. 20C) was challenged with increasing amount of Mad or GST-C92Myc, respectively. The challenging protein was increased in 2 fold increments for both Mad and GST-C92Myc. The titration started at 1.8 ng for Mad and at 1.6 ng for GST-C92Myc and went to 30 ng and 50 respectively.

The amount of Mad:Max heterodimer complex observed was reduced in the presence of increasing amounts of GST-C92Myc. A concomitant increase in the amount of GSTC92Myc:Max complex was also observed. The analogous result was obtained when GST-Myc:Max complexes were tonned in the presence of increasing amounts of Mad-1, i.e. there was a decrease in the amount of GST-C92Myc:Max complex and an increase in the amount of Mad:Max complex. In both experiments there was competition even at the lowest amount of added competing protein (1.6ng of Mad-1 and 1.8 ng for GST-C92 Myc). Similar results were obtained if one pair heterodimers were allowed to form prior to the addition of the other fusion protein. Although, a higher level of the competing protein was required to disassociate the preformed heterodimeric complex. Given that the half life of the Myc protein in cells is very rapid it is not clear if this result is meaningful. In addition, the DNA binding site did not stabilize or destabilize either of the heterodimeric complexes (data not shown). Because the fusion proteins have roughly the same molecular weight the computation was carried out under conditions with each of the proteins present in near equal molar concentrations. Therefore, the results suggest that Myc and Mad-1 bind Max with similar affinities and that the levels of each protein were important in determining which heterodimer predominated.

DISCUSSION

We present in EXAMPLES 6–11, above, the identification and characterization of a new Max dimerization partner:Mad. Mad is a new member of the bHLH-Zip family of transcription factors and its interaction with Max appears to be fairly specific. The physical characteristics of Mad and the Mad:Max heterocomplex are very similar to those of Myc and the Myc:Max complex. A model for these interactions and their outcome on DNA binding are given in FIG. 21.

Figure 21:
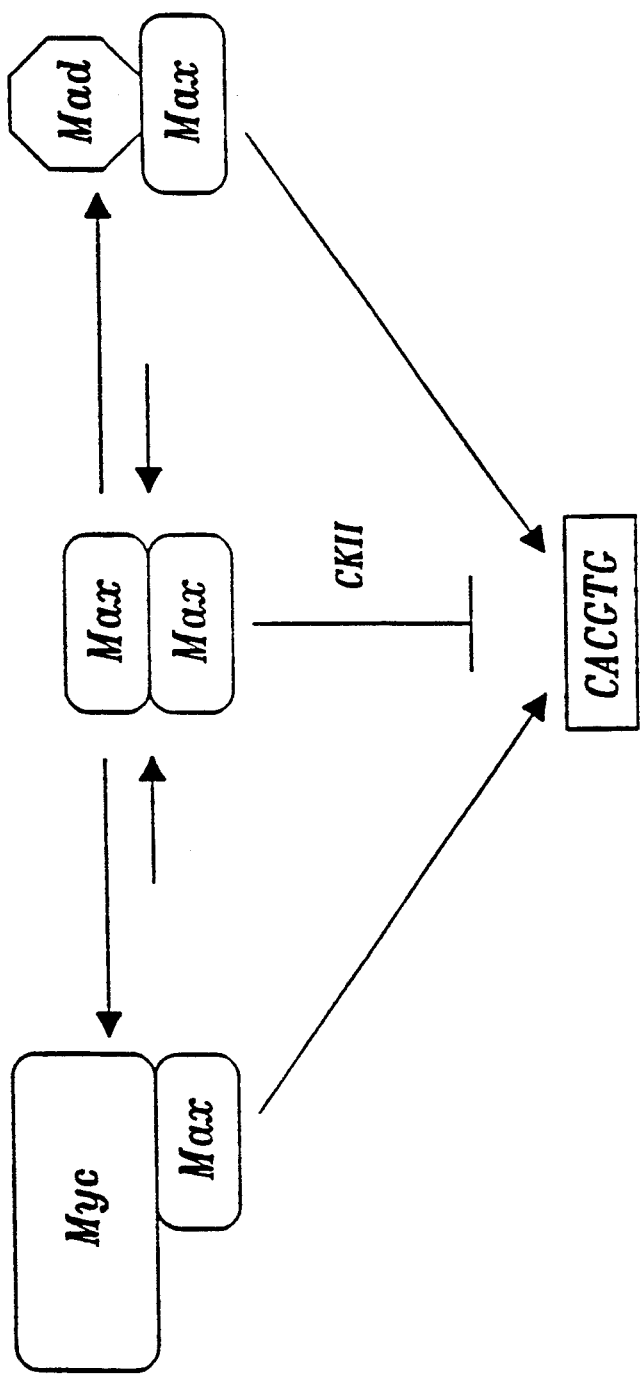
FIG. 21 shows a schematic diagram depicting the binding interactions of the Myc, Max and Mad-1 polypeptides, and the DNA binding sites in the respective complexes to the specific CACGTG nucleotide sequence motif in DNA.

FIG. 21. A scheme for the interactions between Myc, Max and Mad-1. The in vitro interactions between Myc Max, and Mad- 1 their specific DNA binding site are shown.

Myc and Mad bind DNA specifically only at high protein concentrations suggesting that both proteins homodimerize poorly. Both proteins can heterodimerize with Max to form a specific DNA binding complex. While the model shows only binding to a CACGTG site both heterodimers show identical binding on variants of this site (K. Blackwell and D. Ayer, unpublished observations). Therefore, while there has been no Myc responsive cellular target yet identified, it is likely that the in vivo binding sites for the Myc:Max heterodimer will be occupied by Mad:Max heterocomplex as well. Either the Myc:Max or Mad:Max heterocomplex is favored over the Max homodimer. Finally, in contrast to the DNA binding of Max homodimers, the DNA binding activity of either Max containing heterocomplex is unaffected by CKII phosphorylation. It will be interesting to determine if Mad and Myc are similar in other characteristics. For example, is Mad a unstable protein and regulated upon entry to and exit from the cell cycle.

In transient transfection assays, Myc activated transcription of a heterologous reporter gene containing the CACGTG binding motif in its promoter while Max repressed transcription from the reporter construct (Kretzner et. al, submitted). Because Myc forms heterodimers poorly it was assumed that interaction with Max was responsible for the observed Myc transcriptional activation. Max repression has been assumed to be the result of Max homodimers repressing transcription from the reporter construct (FIRST AND SECOND SERIES OF EXAMPLES, above). It must now also be considered that transcriptional repression observed may in certain cases have been due to Max interacting with endogenous Mad. If Myc:Max is responsible for transcriptional activation and Mad:Max potentially acts as a transcriptional repressor, what function do Max homodimers play in controlling gene expression? Because Max homodimers are unfavored, in the presence of both Myc and Mad, the cellular levels of Max homodimers will be low. In addition, cells have evolved a mechanism to keep Max homodimers off DNA, namely CKII phosphorylation. Max isolated from cells is phosphorylated 0 and treatment of purified Max from human or insect cells with aluine phosphatase greatly increases DNA binding (D. Ayer and E. Blackwood, unpublished observation). These data suggest that the majority of Max is either off the DNA as homodimers or bound as either a Myc:Max or Mad:Max heterocomplex.

By binding to Max, Mad potentially antagonizes Myc function. In vitro binding experiments suggest that the relative levels of either Myc or Mad will determine which of the heterocomplexes will be most prevalent. It is therefore critical to determine levels of Myc and Max protein in various cells and times during the cell cycle. If the Mad:Max complex is the antithesis of the Myc:-Max complex one might expect Mad expression to be highest where Myc activity is low. For example, Mad expression might be elevated in resting $G_0$ cells or cells that are terminally differentiated.

Max allows two proteins, Myc and Mad, to bind DNA raising the possibility that other proteins might also require Max to mediate their DNA binding and activity. We are cur-rently screening expression libraries for other Max binding proteins. Interestingly, using a genetic screen in yeast, another lab has cloned a CDNA encoding a protein, distinct from Mad, but having properties very similar to those of Mad (T. Zervos, personal communication).

EXPERIMENTAL PROCEDURES

Expression and purification of Max. The cDNA encoding Max was cloned into the baculovirus transfer vector pJVNhe and recombinant virus was plaque purified as described. For Max expression and purification $2 \times 10^8$ Sf9 cells were infected at an MOI of 5. 48 hours PI cells were washed twice with PBS and a cytoplasmic extract was prepared by lysing the cells in HMO.1* (50 mM Hepes pH 7.5, 100 mM KCl, 10 mM MgCl$_2$, 1 mM EDTA, 10% glycerol, 1 mM DTT, 0.5% NP-40, 10 mg/ml PMSF and 0.1% aprotinin) and pelleting the cellular debris at 10,000xg for 10 minutes. Max represented about 1% of the total protein present in this cytoplasmic extract. The cytoplasmic extract was applied to a 25 ml BioRex 70 (Biorad) column equilibrated in HMO.1 (identical to HMO.1* but with no NP-40). Max was eluted with a linear gradient of KCl in HMO.1. The majority of the Max eluted in a broad peak between 0.3 and 0.6M KCl. The Max containing fractions were pooled and diluted with HMO (HMO.1 with no KCl) to a conductivity corresponding to 100 mM KCl and applied to a mono-Q HR 5/5 column (Pharmacia) equilibrated in HMO.1. Max eluted between 200 and 300 mM KCl. The peak fractions were pooled and stored at $-80°$ C. This Max preparation was at least 95% pure as judged by silver staining of SDS polyacrylamide gels.

Screening for Max Binding partners: 3 μg purified Max protein was labeled to high specific activity ($10^7$ cpm/μg) by CKII (a kind gift of D. Litchfield and E. Krebs) and [γ-$^{32}$P] ATP (3000 Ci/mMol, Dupont NEN) in HMO.1 for 30 minutes at 30° C. The unincorporated ATP was removed on a Sephadex G-50 column equilibrated with HMO.1. Approximately $10^6$ phage form the 594S gt11 expression library were plated in LE392 on 150 mm$\times$15 mm dishes and incubated at 37° C. After the plaques had reached 2-3 mm in size filters (Amersham Hybond C Extra) were overlaid and the proteins were allowed to transfer overnight at 37° C. The filters were blocked (4 washes of 30 minutes each at 4° C.) in 5% nonfat dry milk, 20 mM Hepes pH 7.5, 50 mM KCl, 10 mM MgCl$_2$, 10 mM β glycerol phosphate, 1 mM DTT and 0.1% NP-40. Filters were probed for 4-5 hours with $3\times10^7$ cpm Max probe (roughly 5 nM Max) in 1% nonfat dry milk, 20 mM Hepes pH 7.5, 50 mM KCl, 10 mM MgCl$_2$, 10 mM β glycerol phosphate, 10 mM DTT, 0.1% NP-40 and 10% glycerol. The filters were washed in PBS/0.2% Triton X-100 for 10 minutes to remove the bulk of the unbound counts. Three additional washes (15-30 minutes each) were done with PBS/0.2% Triton X-100+100 mM KCl. The filters were wrapped in saran and exposed for autoradiography. The phage DNA from the positive clones was purified (Qiagen Lambda mini kit) and the cDNA insert cloned into the vector pVZ-1.

Screening for the human Mad homolog: A fragment from the 5' end of the baboon Mad cDNA was isolated and used to probe a human gt10 cDNA library from embryonic lung fibroblasts (WI-26). Two positive clones were identified. The phage DNA was purified and the cDNA insert subcloned into pVZ-1. All DNA sequencing was done using the Sequenase kit from United States Biochemical.

Production and purification fusion proteins: An oligo (TCAGAATTCTATACAAAAGG) was synthesized that overlapped the 5'end of the baboon Mad cDNA and use with T3 promoter primer to PCR amplify the Mad cDNA. The amplified DNA fragment was subcloned into pGEX-2T. Cells containing the pGEX-2TMad plasmid were grown to OD600 of 0.7 and induced with 0.2 mM IPTG and the fusion proteins purified as described with the following modification. The fusion protein was eluted HMO.1 containing 5 mM glutatione (Sigma). The GST-C92 Myc fusion protein produced in a similar fashion. To make a cDNA encoding the Mad protein fused to 6 histidines full length human Mad-1 coding region was amplified using the T7 promoter primer and a oligo (TCAGTCCATGG-CTAGTGGTGGTGGTGGTGGTGGAGAC-CAAGACACGC) that overlapped the 3'end of the Mad coding region but also encoded six in frame histidines and a stop codon. The amplified product was cloned into pET11D and introduced in the E. coli strain DE3. The Mad-Ifusion protein was purified using nickel chelate chromatography under denaturing conditions according to the vendor's instructions (Qiagen) and dialyzed against three changes of HMO.1. All proteins were stored at $-80°$ C.

Subcloning of the human Mad cDNA: The 3' untranslated region of the Mad cDNA was removed using an internal Eco R1 site and the Eco R1 site in the polylinker of pVZ-1. Because the Mad cDNA was translated poorly in vitro it was necessary to remove the 5' untranslated sequences. Ilis was done by PCR using an oligo (GTCAGAATTCAC-CATGGCGGCGGCGGTT) to the 5'end of the Mad-1 coding region and the T3 promoter primer. The amplified product was cloned back into pVZ-1 and into the vector pcite-1 (Novogen).

In vitro characterization of Mad binding partners: Various cDNAs were translated in the presence of 50 ng GST-Mad or 50 ng GST. Following translation, 50 μl of PBS containing an additional 100 mM KCl and 0.5% NP-40 was added along with glutathione-sepharose beads (Pharmacia). The translation products were allowed to bind for 10 minutes and the beads were washed 5 times with PBS containing 100 mM KCl and 0.5% NP-40. The bound proteins were eluted with sample buffer and analyzed on SDS polyacrylamide gels.

Electrophoretic mobility shift assays: The binding reactions contained 0.2-0.5 ng of the CM-1 binding site (CCCCCACCACGTGGTGCCTGA) 25 mM Hepes pH 7.5, 50 mM KCl, 5 mM MgCl$_2$, 0.5 mM EDTA, 5% glycerol, 10 mM DTT, 0.1% NP-40, 0.5 mg/ml BSA, 0.02% Bromophenol blue/xylene cyanol and the indicated amount of protein. In the cases where the amount of protein in the binding reaction is not given typically 5-10 ng Max or 20-30 ng of the various fusion proteins were used. The resulting protein DNA complexes were resolved on 5% polyacrylamide gels run with 25 mM Hepes pH 7.5 in the gel and the running buffer. The gels were run in at 4° C. The non-specific site used in the competitions corresponded to the MREA site in the Mim-1 promoter (TCGAGTAAGACACCCGT-TACTTTACG). CKII phosphoryation of Max was performed using 3 ng purified CKII in the gel shift buffer given above plus 100 mM ATP.

CITATIONS

1. L. J. Z. Penn, E. M. Laufer, H. Land, Semin. Cancer Biol. 1, 69 (1990); B. Luscher and R. N. Eisenman, Genes Dev. 4, 2025 (1990).
2. H. Abrams, L. Rohrschneider, R. N. Eisenman, Cell 29, 427 (1982); P. Donner, I. Greiser-Wilke, K. Moelling, *Nature* 296, 262 (1982); S. R. Hann and R. N. Eisenman, *Mol. Cell. Biol.* 4, 2486 (1984); R. A. Watt, A. R. Shatzman, M. Rosenberg, ibid. 5, 448 (1985); G. Ramsay, L. Stanton, M. Schwab, J. M. Bishop, ibid. 6, 4450 (1986); J. De Greve et al., ibid. 8, 4381 (1988); C. V. Dang, H. V. Dam, M. Buckmire, W. M. F. Lee, ibid. 9, 2477 (1989); K. Saksela, T. P. Makela, G. Evan, K. Alitalo, *EMBO J.* 8, 149 (1989).

3. J. Stone et al., *Mol. Cell. Biol.* 7, 1697 (1987); P. J. Enrietto, *Virology* 168, 256 (1989); H. Nakajima, M. Ikeda, N. Tsuchida, S. Nishimura, Y. Taya, *Oncogene* 4, 999 (1989); D. H. Crouch, C. Lang, D. A. F. Gillespie, ibid. 5, 683 (1990).

4. S. O. Freytag, C. V. Dang, W. M. F. Lee, *Cell Growth Differ.* 1, 339 (1990).

5. M. J. Smith, D. C. Charron-Prochownik, E. V. Prochownik, *Mol. Cell. Biol.* 10, 5333 (1990); L. J. Z. Penn et al., ibid., p. 4961.

6. N. Jones, Cell 61, 9 (1990); E. N. Olson, *Genes Dev.* 4, 1454 (1990).

7. C. Murre, P. S. McCaw, D. Baltimore, *Cell* 56, 777 (1989).

8. S. J. Tapscott et al., *Science* 242, 405 (1988).

9. A. Voronova and D. Baltimore, *Proc. Natl. Acad. Sci. U.S.A.* 87, 4722 (1990).

10. C. Murre et al., *Cell* 58, 537 (1989).

11. R. L. Davis, P.-F. Cheng, A. B. Lassar, H. Weintraub, ibid. 60, 733 (1990).

12. W. H. Landschulz, P. F. Johnson, S. L. McKnight, *Science* 240, 1759 (1988).

13. E. K. O'Shea, R. H. Rutkowski, P. S. Kim, ibid. 243, 538 (1989).

14. C. R. Vinson, P. B. Sigler, S. L. McKnight, ibid. 246, 911 (1989).

15. T. Kouzarides and E. Ziff, *Nature* 336, 646 (1988).

16. E. M. Blackwood, B. Luscher, R. N. Eisenman, unpublished data; see also the Second Series of Examples herein.

17. T. K. Blackwell, L. Kretzner, E. M. Blackwood, R. N. Eisenman, H. Weintraub, *Science* 250, 1149 (1990).

18. Luscher, B. and R. N. Eisenman, "New Light on Myc and Myb. Part I. Myc." *Genes Dev.* 4(12a):20-25-2035, 1990.

19. Penn, L. J. Z., E. M. Laufer and H. Land. "C-MYC: evidence for multiple regulatory functions." *Semin. Cancer Biol.* 1:69-87, 1990.

20. Hann, S. R., C. B. Thompson and R. N. Eisenman. "c-myc onogene protein synthesis is independent of the cell cycle in human and avian cells." *Nature.* 314(6009):366-369, 1985.

21. Thompson, C. B., P. B. Challoner, P. E. Neiman and M. Groudine. "c-myc mRNA levels are independent of the cell cycle." *Nature.* 314-366, 1985.

22. Coppola, J. A. and M. D. Cole. "Constitutive c-myc oncogene expression blocks mouse erythroleukemia cell differentiation but not commitment." *Nature.* 320:760-763, 1986.

23. Freytag, S. O., C. V. Dang and W. M. F. Lee. "Definition of the activities and properties of c-myc required to inhibit cell differentiation." Cell Growth & Differentiation. 1:339-343, 1990.

24. Holt, J. T., R. L. Redner and A. W. Nienhuis. "An oligomer complementary to c-myc mRNA inhibits proliferation of HL60 promyelocytic cells and induces differentiation." *Mol. Cell. Biol.* 8(2):963-967, 1988.

25. Kelly, K., B. H. Cochran, C. D. Stiles and P. Leder. "Cell-specific regulation of the c-myc gene by lymphocyte mitogens and platelet-derived growth factor." *Cell.* 35:603-610, 1983.

26. Heikkila, R., G. Schwab, E. Wickstrom, S. L. Loke, D. H. Pluznik, R. Watt and L. M. Neckers. "A c-myc antisense oligodeoxynucleotide inhibits entry into S phase but not progress from G0 to G1." *Nature.* 328:445-449, 1987.

27. Eilers, M., S. Schirm and J. M. Bishop. "The MYC protein activates transcription of the a-prothymosin gene." *EMBO J.* 10(1):133-141, 1991.

28. Cory, S. "Activation of cellular oncogenes in hematopoietic cells by chromosome translocation." *Advances in Cancer Research.* 1986.

29. Eisenman, R. N. "Nuclear Oncogenes in Oncogenes and the Molecular Origins of Cancer.":175-221, 1989.

30. Magrath, I. "The pathogenesis of Burkitt's lumphoma." *Adv. Cancer Res.* 55:134-251, 1990.

31. Spencer, C. A. and M. Groudine. "Control of c-myc regulation in normal and neoplastic cells." *Adv. Cancer Res.* 56:1-48, 1991.

32. Marshall, C. J. "Tumor suppressor genes." *Cell.* 64(2):313-326, 1991.

33. Pietenpol, J. A., J. T. Hold, R. W. Stein and H. L. Moses. "Transforming growth factor b1suppression of c-myc gene transcription: role in inhibition of keratinocyte proliferation." *Proc. Natl. Acad. Sci. USA.* 87(10):3758-3762, 1990.

34. Pietenpol, J. A., R. W. Stein, E. Moran, P. Yaciuk, R. Schlegal, R. M. Lyons, M. R. Pittelkow, K. Munger, P. M. Howley and H. L. Moses." TGF-b1 inhibition of c-myc transcription and growth in keratinocytes is abrogated by viral transforming proteins with pRB binding domains." *Cell.* 61:777-785, 1990.

35. C. V. Dang, M. McGuire, M. Buckmire, W. M. F. Lee, *Nature* 337, 664 (1989).

36. G. Prendergast and E. Ziff, *Science* 251, 186 (1991).

37. C. V. Dang et al., *Mol. Cell. Biol.* 11, 954 (1991).

38. T. K. Blackwell and H. Weintraub, *Science* 250, 1104 (1990).

39. Y. Nakabeppu, K. Ryder, D. Nathans, *Cell* 55, 907 (1988); T. D. Halazonetis, K. Georgopoulos, M. E. Greenberg, P. Leder, ibid., p. 917; F. J. Rauscher III et al., *Science* 240, 1010 (1988); P. Sassone-Corsi, W. W. Lamph, M. Kamps, I. M. Verma, *Cell* 54, 553 (1988); R. Chiu et al., ibid., p. 541.

40. J. M. Sikela and W. E. Hahn, *Proc. Natl. Acad. Sci. U.S.A.* 84, 3038 (1987); H. Singh, J. H. LeBowitz, A. S. Baldwin, Jr., P. A. Sharp, *Cell* 52, 415 (1988); C. R. Vinson, K. L. Marco, P. F. Johnson, W. H. Landschulz, S. L. McKnight, *Genes Dev.* 2, 801 (1988); H. Singh, R. G. Clerc, J. H. LeBowitz, *BioTechniques* 7, 252 (1989); P. F. Macgregor, C. Abate, T. Curran, *Oncogene* 5, 451 (1990).

41. S. R. Hann and R. N. Eisenman, *Mol. Cell. Biol.* 4, 2486 (1984).

42. M. Kozak, *J. Cell Biol.* 108, 229 (1989).

43. M. Cai and R. W. Davis, *Cell* 61, 437 (1990); R. Benezra, R. L. Davis, D. Lockshon, D. L. Turner, H. Weintraub, ibid, p. 49.

44. S. R. Hann, M. W. King, D. L. Bentley, C. W. Anderson, R. N. Eisenman, *Cell* 52, 185 (1988); A. J. Street, D. Bentley, R. N. Eisenman, unpublished data.

45. W. E. Wright, D. A. Sassoon, V. K. Lin, *Cell* 56, 607 (1989).

46. Q. Chen et al., ibid. 9, 415 (1990).

47. P. D. Gregor, M. Sawadogo, R. G. Roeder, ibid., p. 1730.
48. Y.-F. Hu, B. Luscher, A. Admon, N. Mermod, R. Tijan, *Genes Dev.* 4, 1741 (1990).
49. B. Luscher, E. A. Kuenzel, E. G. Krebs, R. N. Eisenman, *EMBO J.* 8, 1111 (1989).
50. A. B. Lasser et al., *Cell* 58, 823 (1989).
51. E. K. O'Shea, R. Rutkowski, W. F. Stafford III, P. S. Kim, *Science* 245, 646 (1989).
52. J. C. Hu, E. K. O'Shea, P. S. Kim, R. T. Sauer, ibid. 250, 1400 (1990).
53. K. Lech, K. Anderson, R. Brent, *Cell* 52, 179 (1988); G. J. Kato, J. Barrett, M. Villa-Garcia, C. V. Dang, *Mol. Cell. Biol.* 10, 5914 (1990).
54. R. E. Kingston, A. S. Baldwin, P. A. Sharp, *Nature* 312, 280 (1984); R. Kaddurah-Daouk, J. M. Greene, A. S. Baldwin, R. E. Kingston, *Genes Dev.* 1, 347 (1987); R. Onclercq, P. Gilardi, A. Lavenu, C. Cremisi, *J. Virol.* 62, 4533 (1988).
55. M. Ptashne, *Nature* 335, 683 (1988); P. B. Sigler, ibid, 333, 210 (1988); P. J. Mitchell and R. Tijan, *Science* 245, 371 (1989).
56. B. Luscher, R. N. Eisenman, *Genes Dev.* 4, 2025 (1990).
57. L. J. Z. Penn, E. M. Laufer, H. Land, *Semin. Cancer Biol.* 1, 69 (1990).
58. N. Jones, *Cell* 61, 9 (1990).
59. R. Benezra, R. L. Davis, D. Lockshon, D. L. Turner, H. Weintraub, *Cell* 61, 49 (1990). Davis, R. L., Chen, P.-F., Lassar, A. B., & Weintraub, H., *Cell* 60, 733 (1990).
60. E. M. Blackwood, R. N. Eisenman, *Science* 251, 1211 (1991).
61. G. C. Prendergast, D. Lawe, E. B. Ziff, *Cell* 65, 395 (1991).
62. T. K. Blackwell, L. Kretzner, E. M. Blackwood, R. N. Eisenman, H. Weintraub, *Science* 250, 1149 (1990).
63. S. R. Hann, R. N. Eisenman, *Mol. Cell. Biol.* 4, 2486 (1984).
64. B. Luscher, E. A. Kuenzel, E. G. Krebs, R. N. Eisenman, *EMBO J.* 8, 1111 (1989).
65. E. M. Blackwood, B. Lüscher, R. N. Eisenman; unpublished observations.
66. R. N. Eisenman, in *Oncogenes and the Molecular Origins of Cancer* R. A. Weinberg, Eds. (Cold Spring Harbor Press, 1989), pp. 175–221.
67. H. Abrams, L. Rohrschneider, R. N. Eisenman, *Cell* 29, 427 (1982).
68. B. Luscher, R. N. Eisenman, *Mol. Cell. Biol.* 8, 2504 (1988).
69. K. Kelly, B. H. Cochran, C. D. Stiles, P. Leder, *Cell* 35, 603 (1983); M. Dean et al. *J. Biol. Chem.* 261, 9161 (1986).
70. E. A. Clark, et al., *J. Immunol.* 143, 3373 (1989).
71. S. R. Hann, C. B. Thompson, R. N. Eisenman, *Nature* 314, 366 (1985). C. M. Waters, T. D. Littlewood, D. C. Hancock, J. P. Moore, G. I. Evan, *Oncogene* 6, 797 (1991).
72. P. H. Rabbitts, et al., *EMBO J.* 4, 2009 (1985).
73. C. B. Thompson, P. B. Challoner, P. E. Neiman, M. Groudine, *Nature* 314, 363 (1985).
74. M. J. Smith, D. C. Charron-Prochownik, E. V. Prochownik, *Mol. Cell. Biol.* 10, 5333 (1990).
75. R. N. Eisenman, C. Y. Tachibana, H. D. Abrams, S. R. Hann, *Mol. Cell. Biol.* 5, 114 (1985).
76. S. R. Hann, H. D. Abrams, L. R. Rohrschneider, R. N. Eisenman, *Cell* 34, 789 (1983).
77. G. Ramsay, L. Stanton, M. Schwab, J. M. Bishop, *Mol. Cell. Biol.* 6, 4450 (1986).
78. C. A. Spencer, M. Groudine, *Adv. Cancer Res.* 56, 1 (1990).
79. Palmieri, S., P. Kahn, and T. Graf. 1983. Quail embryo fibroblasts transformed by four v-myc containing virus isolates show enhanced proliferation but are non-tumorigenic. *EMBO J.* 2:2385.
80. Karn, J., J. V. Watson, A. D. Lowe, S. M. Green, and W. Vedeckis. 1989. Regulation of cell cycle duration by c-myc levels. *Oncogene* 4:773.
81. Armelin, H. A., M. C. S. Armelin, K. Kelly, T. Stewart, P. Leder, B. H. Cochran, and C. D. Stiles. 1984. Functional role for c-myc in mitogenic response to platelet-derived growth factor. *Nature* 310:655.
82. Sorrentino, V., V. Drosdoff, M. D. McKinney, L. Zeitz, and E. Fleissner. 1986. Potentiation of growth factor activity by exogenous c-myc expression. *Proc. Nat. Acad. Sci.* 83:8167.
83. Stern, D., A. Roberts, N. S. Roche, M. B. Sporn, and R. A. Weinberg. 1986. Differential responsiveness of myc and ras-transfected cells to growth factors: Selective stimulation of myc-transfected cells by epidermal growth factors. *Mol. Cell. Biol.* 6:870.
84. Coppola, J. A. and M. D. Cole. 19896. Constitutive c-myc oncogene expression blocks mouse erythroleukemia cell differentiation but not commitment. *Nature* 320:760.
85. Langdon, W. Y., A. W. Harris, S. Cory, and J. M. Adams. 1986. The c-myc oncogene perturbs B lymphocyte development in Eu-myc transgenic mice. *Cell* 47:11.
86. Freytag, S. 1988. Enforces expression of the c-myc oncogene inhibits cell differentiation by precluding entry into a distinct predifferentiation state in Go/G1. *Mol. Cell. Biol.* 8:1614.
87. Kume, T. U., S. Takada, and M. Obinata. 1988. Probability that the commitment of murine erythroleukemia cell differentiation is determined by the c-myc level. *J. Mol. Biol.* 202:779.
88. Land, H., L. F. Parada, and R. A. Weinberg. 1983. Tumorigenic conversion of primary embryo fibroblasts requires at least two cooperating oncogenes. *Nature* 304:596.
Sinn, E., W. Muller, P. Pattengale, I. Tepler, R. Wallace, and P. Leder, 1987. Coexpression of MMTV/v-Ha-ras and MMTV/c-myc genes in transgenic mice: Synergistic action of oncogenes in vivo. *Cell* 49:465.
van Lohuizen, M., S. Verbeek, P. Krimpenfort, J. Domen, C. Saris, T. Tadazkiewicz, and A. Berns. 1989. Predisposition to lymphomagenesis in pim-1 transgenic mice: Cooperation with c-myc and N-myc in murine leukemia virus-induced tumors. *Cell* 56:673.
Weinberg, R. A. 1989. Oncogenes and multistep carcinogenisis (sic.). In *Oncogenes and the Molecular Origins of Cancer* (ed. R. A. Weinberg), p. 307. Cold Spring Harbor Laboratory Pess, Cold Spring Harbor, New York.
DePamphilis, M. L. 1988. Transcriptional elements as components of eukaryotic origins of DNA replication. *Cell* 52:635.

While the preferred embodiment of the invention has been illustrated and described, it is to be understood that, within the scope of the appended claims, various changes can be made

The embodiments of the invention in which an exclusive property or privilege is claimed are defined as follows:

1. An isolated nucleic acid molecule capable of hybridizing under stringent conditions to the nucleotide sequence residing between positions 1 and 1002 of the mad cDNA shown in FIG. 14 (Seq. I.D. No. 5).

2. The isolated nucleic acid molecule of claim 1, encoding a Mad polypeptide capable of associating with a Max polypeptide.

3. The isolated nucleic acid molecule of claim 1, encoding a polypeptide capable of binding to an antibody that binds to the Mad polypeptide shown in FIG. 14 (Seq. I.D. No: 6).

4. A recombinant expression vector comprising the isolated nucleic acid molecule of claim 1 operably linked to suitable control sequences.

5. Cells transfected or transduced with the recombinant expression vector of claim 4.

6. A method of producing a Mad polypeptide comprising culturing cells of claim 5 to produce a Mad polypeptide that associates with a Max polypeptide.

7. An isolated DNA molecule capable of hybridizing under stringent conditions to the nucleotide sequence residing between positions 355 and 399 of the helix I region of the Mad cDNA shown in FIG. 14 (Seq. I.D. No.: 5).

8. An isolated DNA molecule capable of hybridizing under stringent conditions to the nucleotide sequence residing between positions 418 and 471 of the helix II region of the mad cDNA shown in FIG. 14 (Seq. I.D. No: 5).

9. An isolated DNA molecule comprising the basic region sequence residing between positions 319 and 354 of the mad cDNA shown in FIG. 14 (Seq. I.D. No.: 5).

10. An isolated DNA molecule encoding a polypeptide capable of associating with a Max polypeptide and inhibiting binding of Max to a nucleotide sequence comprising CACGTG, the isolated DNA molecule capable of hybridizing to the nucleotide sequence residing between positions 354 and 472 shown in FIG. 14 but not to the basic region residing between positions 319 and 354 shown in FIG. 14 (Seq. I.D. No.: 5).

* * * * *

UNITED STATES PATENT AND TRADEMARK OFFICE
CERTIFICATE OF CORRECTION

PATENT NO. : 5,302,519                             Page 1 of 7
DATED : April 12, 1994
INVENTOR(S) : Blackwood, Eisenman, and Ayer It is certified that error appears in the above-indentified patent and that said Letters Patent is hereby corrected as shown below:

| COLUMN | LINE | | |
|---|---|---|---|
| On the title page: | | | |
| [56] (Pg. 1) | Ref. Cited (Publs.) | Insert --Luscher, B. and R.N. Eisenman, Genes Dev. 4,2025 (1990).-- | |
| [56] (Pg. 1) | Ref. Cited (Publ. 5) | "(9190)." s/r --(1990).-- | |
| [56] (Pg. 2) | Ref. Cited (Publ. 11) | "91989)." s/r --1989).-- | |
| [56] (Pg. 2) | Ref Cited (Publ. 13) | "J." s/r --K.-- | |
| [56] (Pg. 4) | Ref Cited (Publ. 4) | "vico" s/r --vivo-- | |
| 1 | 21 | "associated" s/r --associates-- | |
| 1 | 45 | "regulators(6)." s/r --regulators (6).-- | |
| 1 | 46 | "to" s/r --by-- | |
| 1 | 60 | "long" s/r --along-- | |
| 1 | 61 | "helic," s/r --helix,-- | |
| 1 | 67 | "of" s/r --or-- (1st occurrence) | |
| 1 | 68 | "of" s/r --to-- (1st occurrence) | |

UNITED STATES PATENT AND TRADEMARK OFFICE
CERTIFICATE OF CORRECTION

PATENT NO. : 5,302,519
DATED : April 12, 1994
INVENTOR(S) : Blackwood, Eisenman, and Ayer It is certified that error appears in the above-indentified patent and that said Letters Patent is hereby corrected as shown below:

| COLUMN | LINE | |
|---|---|---|
| 2 | 18 | "(20,21)." s/r --(20, 21).-- |
| 2 | 68 | "through" s/r --thought-- |
| 3 | 8 | "(33,34)." s/r --(33, 34).-- |
| 4 | 4 | "43" s/r --453-- |
| 4 | 26 | "associated" s/r --associate-- |
| 5 | 13 | "describe" s/r --described-- |
| 6 | 8 | "determing" s/r --determining-- |
| 6 | 20 | "max(amax)." s/r --Max (aMax).-- |
| 6 | 46 | "FIREST" s/r --FIRST-- |
| 7 | 34 | "indicated" s/r --indicate-- |
| 9 | 65 | "C." s/r --C-- |
| 11 | 52 | "acts a" s/r --acts as a-- |
| 16 | 27 | "IPIR" s/r --(PIR--. |
| 16 | 47 | "i collaboration" s/r --in collaboration-- |

UNITED STATES PATENT AND TRADEMARK OFFICE
CERTIFICATE OF CORRECTION

PATENT NO. : 5,302,519
DATED : April 12, 1994
INVENTOR(S) : Blackwood, Eisenman, and Ayer Page 3 of 7

It is certified that error appears in the above-indentified patent and that said Letters Patent is hereby corrected as shown below:

| COLUMN | LINE | |
|---|---|---|
| 16 | 48 | "detection" s/r --deletion-- |
| 16 | 65 | "(14 percent)" s/r --(14 percent).-- |
| 17 | 25 | "resides" s/r --residues-- |
| 17 | 32 | "replacement the" s/r --"replacement of the-- |
| 18 | 1 | "(Pharmacial)]" s/r --(Pharmacia)]-- |
| 19 | 13 | "efficienty" s/r --efficiency-- |
| 19 | 47 | "CACGTG(17)." s/r --CACGTG (17).-- |
| 20 | 48 | "in described above" s/r --described above-- |
| 23 | 43 | "of the these" s/r --of these-- |
| 23 | 45 | "neoplasia(1)." s/r --neoplasia (1).-- |
| 24 | 2 | "(17,36)." s/r --(17, 36).-- |
| 24 | 5 | "doe" s/r --does-- |
| 24 | 59 | "reviews)" s/r --reviews.)-- |
| 25 | 23 | "from from" s/r --from-- |
| 25 | 58 | "(60,61)," s/r --(60, 61).-- |

UNITED STATES PATENT AND TRADEMARK OFFICE
CERTIFICATE OF CORRECTION

PATENT NO. : 5,302,519
DATED : April 12, 1994
INVENTOR(S) : Blackwood, Eisenman, and Ayer It is certified that error appears in the above-indentified patent and that said Letters Patent is hereby corrected as shown below:

| COLUMN | LINE | |
|---|---|---|
| 26 | 24 | "The" s/r --That-- |
| 27 | 9 | "(63,68)." s/r --(63, 68).-- |
| 27 | 29 | "which" s/r --within-- |
| 27 | 38 | "Balb/c- 3t3" s/r --Balb/c- 3T3-- |
| 27 | 45 | "Chomczynski" s/r --Chomcznski-- |
| 28 | 10 | "]$^{125}$I]" s/r --[$^{125}$I]-- |
| 28 | 21 | "frequency" s/r --frequently-- |
| 31 | 19 | "through" s/r --though-- |
| 31 | 21 | "difference" s/r --differences-- |
| 32 | 56 | "competed" s/r --completed-- |
| 33 | 5 | "n-terminus" s/r --N-terminus-- |
| 33 | 38 | "wash" s/r --was-- |
| 33 | 41 | "experiment.." s/r --experiment.-- |

UNITED STATES PATENT AND TRADEMARK OFFICE
CERTIFICATE OF CORRECTION

PATENT NO. : 5,302,519

DATED : April 12, 1994

INVENTOR(S) : Blackwood, Eisenman, and Ayer

It is certified that error appears in the above-indentified patent and that said Letters Patent is hereby corrected as shown below:

| COLUMN | LINE | |
|--------|------|---|
| 34 | 1 | "underline" s/r --underlined-- |
| 34 | 11 | "blotting(data" s/r --blotting (data-- |
| 34 | 39 | "predicated" s/r --predicted-- |
| 34 | 45 | "is" s/r --in-- |
| 35 | 28 | "in" s/r --if-- |
| 36 | 7 | "Max(i.e." s/r --Max (i.e.-- |
| 36 | 27 | "polypetide The" s/r --polypeptide. The-- |
| 36 | 56 | "a unrelated" s/r --an unrelated-- |
| 38 | 6 | "effected" s/r --affected-- |
| 38 | 13 | "over ride" s/r --override-- |
| 38 | 17 | "Cmplexed" s/r --Complexed-- |
| 39 | 10 | "reacfion" s/r --reaction-- |
| 39 | 34 | "pair heterodimers" s/r --pair of heterodimers-- |
| 39 | 36 | "Although," s/r --However,-- |
| 40 | 15 | "a" s/r --an-- |

UNITED STATES PATENT AND TRADEMARK OFFICE
CERTIFICATE OF CORRECTION

PATENT NO. : 5,302,519
DATED : April 12, 1994
INVENTOR(S) : Blackwood, Eisenman, and Ayer It is certified that error appears in the above-indentified patent and that said Letters Patent is hereby corrected as shown below:

| COLUMN | LINE | |
|---|---|---|
| 40 | 63 | "cur-rently" s/r --currently-- |
| 41 | 7 | "$10^8Sf9$" s/r --$10^8$ Sf9-- |
| 45 | 31 | "Chen" s/r --Cheng-- |
| 46 | 26 | "19896" s/r --1986-- |
| 46 | 48 | "Sinn" s/r --89. Sinn-- |
| 46 | 52 | "van" s/r --90. van-- |
| 46 | 53 | "Tadazkiewicz" s/r --Radaszkiewicz-- |
| 46 | 57 | "Weinberg" s/r --91. Weinberg-- |
| 46 | 62 | "DePamphilis" s/r --92. DePamphilis-- |

UNITED STATES PATENT AND TRADEMARK OFFICE
CERTIFICATE OF CORRECTION

PATENT NO. : 5,302,519
DATED : April 12, 1994
INVENTOR(S) : Blackwood, Eisenman, and Ayer It is certified that error appears in the above-indentified patent and that said Letters Patent is hereby corrected as shown below:

| | | |
|---|---|---|
| 46 | 68 | "made" s/r --made.-- |
| 53 (Claim 6 | 67 Line 67) | "culturing cells" s/r --culturing the cells-- |

Signed and Sealed this

Sixth Day of December, 1994

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES:6

( 2 ) INFORMATION FOR SEQ ID NO:1:

( i ) SEQUENCE CHARACTERISTICS:
     ( A ) LENGTH:537 base pairs
     ( B ) TYPE:nucleic acid
     ( C ) STRANDEDNESS:double
     ( D ) TOPOLOGY:linear ( i i ) MOLECULE TYPE:cDNA to mRNA
     ( A ) DESCRIPTION:Human helix-loop- helix zipper protein (max)
     mRNA, start=position 1

( v i ) ORIGINAL SOURCE:
     ( A ) ORGANISM:Homo sapiens; Eukaryota; Animalia; Metazoa;
     Chordata; Vertebrata; Mammalia; Theria; Eutheria;
     Primates; Haplorhini; Catarrhini; Hominidae.

( v i i ) IMMEDIATE SOURCE:Human lymphoid B cell Manca cell line,
     cDNA to mRNA ( i x ) SEQUENCE DESCRIPTION: SEQ ID NO:1:

```
CAGTGGCCGC TCCCTGGGCC GTAGGAAATG AGCGATAACG ATGACATCGA GGTGGAGAGC    60

GACGAAGAGC AACCGAGGTT TCAATCTGCG GCTGACAAAC GGGCTCATCA TAATGCACTG   120

GAACGAAAAC GTAGGGACCA CATCAAAGAC AGCTTTCACA GTTTGCGGGA CTCAGTCCCA   180

TCACTCCAAG GAGAGAAGGC ATCCGGGCC CAAATCCTAG ACAAAGCCAC AGAGTATATC   240

CAGTATATGC GAAGGAAAAA CCACACACAC CAGCAAGATA TTGACGACCT CAAGCGGCAG   300

AATGCTCTTC TGGAGCAGCA AGTCCGTGCA CTGGAGAAGG CGAGGTCAAG TGCCCAACTG   360

CAGACCAACT ACCCCTCCTC AGACAACAGC CTCTACACCA ACGCCAAGGG CAGCACCATC   420

TCTGCCTTCG ATGGGGGCTC AGACTCCAGC TCAGAGTCTG AGCCTGAAGA GCCCCAAAGC   480

AGGAAGAAGC TCCGGATGGA GGCCAGCTAA GCCACTCGGG GCAGGCCAGC AATAAAA      537
```

( 2 ) INFORMATION FOR SEQ ID NO:2:

( i ) SEQUENCE CHARACTERISTICS:
     ( A ) LENGTH:510 base pairs
     ( B ) TYPE:nucleic acid
     ( C ) STRANDEDNESS:double
     ( D ) TOPOLOGY:linear ( i i ) MOLECULE TYPE:cDNA to mRNA
     ( A ) DESCRIPTION:Human helix-loop- helix zipper protein
     ( m a x ) mRNA, alternative sequence corresponds to
     positions 1- 63 and 91-537 in SEQ. ID. NO. 1.

( v i ) ORIGINAL SOURCE:
     ( A ) ORGANISM:Homo sapiens; Eukaryota; Animalia; Metazoa;
     Chordata; Vertebrata; Mammalia; Theria; Eutheria;
     Primates; Haplorhini; Catarrhini; Hominidae.

( v i i ) IMMEDIATE SOURCE:Human lymphoid B cell Manca cell line,
     cDNA to mRNA ( i x ) SEQUENCE DESCRIPTION: SEQ ID NO:2:

```
CAGTGGCCGC TCCCTGGGCC GTAGGAAATG AGCGATAACG ATGACATCGA GGTGGAGAGC    60

GACGCTGACA AACGGGCTCA TCATAATGCA CTGGAACGAA AACGTAGGGA CCACATCAAA   120

GACAGCTTTC ACAGTTTGCG GGACTCAGTC CCATCACTCC AAGGAGAGAA GGCATCCCGG   180

GCCCAAATCC TAGACAAAGC CACAGAGTAT ATCCAGTATA TGCGAAGGAA AAACCACACA   240

CACCAGCAAG ATATTGACGA CCTCAAGCGG CAGAATGCTC TTCTGGAGCA GCAAGTCCGT   300
```

```
GCACTGGAGA AGGCGAGGTC AAGTGCCCAA CTGCAGACCA ACTACCCCTC CTCAGACAAC  360

AGCCTCTACA CCAACGCCAA GGGCAGCACC ATCTCTGCCT TCGATGGGGG CTCAGACTCC  420

AGCTCAGAGT CTGAGCCTGA AGAGCCCCAA AGCAGGAAGA AGCTCCGGAT GGAGGCCAGC  480

TAAGCCACTC GGGGCAGGCC AGCAATAAAA                                   510
```

( 2 ) INFORMATION FOR SEQ ID NO:3:

( i ) SEQUENCE CHARACTERISTICS:
        ( A ) LENGTH:160 amino acids
        ( B ) TYPE:amino acid
        ( D ) TOPOLOGY:linear ( i i ) MOLECULE TYPE:polypeptide
        ( A ) DESCRIPTION:Human helix-loop- helix zipper protein; amino
            acid sequence predicted SEQ.ID.NO. 1

( v i ) ORIGINAL SOURCE:
        ( A ) ORGANISM:Homo sapiens; Eukaryota; Animalia; Metazoa;
            Chordata; Vertebrata;Mammalia; Theria; Eutheria;
            Primates; Haplorhini; Catarrhini; Hominidae.

( v i i ) IMMEDIATE SOURCE:Human lymphoid B cell Manca cell line ( i x ) SEQUENCE DESCRIPTION: SEQ ID NO:3:

```
Met Ser Asp Asn Asp Asp Ile Glu Val Glu Ser Asp Glu Glu Gln Pro
 1           5                  10                 15

Arg Phe Gln Ser Ala Ala Asp Lys Arg Ala His His Asn Ala Leu Glu
            20                  25                 30

Arg Lys Arg Arg Asp His Ile Lys Asp Ser Phe His Ser Leu Arg Asp
        35                  40                 45

Ser Val Pro Ser Leu Gln Gly Glu Lys Ala Ser Arg Ala Gln Ile Leu
    50                  55                 60

Asp Lys Ala Thr Glu Tyr Ile Gln Tyr Met Arg Arg Lys Asn His Thr
65                  70                 75                     80

His Gln Gln Asp Ile Asp Asp Leu Lys Arg Gln Asn Ala Leu Leu Glu
                85                  90                     95

Gln Gln Val Arg Ala Leu Glu Lys Ala Arg Ser Ser Ala Gln Leu Gln
               100                 105                110

Thr Asn Tyr Pro Ser Ser Asp Asn Ser Leu Tyr Thr Asn Ala Lys Gly
           115                 120                 125

Ser Thr Ile Ser Ala Phe Asp Gly Gly Ser Asp Ser Ser Ser Glu Ser
       130                 135                 140

Glu Pro Glu Glu Pro Gln Ser Arg Lys Lys Leu Arg Met Glu Ala Ser
145                 150                 155                160
```

( 2 ) INFORMATION FOR SEQ ID NO:4:

( i ) SEQUENCE CHARACTERISTICS:
        ( A ) LENGTH:151 amino acids
        ( B ) TYPE:amino acid
        ( D ) TOPOLOGY:linear ( i i ) MOLECULE TYPE:polypeptide
        ( A ) DESCRIPTION:Human helix-loop- helix zipper protein; amino
            acid sequence predicted SEQ. ID. NO. 2

( v i ) ORIGINAL SOURCE:
        ( A ) ORGANISM:Homo sapiens; Eukaryota; Animalia; Metazoa;
            Chordata; Vertebrata; Mammalia; Theria; Eutheria;
            Primates; Haplorhini; Catarrhini; Hominidae.

( v i i ) IMMEDIATE SOURCE:Human lymphoid B cell Manca cell line ( i x ) SEQUENCE DESCRIPTION: SEQ ID NO:4:

```
Met Ser Asp Asn Asp Asp Ile Glu Val Glu Ser Asp Ala Asp Lys Arg
 1           5                  10                 15
```

| Ala | His | His | Asn | Ala | Leu | Glu | Arg | Lys | Arg | Arg | Asp | His | Ile | Lys | Asp |
|---|---|---|---|---|---|---|---|---|---|---|---|---|---|---|---|
| | | | 20 | | | | 25 | | | | | 30 | | | |

| Ser | Phe | His | Ser | Leu | Arg | Asp | Ser | Val | Pro | Ser | Leu | Gln | Gly | Glu | Lys |
|---|---|---|---|---|---|---|---|---|---|---|---|---|---|---|---|
| | | 35 | | | | 40 | | | | | 45 | | | | |

| Ala | Ser | Arg | Ala | Gln | Ile | Leu | Asp | Lys | Ala | Thr | Glu | Tyr | Ile | Gln | Tyr |
|---|---|---|---|---|---|---|---|---|---|---|---|---|---|---|---|
| | 50 | | | | 55 | | | | | 60 | | | | | |

| Met | Arg | Arg | Lys | Asn | His | Thr | His | Gln | Gln | Asp | Ile | Asp | Asp | Leu | Lys |
|---|---|---|---|---|---|---|---|---|---|---|---|---|---|---|---|
| 65 | | | | | 70 | | | | 75 | | | | | | 80 |

| Arg | Gln | Asn | Ala | Leu | Leu | Glu | Gln | Gln | Val | Arg | Ala | Leu | Glu | Lys | Ala |
|---|---|---|---|---|---|---|---|---|---|---|---|---|---|---|---|
| | | | | 85 | | | | | 90 | | | | | 95 | |

| Arg | Ser | Ser | Ala | Gln | Leu | Gln | Thr | Asn | Tyr | Pro | Ser | Ser | Asp | Asn | Ser |
|---|---|---|---|---|---|---|---|---|---|---|---|---|---|---|---|
| | | | 100 | | | | 105 | | | | | 110 | | | |

| Leu | Tyr | Thr | Asn | Ala | Lys | Gly | Ser | Thr | Ile | Ser | Ala | Phe | Asp | Gly | Gly |
|---|---|---|---|---|---|---|---|---|---|---|---|---|---|---|---|
| | | 115 | | | | 120 | | | | | 125 | | | | |

| Ser | Asp | Ser | Ser | Ser | Glu | Ser | Glu | Pro | Glu | Glu | Pro | Gln | Ser | Arg | Lys |
|---|---|---|---|---|---|---|---|---|---|---|---|---|---|---|---|
| | 130 | | | | | 135 | | | | | 140 | | | | |

| Lys | Leu | Arg | Met | Glu | Ala | Ser |
|---|---|---|---|---|---|---|
| 145 | | | | | 150 | |

(2) INFORMATION FOR SEQ ID NO:5:

(i) SEQUENCE CHARACTERISTICS:
(A) LENGTH:1002 base pairs
(B) TYPE:nucleic acid
(C) STRANDEDNESS:single
(D) TOPOLOGY:linear (ii) MOLECULE TYPE:cDNA
(A) DESCRIPTION:FIGURE 14

(ix) SEQUENCE DESCRIPTION: SEQ ID NO:5:

| | | | | | |
|---|---|---|---|---|---|
| CGCCAGAGAG | GCTCCCTCAG | CCCTGCTCCG | CGGGGTCCAC | AGCGGGCTCC | ACAGCGGGCT   60 |
| CCATAGCGGG | CTCCACAGCG | GTCCGGCGGC | GGCAGCGAGC | CCGTGGGCAG | TGGGGGTTGG  120 |
| TCCCGTGGCT | CCGGCCCCCG | GTGCAGAATG | GCGGCGGCGG | TTCGGATGAA | CATCCAGATG  180 |
| CTGCTGGAGG | CGGCCGACTA | TCTGGAGCGG | CGGGAGAGAG | AAGCTGAACA | TGGTTATGCC  240 |
| TCCATGTTAC | CATACAATAA | CAAGGACAGA | GATGCCTTAA | ACGGAGGAA  | CAAATCCAAA  300 |
| AAGAATAACA | GCAGTAGCAG | ATCAACTCAC | AATGAAATGG | AGAAGAATAG | ACGGGCTCAT  360 |
| CTTCGCTTGT | GCCTGGAGAA | GTTGAAGGGG | CTGGTGCCAC | TGGGACCCGA | ATCAAGTCGA  420 |
| CACACTACGT | TGAGTTTATT | AACAAAAGCC | AAATTGCACA | TAAAGAAACT | TGAAGATTGT  480 |
| GACAGAAAAG | CCGTTCACCA | AATCGACCAG | CTTCAGCGAG | AGCAGCGACA | CCTGAAGAGG  540 |
| CAGCTGGAGA | AGCTGGGCAT | TGAGAGGATC | CGGATGGACA | GCATCGGCTC | CACCGTCTCC  600 |
| TCGGAGCGCT | CCGACTCCGA | CAGGGAAGAA | ATCGACGTTG | ACGTGGAGAG | CACGGACTAT  660 |
| CTCACAGGTG | ATCTGGACTG | GAGCAGCAGC | AGTGTGAGCG | ACTCTGACGA | GCGGGGCAGC  720 |
| ATGCAGAGCC | TCGGCAGTGA | TGAGGGCTAT | TCCAGCACCA | GCATCAAGAG | AATAAAGCTG  780 |
| CAGGACAGTC | ACAAGGCGTG | TCTTGGTCTC | TAAGAGAGTG | GGCACTGCGG | CTGTCTCCTT  840 |
| GAAGGTTCTC | CCTGTTGGTT | CTGATTAGGT | AACGTATTGG | ACCTGCCCAC | AACTCCCTTG  900 |
| CACGTAAACT | TCAGTGTCCC | ACCTTGACCA | AAATCAGCTT | GTAACTGTT  | TTCAAGGAGG  960 |
| TGCTTAGGAT | TGTGGGTTTC | TGATTGCATC | ACTAGCTTCT | CC         | 1002 |

(2) INFORMATION FOR SEQ ID NO:6:

(i) SEQUENCE CHARACTERISTICS:
(A) LENGTH:221 amino acids
(B) TYPE:amino acid (D) TOPOLOGY:linear (i i) MOLECULE TYPE:polypeptide
 (A) DESCRIPTION:Amino acid sequence from Seq ID No.1 from base 148 to 810; FIGURE 14

(v i) ORIGINAL SOURCE:
 (A) ORGANISM:

(i x) SEQUENCE DESCRIPTION: SEQ ID NO:6:

| Met | Ala | Ala | Ala | Val | Arg | Met | Asn | Ile | Gln | Met | Leu | Leu | Glu | Ala |
| 1 | | | | 5 | | | | | 10 | | | | | 15 |
| Ala | Asp | Tyr | Leu | Glu | Arg | Arg | Glu | Arg | Glu | Ala | Glu | His | Gly | Tyr |
| | | | | 20 | | | | | 25 | | | | | 30 |
| Ala | Ser | Met | Leu | Pro | Tyr | Asn | Asn | Lys | Asp | Arg | Asp | Ala | Leu | Lys |
| | | | | 35 | | | | | 40 | | | | | 45 |
| Arg | Arg | Asn | Lys | Ser | Lys | Lys | Asn | Asn | Ser | Ser | Ser | Arg | Ser | Thr |
| | | | | 50 | | | | | 55 | | | | | 60 |
| His | Asn | Glu | Met | Glu | Lys | Asn | Arg | Arg | Ala | His | Leu | Arg | Leu | Cys |
| | | | | 65 | | | | | 70 | | | | | 75 |
| Leu | Glu | Lys | Leu | Lys | Gly | Leu | Val | Pro | Leu | Gly | Pro | Glu | Ser | Ser |
| | | | | 80 | | | | | 85 | | | | | 90 |
| Arg | His | Thr | Thr | Leu | Ser | Leu | Leu | Thr | Lys | Ala | Lys | Leu | His | Ile |
| | | | | 95 | | | | | 100 | | | | | 105 |
| Lys | Lys | Leu | Glu | Asp | Cys | Asp | Arg | Lys | Ala | Val | His | Gln | Ile | Asp |
| | | | | 110 | | | | | 115 | | | | | 120 |
| Gln | Leu | Gln | Arg | Glu | Gln | Arg | His | Leu | Lys | Arg | Gln | Leu | Glu | Lys |
| | | | | 125 | | | | | 130 | | | | | 135 |
| Leu | Gly | Ile | Glu | Arg | Ile | Arg | Met | Asp | Ser | Ile | Gly | Ser | Thr | Val |
| | | | | 140 | | | | | 145 | | | | | 150 |
| Ser | Ser | Glu | Arg | Ser | Asp | Ser | Asp | Arg | Glu | Glu | Ile | Asp | Val | Asp |
| | | | | 155 | | | | | 160 | | | | | 165 |
| Val | Glu | Ser | Thr | Asp | Tyr | Leu | Thr | Gly | Asp | Leu | Asp | Trp | Ser | Ser |
| | | | | 170 | | | | | 175 | | | | | 180 |
| Ser | Ser | Val | Ser | Asp | Ser | Asp | Glu | Arg | Gly | Ser | Met | Gln | Ser | Leu |
| | | | | 185 | | | | | 190 | | | | | 195 |
| Gly | Ser | Asp | Glu | Gly | Tyr | Ser | Ser | Thr | Ser | Ile | Lys | Arg | Ile | Lys |
| | | | | 200 | | | | | 205 | | | | | 210 |
| Leu | Gln | Asp | Ser | His | Lys | Ala | Cys | Leu | Gly | Leu | | | | |
| | | | | 215 | | | | | 220 | | | | | |